US012029574B2

United States Patent
Arroyo-Gallego et al.

(10) Patent No.: US 12,029,574 B2
(45) Date of Patent: Jul. 9, 2024

(54) METHODS AND APPARATUS FOR ASSESSMENT OF HEALTH CONDITION OR FUNCTIONAL STATE FROM KEYSTROKE DATA

(71) Applicant: Area 2 AI Corporation, Cambridge, MA (US)

(72) Inventors: Teresa Arroyo-Gallego, Madrid (ES); Ashley Holmes, Winthrop, MA (US); Rahul Mahajan, Cambridge, MA (US); Ijah Mondesire-Crump, Boston, MA (US); Tianning Han, Waltham, MA (US)

(73) Assignee: Area 2 A1 Corporation, Cambridge, MA (US)

( * ) Notice: Subject to any disclaimer, the term of this patent is extended or adjusted under 35 U.S.C. 154(b) by 515 days.

(21) Appl. No.: 17/126,050

(22) Filed: Dec. 18, 2020

(65) Prior Publication Data

US 2021/0236044 A1 Aug. 5, 2021

Related U.S. Application Data

(60) Provisional application No. 63/049,508, filed on Jul. 8, 2020, provisional application No. 62/969,638, filed on Feb. 3, 2020.

(51) Int. Cl.
*A61B 5/00* (2006.01)
*A61B 5/08* (2006.01)
(Continued)

(52) U.S. Cl.
CPC .............. *A61B 5/4082* (2013.01); *A61B 5/08* (2013.01); *A61B 5/1101* (2013.01); *A61B 5/112* (2013.01);
(Continued)

(58) Field of Classification Search
CPC ....... A61B 5/4082; A61B 5/08; A61B 5/1101; A61B 5/112; A61B 5/1125; A61B 5/16; A61B 5/125; G16H 50/20; G16H 20/70
See application file for complete search history.

(56) References Cited

U.S. PATENT DOCUMENTS

RE40,993 E * 11/2009 Westerman ......... G06F 3/04886
345/173
7,668,730 B2 * 2/2010 Reardan ................ G16H 40/20
600/300

(Continued)

OTHER PUBLICATIONS

Giancardo, L., et al., Psychomotor Impairment Detection via Finger Interactions with a Computer Keyboard During Natural Typing; published in Scientific Reports, vol. 5, Article 9678, Apr. 2015.
(Continued)

*Primary Examiner* — Carl H Layno
*Assistant Examiner* — Manolis Pahakis
(74) *Attorney, Agent, or Firm* — Outlier Patent Attorneys, PLLC

(57) ABSTRACT

Data regarding typing by a user may be collected and analyzed in order to assess one or more health conditions or functional states of the user. Each health condition that is assessed may be a disease or a symptom of a disease. For instance, based on the typing data, a computer may assess the presence, severity or probability of, or a change in, one or more symptoms such as: mild cognitive impairment, dementia, impairment of fine motor control, impairment of sensory-motor feedback, or behavioral impairment. A computer may calculate keystroke tensors that encode information about the typing. A computer may select or derive features from the keystroke tensors. These features may be fed into one or more machine learning algorithms, which in turn may output an assessment of a health condition or functional state of the user.

20 Claims, 6 Drawing Sheets

(51) Int. Cl.
*A61B 5/11* (2006.01)
*A61B 5/16* (2006.01)
*A61B 5/22* (2006.01)
*G16H 20/70* (2018.01)
*G16H 50/20* (2018.01)

(52) U.S. Cl.
CPC .............. *A61B 5/1125* (2013.01); *A61B 5/16* (2013.01); *A61B 5/225* (2013.01); *A61B 5/4023* (2013.01); *A61B 5/4088* (2013.01); *A61B 5/4803* (2013.01); *A61B 5/7267* (2013.01); *A61B 5/7282* (2013.01); *A61B 5/7475* (2013.01); *G16H 20/70* (2018.01); *G16H 50/20* (2018.01)

(56) References Cited

U.S. PATENT DOCUMENTS

| | | | |
|---|---|---|---|
| 8,285,658 B1* | 10/2012 | Kellas-Dicks | G06F 21/316 706/45 |
| 8,346,680 B2* | 1/2013 | Castleman | G06F 9/453 706/11 |
| 8,671,347 B2* | 3/2014 | Bromer | G06F 3/011 715/744 |
| 9,538,948 B2* | 1/2017 | Dagum | G16H 50/20 |
| 9,867,573 B2 | 1/2018 | Giancardo et al. | |
| 10,506,979 B2* | 12/2019 | Giancardo | A61B 5/7278 |
| 10,694,987 B1* | 6/2020 | Samzelius | A61B 5/4842 |
| 10,964,224 B1* | 3/2021 | Zhang | G09B 19/00 |
| 11,003,839 B1* | 5/2021 | Hatch | G06F 40/166 |
| 11,017,322 B1* | 5/2021 | Du | G06N 20/00 |
| 11,029,846 B1* | 6/2021 | Pophale | G06F 3/04886 |
| 11,157,170 B1* | 10/2021 | Fox | G06F 3/04186 |
| 11,164,319 B2* | 11/2021 | Steele | G06T 7/70 |
| 2005/0065452 A1* | 3/2005 | Thompson | A61B 5/162 128/905 |
| 2006/0195328 A1* | 8/2006 | Abraham | G06Q 30/02 235/382 |
| 2006/0280339 A1* | 12/2006 | Cho | G07C 9/37 382/115 |
| 2007/0139362 A1* | 6/2007 | Colton | G16H 40/67 345/156 |
| 2008/0091639 A1* | 4/2008 | Davis | G06Q 30/02 |
| 2008/0098456 A1* | 4/2008 | Alward | G06F 21/316 726/1 |
| 2009/0002178 A1* | 1/2009 | Guday | A61B 5/0002 340/573.1 |
| 2009/0018407 A1* | 1/2009 | Jung | A61B 3/113 705/2 |
| 2009/0024332 A1* | 1/2009 | Karlov | G16H 50/20 702/19 |
| 2009/0281979 A1* | 11/2009 | Tysowski | G06F 3/0237 707/999.005 |
| 2009/0282369 A1* | 11/2009 | Jones | G06F 16/904 715/848 |
| 2012/0021391 A1* | 1/2012 | Elsmore | G09B 19/00 434/236 |
| 2012/0098750 A1* | 4/2012 | Allen | G06F 21/316 345/169 |
| 2012/0235819 A1* | 9/2012 | Watkins | A61B 5/18 702/19 |
| 2013/0158984 A1* | 6/2013 | Myslinski | G06Q 50/01 704/9 |
| 2013/0176413 A1* | 7/2013 | Lowry | G06Q 10/06398 379/265.06 |
| 2014/0058725 A1* | 2/2014 | Longe | G06F 3/04886 704/9 |
| 2014/0074267 A1* | 3/2014 | Alberts | G16H 50/20 700/92 |
| 2014/0164994 A1* | 6/2014 | Myslinski | G06F 3/04817 715/808 |
| 2016/0345908 A1* | 12/2016 | Samzelius | A61B 5/4088 |
| 2017/0086727 A1* | 3/2017 | Dagum | G06N 5/022 |
| 2017/0090749 A1* | 3/2017 | Marsden | G06F 3/04886 |
| 2017/0300472 A1* | 10/2017 | Parikh | G06F 40/205 |
| 2018/0235548 A1* | 8/2018 | Giancardo | A61B 5/7282 |
| 2018/0300008 A1* | 10/2018 | Rasanen | G06F 3/04886 |
| 2019/0239789 A1* | 8/2019 | Jung | A61B 5/0022 |
| 2019/0311098 A1* | 10/2019 | Baldwin | G06N 3/045 |
| 2019/0362853 A1* | 11/2019 | Friars | G16H 10/20 |
| 2020/0057706 A1* | 2/2020 | Rome | H04L 63/1425 |
| 2020/0356182 A1* | 11/2020 | Kamepalli | G06N 20/00 |
| 2020/0394361 A1* | 12/2020 | Parikh | G06F 40/274 |
| 2021/0181863 A1* | 6/2021 | Gatson | G06F 1/1669 |
| 2021/0236044 A1* | 8/2021 | Arroyo-Gallego | A61B 5/4023 |
| 2021/0240805 A1* | 8/2021 | Knoppert | G06F 3/023 |
| 2021/0365630 A1* | 11/2021 | Itani | G06F 16/335 |
| 2022/0083633 A1* | 3/2022 | Hazan | G06F 21/316 |
| 2022/0273227 A1* | 9/2022 | Chen | A61B 5/11 |

OTHER PUBLICATIONS

Giancardo, L., et al., Computer keyboard interaction as an indicator of early Parkinson's disease; published in Scientific Reports, vol. 6, Article 34468, Oct. 2016.

Arroyo-Gallego, T., et al., Detection of Motor Impairment in Parkinson's Disease Via Mobile Touchscreen Typing; published in IEEE Transactions on Biomedical Engineering, vol. 64, No. 9, Sep. 2017.

Arroyo-Gallego, T., et al., Detecting Motor Impairment in Early Parkinson's Disease via Natural Typing Interaction With Keyboards: Validation of the neuroQWERTY Approach in an Uncontrolled At-Home Setting; published in Journal of Medical Internet Research, vol. 20, iss. 3, e89, year 2018.

Matarazzo, M., et al., Remote Monitoring of Treatment Response in Parkinson's Disease: The Habit of Typing on a Computer; published in Movement Disorders, vol. 34, No. 10, year 2019.

Gao, C., et al., Objective assessment of bradykinesia in Parkinson's disease using evolutionary algorithms: clinical validation; published in Translational Neurodegeneration, 7:18, year 2018.

Goetz, C., et al. MDS-UPDRS The MDS-sponsored Revision of the Unified Parkinson's Disease Rating Scale; published 2008.

Iakovakis, D., et al., Screening of Parkinsonian subtle fine-motor impairment from touchscreen typing via deep learning; published in Scientific Reports, vol. 10, Article 12623, Jul. 28, 2020.

Lau, S., et al., Clusters and Markers for Keystroke Typing Rhythms; published in Proceedings of LASER 2014 Learning from Authoritative Security Experiment Results, Oct. 2014.

Lee, C., et al., A Validation Study of a Smartphone-Based Finger Tapping Application for Quantitative Assessment of Bradykinesia in Parkinson's Disease; published in PLOS One, DOI 10.1371/journal.pone.0158852, Jul. 2016.

Londrai, A., et al., A method to detect keystrokes using accelerometry to quantify typing rate and monitor neurodegenerative progression; published in Proceedings of the International Congress on Neurotechnology, Electronics and Informatics (NEUROTECHNIX 2013), pp. 54-59, year 2013.

Memedi, M., et al., Automatic and Objective Assessment of Alternating Tapping Performance in Parkinson's Disease; published in Sensors, 13(12): 16965-16984, Dec. 2013.

Ntracha, A., et al., Detection of Mild Cognitive Impairment Through Natural Language and Touchscreen Typing Processing; published in Frontiers in Digital Health, DOI 10.3389/fdgth.2020.567158, Oct. 8, 2020.

Stringer, G., et al., Can you detect early dementia from an email? A proof of principle study of daily computer use to detect cognitive and functional decline; published in International Journal of Geriatric Psychology 33(7):867-874. doi: 10.1002/gps.4863, year 2018.

Trager, M., et al., Arrhythmokinesis is evident during unimanual not bimanual finger tapping in Parkinson's disease; published in Journal of Clinical Movement Disorders 2:8. doi: 10.1186/s40734-015-0019-2, year 2018.

Trewin, S., et al., Keyboard and mouse errors due to motor disabilities; published in International Journal of Human-Computer Studies, vol. 50, Issue 2, pp. 109-144, Feb. 1999.

(56) References Cited

OTHER PUBLICATIONS

Vizer, et al. Detecting Cognitive Impairment Using Keystroke and Linguistic Features of Typed Text: Toward an Adaptive Method for Continuous Monitoring of Cognitive Status; published in Proceedings of the Symposium of the Austrian HCI and Usability Engineering Group (USAB 2011), year 2011.

* cited by examiner

METHODS AND APPARATUS FOR ASSESSMENT OF HEALTH CONDITION OR FUNCTIONAL STATE FROM KEYSTROKE DATA

RELATED APPLICATIONS

This application claims the benefit of U.S. Provisional Application No. 62/969,638 filed Feb. 3, 2020 (the "638 Provisional") and the priority of U.S. Provisional Application No. 63/049,508 filed Jul. 8, 2020 (the "508 Provisional"). As used herein, the "Provisionals" means the 638 Provisional and the 508 Provisional.

FIELD OF TECHNOLOGY

The present invention relates generally to using keystroke data to assess a health condition or functional state of a user.

SUMMARY

In some implementations of this invention, data regarding typing by a user is collected and analyzed in order to assess one or more health conditions of the user. Each health condition that is assessed may be a disease or a symptom of a disease.

For instance, based on the typing data, a computer may assess the presence, severity or probability of, or a change in, one or more symptoms such as: mild cognitive impairment; dementia; impairment of fine motor control; impairment of sensory-motor feedback; or behavioral impairment.

Or, for instance, based on the typing data, a computer may assess the presence, severity or probability of, or a change in, one or more diseases, such as: Alzheimer's disease; dementia with Lewy bodies, Parkinson's disease; multiple sclerosis; amyotrophic lateral sclerosis; frontotemporal degeneration; osteoarthritis; psoriatic arthritis; rheumatoid arthritis; or carpal tunnel syndrome.

The analysis of typing data may enable accurate assessment of a particular health condition, because that health condition may affect typing in a manner that is unique to, characteristic of, or positively correlated with, that health condition. Put differently, the impact of a particular health condition on a user's typing may comprise a unique or characteristic "signature" of that health condition.

In some use scenarios, the typing data is gathered while a user types naturally, without any restrictions regarding the timing, content or length of the text being typed. In other use scenarios, the typing data is gathered while a user types in a semi-controlled setting, in which the timing, content and/or length of the text being typed is controlled. In either approach (natural typing or typing in a semi-controlled setting), the user may type on a mechanical keyboard, a touch screen or any other I/O device.

Based on the raw typing data, a computer may calculate or process augmented keystroke data. The augmented keystroke data may include data regarding: (a) time of key press; (b) time of key release; (c) keyboard zone; (d) type of key (e.g., alphanumeric, space, modifier, punctuation, backspace, and emoji); (e) assisted keystroke events (e.g., autocorrect); (f) tap precision (e.g., if typing on a touch screen, how close to the target did the finger press); and (g) context of typing session (e.g., type of software hosting session, and type of hardware measuring keyboard events).

Based on the augmented keystroke data, a computer may calculate enriched keystroke data. The enriched keystroke data may include data regarding: (a) hold time (time between press and release of a key); (b) flight time (e.g., time between press of a key and press of next key); (c) delay (e.g., time between release of a key and press of next key); (d) zonal distance (e.g., distance between keyboard zones for two consecutive keystrokes); (e) trajectory (e.g., keyboard zones for a sequence of keystrokes); (f) metrics for a sequence of keystrokes; (g) pauses; (h) syntax; and (i) semantics.

Based on the augmented keystroke data, a computer may calculate keystroke tensors. For instance, a computer may calculate a separate keystroke tensor for each typing session by a user. Each keystroke tensor may comprise a nested, variable-length list. For example, each keystroke tensor may comprise a ragged tensor, as that term is used in the TensorFlow® programming language.

A computer may select features from—or compute features based on—the keyboard tensors. In some cases, the features are automatically selected by a computer program in the course of calculating the features. For instance, a computer may perform one or more autoencoder algorithms that compute and select the features. Or, for instance, a computer may perform principal component analysis on data in the keystroke tensors, and may output features that are principal components. In some other cases, features are heuristically selected by one or more humans, and then values of the features are calculated by a computer. For instance, the heuristically selected features may comprise descriptive statistics or inferential statistics regarding data in a keystroke tensor.

The features (which are derived from the typing data) may be fed as input into one or more trained machine learning (ML) algorithms. Based on the inputted features, the ML algorithm(s) may assess the presence, severity or probability of, or a change in, one or more symptoms. Likewise, based on the inputted features, the ML algorithm(s) may assess the presence, severity or probability of, or a change in, one or more diseases. Also, based on the inputted features, the ML algorithm(s) may assess a functional state of a user or a change in a functional state of the user.

Based on the assessed health condition, a computer may recommend one or more one or more drugs or non-pharmacologic treatments, which may be employed to treat the health condition.

In some implementations of this invention, data regarding typing by a user is collected and analyzed in order to assess one or more functional states of the user. For instance, the one or more functional states that are assessed may include: (a) aspects of motor function, such as balance, reaction time, physical strength, body awareness, coordination, tremor, speech, facial expression, agility, gait, motion fluidity, respiratory quality, dexterity, bilateral hand coordination, right hand coordination, left hand coordination, steadiness, precision, general velocity, and seasonality of motor stability; (b) aspects of cognitive function, such as central processing, executive function, complex attention, nonverbal memory, language/verbal skills, social cognition, visual motor ability, processing speed, attention and concentration, perception, sensation, visuospatial function, verbal memory, mental tracking, and mental monitoring; and (c) aspects of behavioral function, such as mood, social interactions and behavioral control. In some cases, an assessment of a functional state includes an assessment of changes in that state. In some cases, the assessment of one or more functional states is outputted by one or more machine learning (ML) algorithms. In some cases, the assessment of one or more functional states is presented to medical workers to assist in the diagnosis or treatment of a health condition. In some cases, an assessment of more or more functional states is fed as an input into one or more ML algorithms, which in turn output an assessment of one or more health conditions.

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the Field of Technology section is not limiting; instead it identifies, in a general, non-exclusive manner, a field of technology to which some implementations of this invention generally relate.

The above Figures are not necessarily drawn to scale. The above Figures show illustrative implementations of this invention, or provide information that relates to those implementations. The examples shown in the above Figures do not limit this invention. This invention may be implemented in many other ways.

DETAILED DESCRIPTION

General

Figure 1:
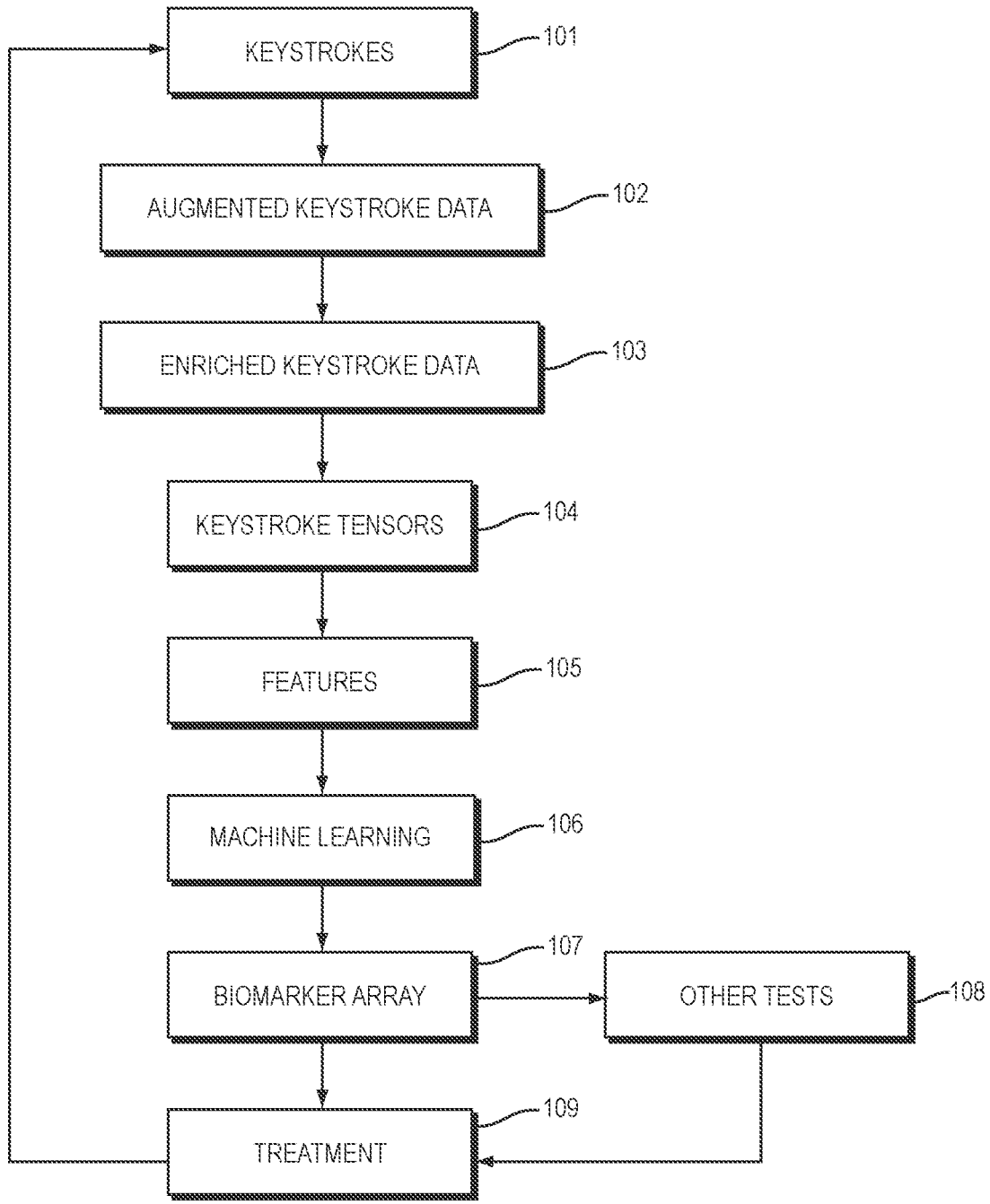
FIG. 1 is a flowchart of a method of assessing a health condition or functional state of a user.

FIG. 1 is a flowchart for a method of assessing a health condition or functional state of a user, in an illustrative implementation of this invention. In FIG. 1, the method includes at least the following steps: Measure keystrokes typed by a user (Step 101). Calculate augmented keystroke data (Step 102). Calculate enriched keystroke data (Step 103). Create multiple keystroke tensors, including at least one keystroke tensor for each typing session in a set of the user's typing sessions (Step 104). Calculate features, based on the keystroke tensors (Step 105). Input the features into a machine learning model (Step 106), which in turn outputs a biomarker array that is indicative of an assessment of a health condition or functional state of the user (Step 107). Based on the biomarker array, optionally select other tests to diagnose or monitor a health condition or functional state of the user, and perform the tests (Step 108). Based on the biomarker array and/or the results of the other tests, select a treatment for a health condition or functional state of the user and then apply the treatment. (Step 109). After or during the treatment, perform Steps 101 to 107 (or Steps 101 to 108) again to monitor how the treatment is affecting the condition or functional state.

Measuring Keystrokes

In illustrative implementations of this invention, keystrokes of a user are analyzed in order to assess a health condition or functional state of the user.

In some cases, the keystrokes occur while a user is typing on a keyboard (e.g., a mechanical keyboard). During the typing, keys of the keyboard may physically move relative to another portion of the keyboard. For instance, a key may move in a first direction (e.g., down) relative to another portion of the keyboard when the user presses against the key and may move in a second direction (e.g., up) relative to that other portion of the keyboard when the user releases the key.

In the context of a keyboard, each keystroke may comprise a key press, a key hold, and a key release. In the context of a keyboard: (a) a key press may occur when a finger of the user presses against a key of the keyboard, causing the key to move in a first direction (e.g., down) towards a static portion of the keyboard; (b) a key hold may occur when the finger continues to exert pressure on the key, after the key press; and (c) a key release may occur when the finger releases pressure from the key, allowing the key to move in a second, opposite direction (e.g., up) away from the static portion of the keyboard. Each keystroke may be a physical event that comprises pressing, holding or releasing a key on a keyboard.

The keyboard may detect when a key is pressed and released. For instance, each individual key: (a) may be an electrical switch that closes and opens when the key is pressed and released, respectively (or vice versa); and (b) may comprise a plunger with metal electrical contacts on one or more of its sides and with a spring below it. Or, for instance, the key may be an optical switch that, depending on its position, blocks a laser beam or allows the laser beam to pass. Or, for instance, movement of the key may be detected by a Hall effect sensor (e.g., the Hall effect sensor may be adjacent to the key and may detect movement of a magnet in the key).

In some cases, the keystrokes occur when a user is typing on a touchscreen. The touchscreen may be part of a smartphone, tablet computer, notebook computer, laptop computer or other mobile computing device.

Again, in the context of a touchscreen, each keystroke may comprise a key press, a key hold, and a key release. In the context of a touchscreen: (a) a key press may occur when a finger of the user touches the screen at a point of contact that is within a specified distance of a location (on the screen) that represents a key; (b) a key hold may occur when the finger continues to touch the screen, after the key press; and (c) a key release may occur when the finger ceases to touch the screen.

The touchscreen may employ any technology that detects when and where the screen is touched. For instance, the touchscreen may comprise a resistive touchscreen, surface acoustic wave touchscreen, capacitive touchscreen, surface capacitance touchscreen, projected capacitance touchscreen, mutual capacitance touchscreen, self-capacitance touchscreen, infrared grid touchscreen, infrared acrylic projection touchscreen, optical imaging touchscreen, dispersive signal touchscreen, or acoustic pulse recognition touchscreen.

In some use scenarios, the keystrokes occur during what we sometimes call a "natural" typing session. During a natural typing session, a user types freely, whenever and whatever the user wants. For instance, a natural typing session may comprise the user typing during the ordinary course of the user's activities, without any instructions regarding when or what to type.

In some other use scenarios, the keystrokes occur during what we sometimes call a "controlled" typing session. During a controlled typing session, a user types text which has content that the user has been instructed to type, or types in a manner in which the user has been instructed to type.

In some use scenarios, the user is free at any time to select or to change which hardware (e.g., keyboard or touchscreen) the user is typing on. In some other use scenarios, the user is told which hardware (e.g., keyboard or touchscreen) to type on at a given time.

A typing session may be "natural", as that term is used herein, even if the user is required to type on particular hardware (e.g., keyboard or touchscreen).

Augmented Keystroke Data

In illustrative implementations of this invention, a computer processes what we sometimes call "augmented keystroke data". The computers may extract the augmented keystroke data from, or receive the augmented keystroke data as, a data stream, as discussed in more detail below.

Figure 2:
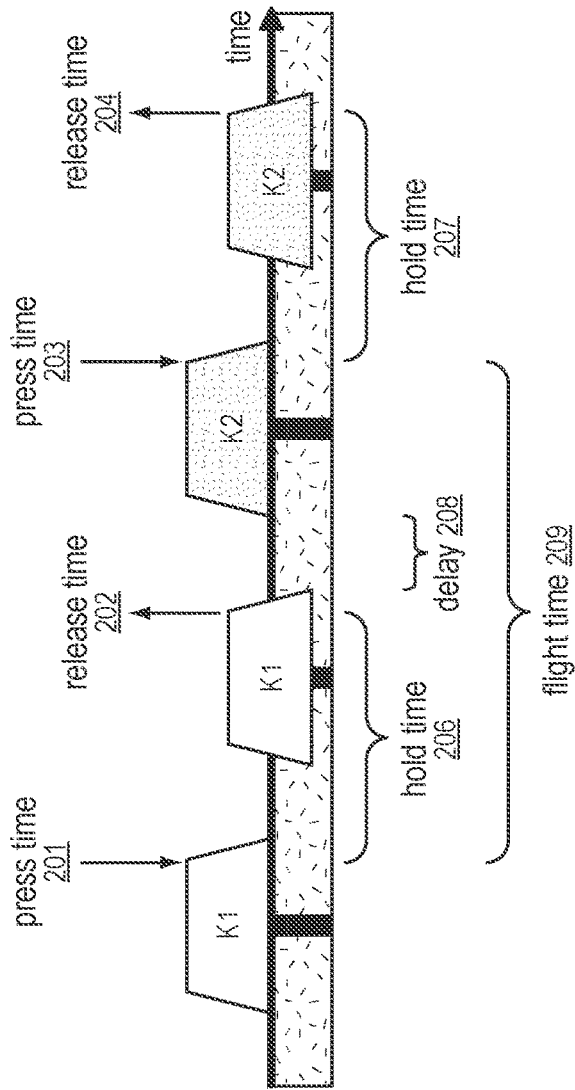
FIG. 2 illustrates press time and release time of a keystroke.

The augmented keystroke data may include, for each keystroke: (a) time of key press; and (b) time of key release. FIG. 2 illustrates press time 201 and release time 202 of a keystroke.

The augmented keystroke data may also specify a keyboard zone in which the keystroke occurs. For purposes of classifying where a keystroke occurs, the keyboard may be treated as comprising multiple non-overlapping zones. For instance, the number of keyboard zones may be: (a) two, three, four, five, six, seven, eight, or nine; or (b) greater than or equal to two and less than or equal to one-third of the total number of keys in the keyboard. In the example shown in FIG. 3, a keyboard comprises six zones 1, 2, 3, 4, 5, and 6.

The augmented keystroke data may also specify the type of key that is pressed. For instance, the types of keys may include at least: (a) alphanumeric; (b) space; (c) punctuation; (d) modifier (e.g., Shift, Control, Alt); and (e) emoji. Alternatively, other classifications may be employed as key types. For instance, alphabetic and numeric may be treated as two separate types of keys. Or, for instance, navigation keys (e.g., space bar, up, down, right, left, Backspace, Home, End) may be treated as a key type. Or, for instance, "delete" may be treated as its own key type. Or, for instance, "backspace" may be treated as its own key type. Or, for instance, a key type for user-initiated corrective keystrokes may include both "delete" and "backspace".

The augmented keystroke data may also include information regarding assisted typing events that occur during a typing session. For instance, an assisted typing event may be an autocorrect that changes a character without any movement or action by a user. Or, for instance, an assisted typing event may comprise a user selecting a suggested word or phrase—such as by moving a computer cursor to a display of the suggested word or phrase and clicking on it, or by touching a finger to a display of the suggested word or phrase. The suggested word or phrase may be a prediction, by a computer, of how to complete a string of one or more characters that the user has entered. In some cases, the augmented keystroke data includes information regarding autocorrect events, such as the time at which each autocorrect event occurs in a typing session or the type of character (e.g., alphanumeric or punctuation) that is autocorrected. Likewise, in some cases, the augmented keystroke data includes information regarding a user's selection of a computer-suggested phrase or word, such as the user's reaction time before selecting the suggested text.

The augmented keystroke data may also include data regarding the context of a typing session. For instance, this data may specify, among other things: (a) start time of the typing session; (b) a software application that is hosting the session (or otherwise processing or pre-processing data that is indicative of, or based on, measurements taken by a keyboard or touchscreen); (c) the hardware that is measuring the keyboard events during the session (e.g., the model of keyboard or touchscreen that is being employed for the typing); and (d) a state, during the typing session, of the device measuring the keystrokes.

In some use scenarios, the user is typing on a touchscreen and the augmented keystroke data includes data regarding tap precision—e.g., the distance by which a user's finger misses the correct location for touching a displayed key on the screen. This tap precision data may specify a distance between: (a) a point of contact at which a finger of the user touches the screen; and (b) a region or point on the screen where the key is displayed on the screen. Alternatively, this tap precision data may specify a two-dimensional vector that originates at the displayed key and terminates at the point of contact of the user's finger (or vice versa).

Figure 4:
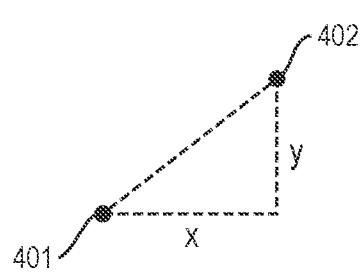
FIG. 4 illustrates location precision.

FIG. 4 illustrates tap precision. In FIG. 4, a touchscreen displays a key at point 401, while a user's finger touches a touchscreen at point 402. The augmented keystroke data may specify Euclidian distance between these two points. Or the augmented keystroke data may specify a two-dimensional vector that originates at point 401 and terminates at point 402 (or vice versa).

In some cases, the augmented keystroke data does not specify the identity of any particular alphanumeric key. For instance, in some cases, if the user presses the "m" key in FIG. 3, the augmented keystroke data specifies that an alphanumeric key in zone 4 of the keyboard was pressed—but does not specify that the letter "m" was pressed. This helps ensure privacy, tending to make it difficult or impossible to accurately reconstruct the content of what is being typed.

As used herein, "key-anonymized augmented data" means augmented keystroke data that does not specify the identity of any specific alphanumeric key.

In some cases: (a) a client computer sends key-anonymized augmented data via one or more communication networks (e.g., via the Internet and/or one or more wireless communication networks) to a server computer; and (b) the server computer never receives data that specifies the identity of the alphanumeric keystrokes that were used to generate the key-anonymized augmented data. The server computer may transform the key-anonymized augmented data, in order to calculate one or biomarkers that are indicative of a health condition or functional state.

In some cases, the client computer extracts (or derives) all or part of the key-anonymized augmented data from a data stream that specifies or encodes the identity of at least alphanumeric keys.

As used herein, a "key-identifying stream" means a data stream that specifies or encodes the identity of at least alphanumeric keys. As a non-limiting example, if a user types a lower case letter "b", then a key-identifying stream may specify a lower case letter "b" keystroke.

In the context of a keyboard, the generation of key-anonymized augmented data from a key-identifying stream may involve multiple steps. For instance: For each keystroke, the keyboard may generate data (e.g., scan code) that specifies row and column of the key pressed in the keystroke. For each keystroke, the row and column data may, in effect, encode the identity of a specific key. A microcontroller in the keyboard may convert this data into a key-identifying stream which, for each keystroke, specifies the particular key that is pressed in the keystroke. The microcontroller in the keyboard may send this key-identifying stream to a client computer. The client computer may extract (or derive), from the key-identifying stream, all or part of the key-anonymized augmented data. The client computer may send the key-anonymized augmented data to a server computer.

Likewise, in the context of a touchscreen, the generation of key-anonymized augmented data from a key-identifying stream may involve multiple steps. For instance: Each keystroke may comprise a finger tap on the screen. The screen may be housed in a mobile computing device, such as a smartphone, tablet computer, or notebook computer. For each keystroke, the screen may generate data that specifies two-dimensional (2D) coordinates of a point at which a user is touching the screen. For each keystroke, the two-dimensional coordinates may, in effect, encode the identity of a specific key (e.g., a letter "b"). A first processer in the mobile computing device may convert this data into a key-identifying stream which, for each touch keystroke, specifies the particular key that is represented by the keystroke. The first processor (or another processor in the mobile computing device): (a) may extract (or derive), from the key-identifying stream, all or part of the key-anonymized augmented data; and (b) may send the key-anonymized augmented data to a server computer.

In some cases, a keyboard or touchscreen outputs data that is time-stamped (e.g., specifying the time at which a key press occurs.) In some other cases: (a) a keyboard or touchscreen outputs a stream of data that is not time-stamped (e.g., specifying a key press but not when it occurs); and (b) a computer (e.g., in a client computer or mobile computing device) adds timestamps to the data in real time. In either approach, the timestamps may be expressed relative to a point of time in a typing session (e.g., amount of time elapsed since start of the session) or may be expressed relative to a reference time. For instance, each timestamp may include date, unix time, and time zone.

In some cases, all or some of the augmented keystroke data is normalized, standardized, shifted, rescaled, or clipped.

Enriched Keystroke Data

In some cases, a computer calculates additional information regarding keystrokes typed by a user. We sometimes call this additional information "enriched keystroke data". The enriched keystroke data may be derived from, or based at least in part on, augmented keystroke data.

The enriched keystroke data may include hold time of each keystroke. The hold time of a keystroke may be the amount of time that elapses between the press time and release time of the keystroke. In other words, the hold time of a keystroke may be equal to the difference between the release time of the keystroke and the press time of the keystroke.

The enriched keystroke data may also include flight time for each pair of consecutive keystrokes. For each pair of consecutive keystrokes, the flight time may be the amount of time that elapses between the press times of the two keystrokes in the pair. In other words, for each pair of consecutive keystrokes, the flight time may be equal to the difference between press time of the second keystroke in the pair and press time of the first keystroke in the pair. More generally, flight time may be calculated as the temporal interval between corresponding points in time in two consecutive keystrokes (e.g., between press times of the two consecutive keystrokes, or between release times of the two consecutive keystrokes, or between times in the temporal middle of the two consecutive keystrokes). In this section titled "Enriched Keystroke Data", the terms "first" and "second" refer to temporal order such that the second keystroke occurs after the first.

The enriched keystroke data may also include delay for each pair of consecutive keystrokes. For each pair of consecutive keystrokes, the delay may be equal to the amount of time that elapses between the release time of the first keystroke in the pair and press time of the second keystroke in the pair. In other words, for each pair of consecutive keystrokes, the delay may be equal to the difference between the press time of the second keystroke in the pair and the release time of the first keystroke in the pair.

In FIG. 2, hold time 206 of keystroke K1 is the amount of time that elapses between press time 201 and release time 202 of keystroke K1. Likewise, hold time 207 of keystroke K2 is the amount of time that elapses between press time 203 and release time 204 of keystroke K2. In FIG. 2, flight time 209 is the difference between press time 203 of keystroke K2 and press time 201 of keystroke K1. In FIG. 2, delay 208 is the difference between press time 203 of keystroke K2 and release time 202 of keystroke K1.

Hold time, flight time and delay may be expressed in mathematical terms, as follows:

$$HT_n = R_{k_n} - P_{k_n} \qquad (Eq\ 1)$$

$$FT_n = P_{k_{n+1}} - P_{k_n} \qquad (Eq\ 2)$$

$$DL_n = P_{k_{n+1}} - R_{k_n} \qquad (Eq\ 3)$$

where $HT_n$ is hold time of the $n^{th}$ keystroke, $FT_n$ is flight time for the pair of keystrokes that starts with the $n^{th}$ keystroke, $DL_n$ is delay for the pair of keystrokes that starts with the $n^{th}$ keystroke, $P_{k_n}$ is press time of the $n^{th}$ keystroke, $P_{k_{n+1}}$ is press time of the $(n+1)^{th}$ keystroke, and $R_{k_n}$ is release time of the $n^{th}$ keystroke Zonal Distance: The enriched keystroke data may also include zonal distance for each pair of consecutive keystrokes in a sequence of keystrokes. For each pair of consecutive keystrokes, the zonal distance may be indicative of a relative or absolute physical distance between: (a) a point in a first keyboard zone in which the first keystroke occurs and (b) a point in a second keyboard zone in which the second keystroke occurs. If both keystrokes are in the same keyboard zone, the zonal distance may be zero. The zonal distance may be distance in a single dimension along an axis of the keyboard that is parallel to a row or column of keys (e.g., in a QWERTY keyboard, a row of keys that includes Q, W, E, R, T, U, I, O and P).

Figure 3:
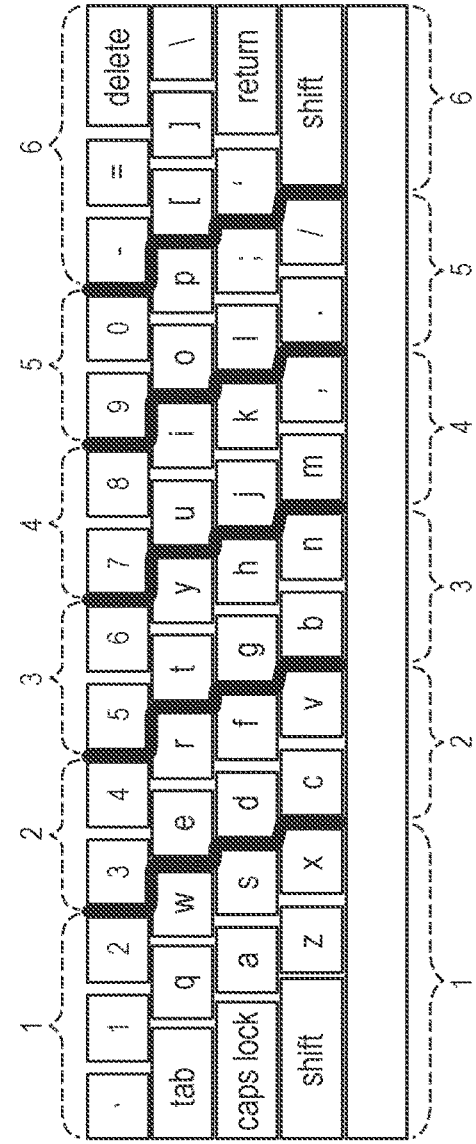
FIG. 3 illustrates keyboard zones.

The zonal distance may be a signed or unsigned number. In some cases, the zonal distance is an unsigned number that indicates the magnitude of the distance between the keyboard zones for two consecutive keystrokes, respectively. Alternatively, for each pair of consecutive keystrokes, the zonal distance may be a signed number that indicates spatial position of the first keyboard zone (where the first keystroke occurs) relative to the second keyboard zone (where the second keystroke occurs). For instance, in cases in which the keyboard zones change as displacement along a right-left axis of the keyboard changes (as shown in FIG. 3), the zonal distance may be a signed number that indicates whether the first keyboard zone (where the first keystroke occurs) is to the right or to the left of the second keyboard zone (where the second keystroke occurs).

Trajectory: The enriched keystroke data may also include trajectory for a temporal sequence of keystrokes. A trajectory may list, in temporal order, transitions between keyboard zones. As a non-limiting example, in FIG. 3, a 4-gram may consist of a sequence of four keystrokes W, B, G and M (in that temporal order, i.e., first W, second B, third G, and fourth M). In this example, the trajectory for the 4-gram would be zone 1→zone 3,→zone 3→zone 4.

Figure 5:
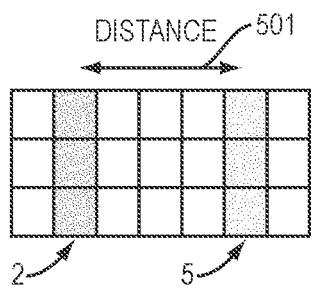
FIG. 5 illustrates distance between keyboard zones.
Figure 6:
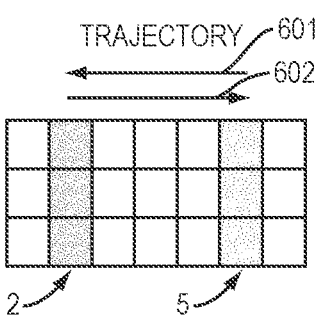
FIG. 6 illustrates trajectory of keystrokes.

In FIGS. 5 and 6, two consecutive keystrokes occur in a bi-gram, one in zone 2 and the other in zone 5. Distance 501 is distance between a point in zone 2 and a point in zone 5. If the keystroke in zone 2 precedes the keystroke in zone 5, then the bigram has trajectory 602, that is zone 2→zone 5. However, if the keystroke in zone 5 precedes the keystroke in zone 2, then bigram has trajectory 601, i.e., zone 5→zone 2.

Pauses: The enriched keystroke data may also include pauses. Each pause may be the amount of time elapsed between keystrokes in different language events or units, which language events or units are indicated by transitions in key types. As a non-limiting example, a pause may be the amount of time elapsed between two words. For instance, a pause may be the amount of time elapsed between a first time (e.g., press time or release time) associated with a first alphanumeric keystroke and a second time (e.g., press time or release time) associated with a second alphanumeric keystroke, where the first and second alphanumeric keystrokes precede and follow, respectively, a space keystroke. As another non-limiting example, a pause may be the amount of time elapsed between two sentences or two phrases of a single sentence. For instance, a pause may be the amount of time elapsed between a first time (e.g., press time or release time) associated with a first alphanumeric keystroke and a second time (e.g., press time or release time) associated with a second alphanumeric keystroke, where the first and second alphanumeric keystrokes precede and follow, respectively, a temporal sequence of two or more keystrokes, and where the temporal sequence of two or more keystrokes consists of at least one punctation keystroke (other than an apostrophe immediately before the letter "s") and/or at least one Enter keystroke, and optionally also consists of space keystrokes. Alternatively, if the augmented keystroke data includes alphabetic keys as a separate key type, then pauses between alphabetic keystrokes (rather than alphanumeric keystrokes) may be employed. In some cases, a stream of inter-key pauses is be modeled as a probability distribution resulting from the combination of one or more random variables used to represent subprocesses underlying the pause signal (e.g. motoric execution, language latency)

Figure 8:
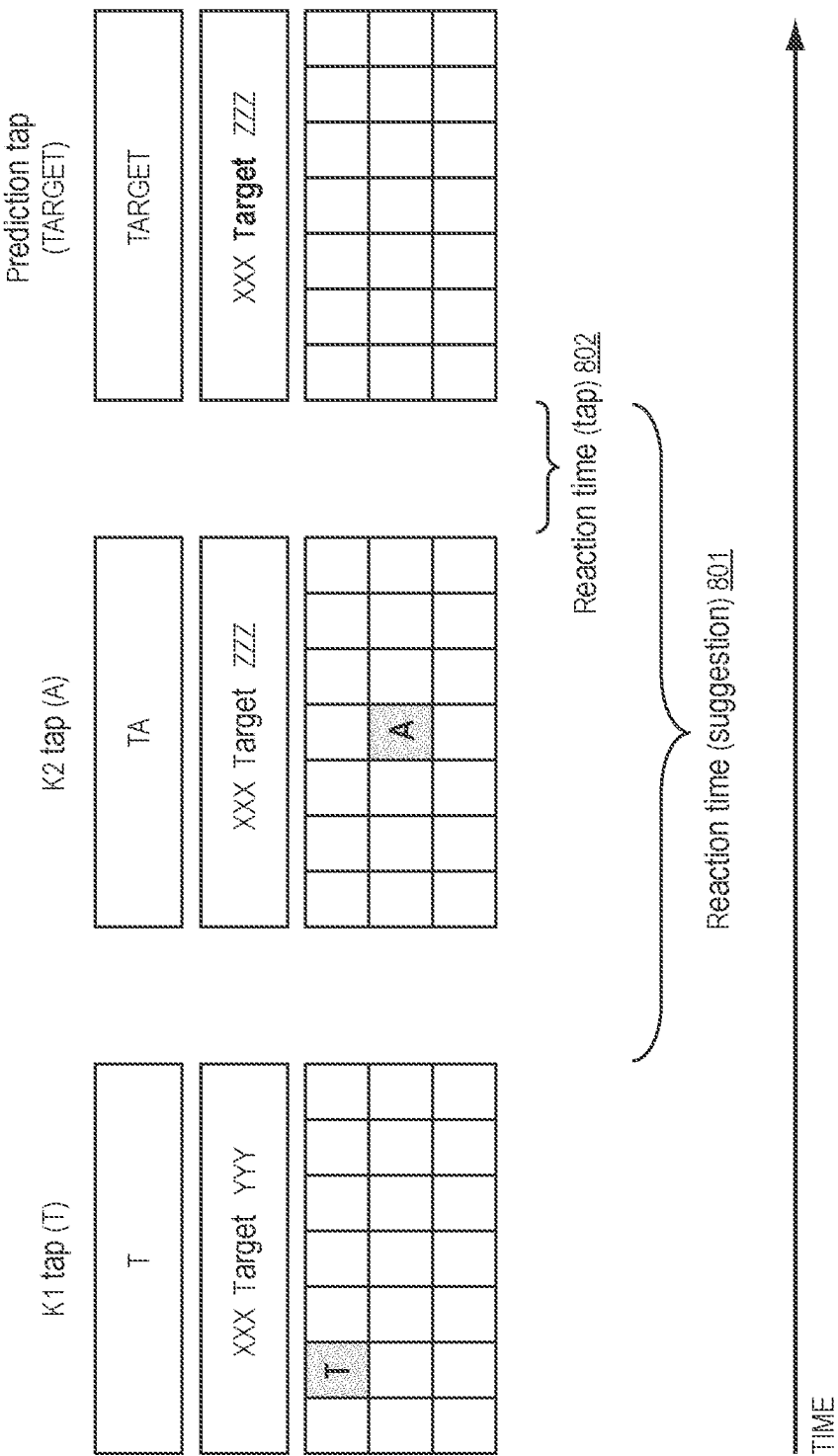
FIG. 8 illustrates reaction times to suggested words.

The enriched keystroke data may also include the user's reaction time to suggested text (e.g., where a display screen displays text which is suggested by a computer to complete a string of characters). For instance, the reaction time may be measured as the amount of time between when the suggestion is first displayed and when the user selects the suggestion (e.g., reaction time 801 in FIG. 8). Or, for instance, the reaction time may be measured as the amount of time between when the user releases the last keystroke before selecting the suggested text and when the user makes the selection (e.g., reaction time 802 in FIG. 8).

Sequences: The enriched keystroke data may also include n-grams. Each n-gram may describe a sequence of n consecutive items in a sample of typed text. For instance, an n-gram may consist of: (a) a sequence of key types of n consecutive keystrokes (e.g., alphanumeric-alphanumeric-punctuation-navigation-alphanumeric); (b) a sequence of transitions between keyboard zones for n consecutive keystrokes (e.g., a trajectory, such as zone 4→zone 2, zone 2→zone 6, in-zone); (c) a sequence of n consecutive hold times; (d) a sequence of n consecutive flight times; (e) a sequence of n consecutive delays; (f) a sequence of n consecutive zonal distances; (g) a sequence of data regarding typing precision for n consecutive keystrokes on a touchscreen; (h) a sequence of n consecutive pauses; (i) a sequence of n consecutive reaction times to suggested text, measured by amount of time between when the suggestion is first displayed and when the user selects the suggestion; (j) a sequence of n consecutive reaction times to suggested text, measured by amount of time between when the user releases the last keystroke before selecting suggested text and when the user makes the selection; (k) a sequence of n consecutive press times; (l) a sequence of n consecutive release times; (m) a sequence of n consecutive keyboard zones; (n) a sequence of data (e.g., timestamps) for n consecutive autocorrect events; or (o) a sequence of n consecutive key distances. The examples in the preceding sentence are not limiting; the enriched keystroke data may include other n-grams. In some sequences: (a) each item in the sequence is an attribute of a pair of consecutive keystrokes; and (b) the $n^{th}$ item in the sequence corresponds to the pair of keystrokes that starts with the $n^{th}$ keystroke. For instance, in some sequences: (a) flight time is an attribute of a pair of consecutive keystrokes; and (b) the $n^{th}$ flight time in the sequence is the flight time for the pair of consecutive keystrokes that starts with the $n^{th}$ keystroke.

A computer may label the sequences. Each label may identify a particular sequence, or identify a type of sequence. Grouping and/or labeling the data in sequences may facilitate detection of patterns in the data, because it may, in effect, change the level of analysis from individual items to sequences of items.

Windowing: The enriched keystroke data may also include data that has been separated into windows or bins of a pre-defined size. For instance, a computer may separate data into temporal windows of equal length (e.g., based on time of day or based on time elapsed since start of a typing session). Or, for instance, a computer may separate data into bins based on number of keystrokes (e.g., starting a new bin every one hundred keystrokes). Or, for instance, a computer may separate data into typing sessions (e.g., starting a new bin every time there is a change in the software or application where the typing stream is being generated).

Filtering: Enriched keystroke data may also be created by filtering. Among other things, the enriched keystroke data may include data that has been filtered by one or more attributes of keystroke(s) (or of data derived from keystrokes). For instance, a computer may create enriched keystroke data by filtering by any attribute that is specified in any augmented keystroke data or in any other enriched keystroke data. In some cases, a computer filters augmented keystroke data (and/or other enriched keystroke data) by one or more of the following attributes: time, keyboard zone, key type, context, hold time, flight time, delay, trajectory, and reaction time. In some cases, a computer filters n-grams by one or more of the foregoing attributes or by one or more n-gram labels. When filtering by an attribute, a computer may either: (a) select only data with that attribute or combination of attributes; or (b) exclude data with that attribute or combination of attributes.

As noted above, all or part of the enriched keystroke data may be calculated based on key-anonymized augmented data that does not include the identity of specific alphanumeric keystrokes. For instance, a computer may derive, from key-anonymized augmented data, each of the following: hold time, flight time, delay, distance, trajectory and pauses.

However, in some cases, all or part of the enriched keystroke data is calculated based on a key-identifying stream. Put differently, in some cases, at least a portion of the enriched keystroke data is derived from a data stream that specifies the identity of alphanumeric characters (e.g., specifies that the user has typed a lower case "s").

For instance, the following two types of enriched keystroke data may be calculated based at least in part on a key-identifying stream: (a) syntax/semantics; and (b) distance between individual keys. We now discuss each of these in turn.

Syntax/Semantics: The data regarding syntax or semantics may be generated by a natural language processing (NLP) program. For instance, a computer may perform an NLP program which: (a) takes a key-identifying stream as an input and (b) outputs data regarding syntax or semantics of text encoded by the key-identifying stream. The data regarding syntax may include at least: (a) a vector that lists the number of letters in each respective word of the text; (b) a frequency dictionary that lists the number of times that each word in the text appears; and (c) a parse tree (also known as a syntax tree). For instance, the NLP program may output a dependency-based parse tree or a constituency-based parse tree. In some cases, in order to analyze the syntax of text typed by a user, the NLP program performs at least tokenization, part-of-speech tagging, dependency parsing, constituency parsing, and lemmatization (or stemming), and stopword removal. Alternatively, at least part of the data regarding syntax may be calculated based on anonymized augmented keystroke data.

Figure 7:
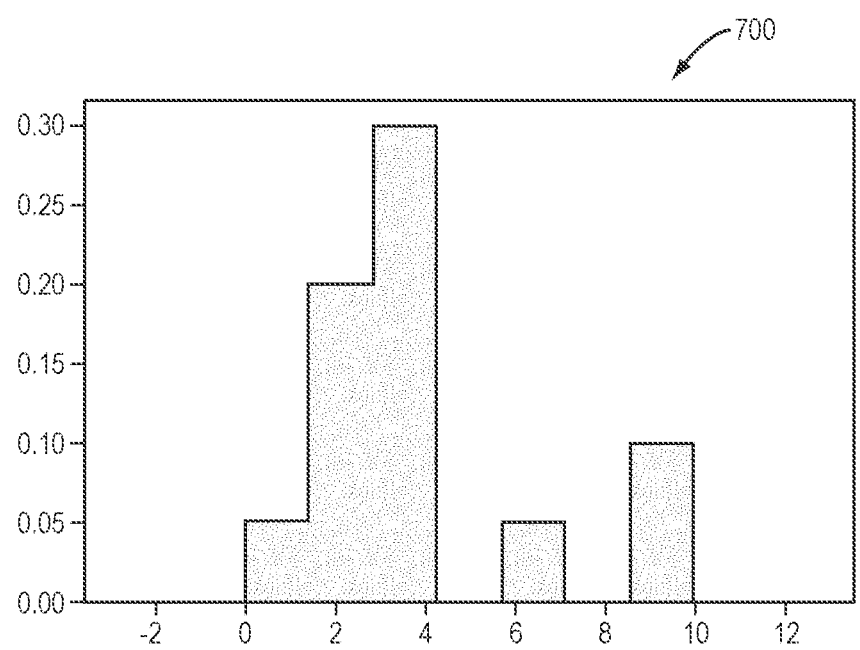
FIG. 7 is a histogram of a distribution of word lengths.

FIG. 7 is a histogram 700 that illustrates a distribution of word lengths during a typing session.

Key Distance: Likewise, a distance (which is included in enriched keystroke data) may be calculated based on distance between individual keys, rather than between keyboard zones. We sometimes call this "key-specific distance". Key-specific distance may be calculated from a key-identifying stream. For each pair of consecutive keystrokes, the key-specific distance may be indicative of a relative or absolute physical distance between: (a) a point in a first key pressed in the first keystroke and (b) a point in a second key pressed in the second keystroke. If both keystrokes are at the same key, the key-specific distance may be zero. The key-specific distance may be distance in a single dimension along an axis of the keyboard that is parallel to a row or column of keys (e.g., in a QWERTY keyboard, a row of keys that includes Q, W, E, R, T, Y, U, I, O and P). Alternatively, the key-specific distance may be a distance in two dimensions (e.g., in the case of a flat keyboard or flat touchscreen) or in three dimensions (e.g., in the case of a curved keyboard, as in some ergonomic keyboards). The key-specific distance may be an unsigned number. Alternatively, a keyboard may be represented by an array of "rows" and "columns" and key-specific distance may be expressed as distance between elements of the array.

Alternatively, for each pair of consecutive keystrokes, a key-specific distance (which is included in the enriched keystroke data) may be a signed number that indicates spatial position of the first key (where the first keystroke occurs) relative to the second key (where the second keystroke occurs). For instance, in cases in which the keyboard zones change as displacement along a right-left axis of the keyboard changes (as shown in FIG. 3), a key-specific distance may be a signed number that indicates whether the first key is to the right or to the left of the second key.

Augmented keyboard data may be calculated: (a) by a server computer that is remote from a client computer; (b) by one or more client computers; or (c) partly by a server and partly by one or more client computers. The client computer may be housed in a smartphone or other mobile computing device. Alternatively, the client computer may be a laptop or other personal computer that includes or is attached to a keyboard.

In some cases: (a) one or more client computers send key-anonymized augmented data to a server; and (b) the server calculates, based on this key-anonymized data, all or part of the enriched keystroke data. In this approach, the server may never learn the alphanumeric keystrokes that underlie the key-anonymized data.

In some cases, one or more client computers: (a) take, as an input, key-anonymized augmented data; (b) calculate, based on this key-anonymized data, all or part of the enriched keystroke data; and (c) send the enriched keystroke data to a remote server computer. Again, in this approach, the server may never learn the alphanumeric keystrokes that underlie the key-anonymized data.

In some cases, one or more client computers: (a) take, as an input, a key-identifying stream that represents text typed by a user; (b) output data regarding key-specific distance and regarding syntactic structure of the text; and (c) send this data (regarding key-specific distance and syntactic structure) to a remote server. In this approach, the server may never learn the alphanumeric keystrokes that are included in the key-identifying stream.

In some cases, all or some of the enriched keystroke data is normalized, standardized, shifted, rescaled, or clipped.

Keystroke Tensors

A computer may create one or more variable-sized data structures. Each of these variable-sized data structures may include or consist of: (a) augmented keystroke data; (b) enriched keystroke data; or (c) both augmented keystroke data and enriched keystroke data. We sometimes call such a variable-sized data structure a "keystroke tensor".

In some cases, a computer calculates a separate keystroke tensor for each typing session of a user.

In some cases, a keystroke tensor is: (a) a nested, variable-length list whose elements may include, among other things, one or more other nested, variable-length lists; (b) a nested, variable-length data structure whose elements may include, among other things, one or more other nested, variable-size data structures; (c) a ragged tensor, as that term is used in the TensorFlow® programming language; (d) a variable-size data structure, such as a dynamic array, growable array, resizable array, dynamic table, mutable array, or array list; (e) a nested, variable length list (e.g., in the R programming language, Python® programming language, or Julia® programming language); (f) any other nested, variable-sized matrix, table, array or vector; (g) any dynamically-sized, nested associative array (such as a dictionary in the Python® programming language); or (g) any other data structure, including any list, vector, array, or matrix. In some cases, a keystroke tensor may include different types of elements (e.g., scalar, vectors, matrices or lists) or data types (e.g., numeric, text, sequence, map, set, Boolean, binary or object data types).

In some cases, keystroke tensors are calculated by successive transformations of keystroke data. For instance, in some cases, one or more computers: (a) receive, from a keyboard or touchscreen, a key-identifying stream of data for a typing session; (b) transform the key-identifying stream into a first keystroke tensor of augmented keystroke data; and (c) then transform the first keystroke tensor into a second keystroke tensor which consists of enriched keystroke data. Alternatively, different types of enriched keystroke data or augmented keystroke data may be computed separately by successive transformations of data and then combined into a keystroke tensor.

As noted above, a separate keystroke tensor may be calculated for each typing session of a user, and a keystroke tensor may include or consist of: (a) augmented keystroke data; (b) enriched keystroke data; or (c) both augmented keystroke data and enriched keystroke data. For instance, a keystroke tensor may include: (a) two or more types of augmented keystroke data (e.g., press time and release time); (b) two or more types of enriched keystroke data (e.g., flight time and delay); or (c) both two or more types of augmented keystroke data and two or more types of enriched keystroke data.

As a non-limiting example, in some use scenarios, a computer calculates a keystroke tensor $S_I$ for the $I^{th}$ typing session of a user as follows:

$$S_I = \{P_{k_n}^I, R_{k_n}^I, Z_{k_n}^I, E_{k_n}^I, T_{k_n}^I, A_e^I, W_e^I, C^I\} \quad \text{(Eq. 4)}$$

where I identifies the $I^{th}$ typing session, $k_n$ is the $n^{th}$ keystroke during the typing session, P is press time, R is release time, Z is keyboard zone where the keystroke occurs, E is tap precision, T is key type, A is an autocorrect event, W is user selection of computer-suggested text, C is typing session context, and the subscript e indicates the $e^{th}$ occurrence during a typing session.

For instance, in Equation 4: (a) $P_{k_7}^2$, would be the press time for the seventh keystroke during the second typing session; (b) $A_4^5$ would specify information (e.g., timing) regarding the fourth autocorrect event during the fifth typing session; and (c) $W_6^3$ would specify information (e.g., timing) regarding the sixth user selection of a computer-suggested word or phrase during the third typing session.

If a term on the right-hand side of Equation 4—such as A (autocorrect event), W (user-selection of computer-suggested text), or E (tap precision)—does not apply to a particular typing session, then it may be omitted from Equation 4 for that particular typing session. For instance, for some types of mechanical keyboards: (a) data regarding A (autocorrect event) and W (user-selection of computer-suggested text) is not collected; and (b) those terms may be omitted from Equation 4. Likewise, in Equation 4, E (tap precision) applies only if the user is typing on a touchscreen during the typing session. If the user is not typing on a touchscreen during the session, then E may be omitted. In some cases, E specifies an x-component and a y-component of a vector that: (a) terminates at a point of contact of the user's finger on the screen; and (b) originates at a point of the screen where a portion of a key is being displayed. In other words, in some cases, $E_{k_n} = \{E_{k_{n_x}}, E_{k_{n_y}}\}$.

In Equation 4, the keystroke tensor $S_I$ for a typing session I includes elements for each value of n (i.e., for each keystroke) and each value of e that occur in that typing session.

In Equations 4 and 5, $C^I$ may be a list or vector that provides information about the context of the g h typing session of a user. For instance, in some cases, $C^I = \{C_{START}^I, C_{SOFT}^I, C_{HARD}^I, C_{STATE}^I,\}$, fit where (a) I identifies the typing session, (b) START is the start time of the session; (c) SOFT identifies a software application that is hosting the session; (d) HARD identifies hardware that is measuring the keyboard events during the session (e.g., the model of keyboard or touchscreen that is being employed for the typing); and (e) STATE is a state, during the session, of the device measuring the keystrokes during the session.

As another non-limiting example, in some use scenarios, a computer calculates a keystroke tensor $S_I$ for the $I^{th}$ typing session of a user as follows:

$$S_I = \{HT_n^I, FT_n^I, DL_n^I, ZD^I, TR^I, C^I\} \quad \text{(Eq. 5)}$$

where I identifies the $I^{th}$ typing session, $k_n$ is the $n^{th}$ keystroke during the typing session, $HT_n$ is hold time of the $n^{th}$ keystroke, $FT_n$ is flight time for the pair of keystrokes that starts with the $n^{th}$ keystroke, $DL_n$ is delay for the pair of keystrokes that starts with the $n^{th}$ keystroke, $ZD^I$ is zonal distance for a sequence of keystrokes in the typing session, $TR^I$ is trajectory for a sequence of keystrokes in the typing session, and C is typing session context.

For instance, in Equation 5: (a) $HT_{19}^7$ would be the hold time for the nineteenth keystroke during the seventh typing session; and (b) $FT_4^5$ would be the flight time for the pair of keystrokes starting with the fourth keystroke in the fifth typing session.

In Equation 5, the keystroke tensor $S_I$ for a typing session I includes elements for each value of n (i.e., for each keystroke) that occurs in that typing session.

In Equation 4, the keystroke tensor consists of augmented keystroke data but does not include enriched keystroke data. In Equation 5, the keystroke tensor consists of enriched keystroke data but does not include augmented keystroke data.

Equations 4 and 5 describe non-limiting examples of keystroke tensors. Other keystroke tensors may be calculated. For instance, the number and types of elements of a keystroke tensor may be different than as shown in Equations 4 and 5.

Alternatively, a keystroke tensor may consist partially or solely of: (a) untransformed data from a key-identifying stream; and/or (b) data from a key-identifying stream that has not undergone any transformation other than, to the extent applicable, adding timestamp(s). In this alternative approach, the content of the typed text may be included in, or easily extracted from, the keystroke tensor.

As used herein, a "key-specifying tensor" means a keystroke tensor that includes: (a) untransformed data from a key-identifying stream; and/or (b) data from a key-identifying stream that has not undergone any transformation other than, to the extent applicable, adding timestamp(s).

As used herein, an "augmented keystroke tensor" means a keystroke that includes augmented keystroke data and that may include other types of data, except enriched keystroke data. Thus, if a keystroke tensor includes enriched keystroke data, then it is not an "augmented keystroke tensor", as that term is used herein.

As used herein, an "enriched keystroke tensor" means a keystroke tensor that includes enriched keystroke data and that may include other types of data, such as augmented keystroke data. For instance, an "enriched keystroke tensor" for a typing session may include, among other things, data regarding the context of the session (e.g., session start time, software, hardware and state, as discussed above).

In some cases, all or some of the data in a keystroke tensor is normalized, standardized, shifted, rescaled, or clipped.

Features

In illustrative implementations of this invention, one or more computers calculate features that are then fed as input into one or more machine learning algorithms.

To calculate these features, one or more computers may transform a dataset. We sometimes call this dataset (before it is transformed) an "interim dataset". Put differently, a computer may take an interim dataset as input, may transform it, and may output features. In some cases, the interim dataset comprises one or more enriched keystroke tensors. In some cases, the interim dataset comprises one or more augmented keystroke tensors. In some cases, the interim dataset comprises one or more enriched keystroke tensors and one or more augmented keystroke tensors. In some cases, the interim dataset consists of or includes one or more key-specifying tensors. In some cases, the interim dataset comprises any combination of enriched keystroke tensor(s), augmented keystroke tensor(s), and/or key-specifying tensors. In some cases, the interim dataset comprises any combination of enriched keystroke data, augmented keystroke data, data from a key-identifying stream, or raw data. In some cases, the interim dataset comprises: (a) data regarding keystrokes; and/or (b) data derived from data regarding keystrokes. In some cases, data in the interim dataset is organized into one or more data structures, such as any list, vector, array, or matrix. These data structures in the interim dataset may be variable-length, variable-sized, fixed-length or fixed-size, and may be nested or un-nested.

At least some of the features (which are fed into the machine learning algorithm(s)) may be created by performing an autoencoder or dimensionality reduction algorithm.

Autoencoder: In some cases, one or more computers employ autoencoder(s) to transform the interim dataset into features. For instance, each autoencoder that performs or helps to perform the transformation may comprise: (a) a neural network that is trained to minimize a difference between its output and its input; (a) a feed-forward, non-recurrent network that is trained to trained to minimize a difference between its output and its input; (c) an under-complete autoencoder (whose output has a lower dimensionality than its input); (d) a regularized autoencoder; (e) a sparse autoencoder, (f) a denoising autoencoder; (g) a contractive autoencoder, or (h) a variational autoencoder. Each autoencoder may transform the interim dataset in such a way as to regularize, to minimize noise in, to minimize redundancy in, and/or to reduce the dimensionality of, data in the dataset.

Dimensionality Reduction: In some cases, one or more computers transform the interim dataset into features by performing a dimensionality-reduction algorithm. For instance, the dimensionality-reduction algorithm may comprise principal component analysis (PCA), non-negative matrix factorization, kernel PCA, graph-based kernel PCA, linear discriminant analysis, generalized discriminant analysis, t-distributed stochastic neighbor embedding, UMAP (uniform manifold approximation and projection) or (as noted above) an autoencoder. The dimensionality-reduction algorithm may output a set of features (e.g., principal components) that has a lower dimensionality than the interim dataset.

Heuristically-Selected Features: Alternatively, at least some of the features (which are fed into the machine learning algorithm(s)) may be created by performing statistical calculations that have been previously selected by a human. For instance: (a) a human may heuristically select a set of descriptive and/or inferential statistics; (b) a computer program may be written to calculate this set of descriptive and/or inferential statistics; and (c) a computer may execute this program and output this set of descriptive and/or inferential statistics, which in turn may be employed as features that are fed into one or more machine learning models.

Descriptive Statistics: In some cases, one or more computers transform at least part of the interim dataset into features by calculating descriptive statistics. These descriptive statistics may summarize data in the interim dataset. For instance, the descriptive statistics may summarize augmented keystroke data and enriched keystroke data. As a non-limiting example: (a) a computer may calculate descriptive statistics for one or more types of augmented keystroke data or enriched keystroke data, which descriptive statistics include any one or more measures of central tendency (e.g. mean, mode, median, average of medians), measures of dispersion (e.g. variance, standard deviation, quartiles, quantiles), measures of asymmetry or outliers (e.g. skewness, kurtosis), measures of statistical distance, difference or similarity (e.g., Bhattacharyya distance or f-distance), probability distributions for discrete variables (e.g., probability function, probability mass function, frequency distribution, relative frequency distribution, discrete probability distribution function, categorical distribution), probability distributions for continuous variables (e.g., probability density function, continuous probability distribution function, cumulative distribution function, cumulative distribution function, quantile distribution function), and measures of range, heteroskedasticity, statistical dependence and/or correlation; and (b) these descriptive statistics may be included in features that are fed as input into one or more machine learning algorithms. The descriptive statistics (which are employed as features) may be univariate or multivariate. For instance, if multivariate descriptive statistics are used as features, they may include cross-tabulations, contingency tables, scatterplots, quantitative measures of dependence (e.g., Pearson correlation coefficient or Spearman's rank correlation), and/or conditional distributions.

Here are three non-limiting examples of descriptive statistics that may be used as features. (1) The average, standard deviation, skewness and kurtosis of hold times for space key keystrokes may be calculated and may be fed, as features, into a machine learning model. (2) Either the full series or intervals of the primitive typing signals may be transformed by estimating the corresponding probability distributions. This process may apply histogram-based analysis or kernel density estimation to calculate the underlying probability density function of the signal or signal portion. Sampled representations of the density signals may be used as engineered features themselves (e.g., the values of four bin histogram representation of the distribution of flight times measured in transition between words). (3) Metrics of statistical distance may also be used to generate features that represent the distance or degree of similarity between two distributions of the same primitive signal (e.g. f-divergence measured between the distribution of keystroke delays measured on a given day and the following day) or two different signals (e.g. Bhattacharyya distance between the distributions of flight times in key transitions between words versus transitions within words).

Inferential Statistics: In some cases, one or more computers transform at least part of the interim dataset into features by calculating inferential statistics. These inferential statistics may make inferences from augmented keystroke data or enriched keystroke data. For instance: (a) a computer may take at least part of the augmented keystroke data or enriched keystroke data as input, and may then perform—with respect to the inputted data—any statistical inference algorithm such as t-test, F-test, regression analysis, ANOVA (analysis of variance) ANCOVA (analysis of covariance), MANOVA (multivariate analysis of variance), MANCOVA (multivariate analysis of covariance), factor analysis, multidimensional scaling, cluster analysis, discriminant function analysis, or other multivariate analysis; and (b) the resulting inferential statistics may be included in the features that are fed into one or more machine learning algorithms. For instance, the features calculated by inferential statistics may include an interval estimate (e.g., a confidence interval or set estimate), a point estimate (e.g., a particular value that approximates a parameter), a credible interval, or a clustering or classification of data points into groups. The statistical model employed in calculating the inferential statistics may be fully parametric, non-parametric or semi-parametric.

In some cases, the features that are fed into the machine learning algorithm(s) are calculated by any combination of one or more of the above approaches (e.g., autoencoder, dimensionality reduction, descriptive statistics, inferential statistics). For instance, the features may include: (a) one or more outputs of autoencoder(s); (b) one or more outputs of dimensionality reduction algorithms (e.g., principal components); (c) one or more descriptive statistics; and/or (d) one or more inferential statistics.

The inputs to a calculation (which is performed to calculate one or more features) may consist of only a particular type of data (e.g., a particular type of augmented keystroke data or of enriched keystroke data). Alternatively, the inputs to a calculation (which is performed to calculate one or more features) may comprise multiple types of data (e.g., multiple types of augmented keystroke data and/or of enriched keystroke data). As non-limiting examples: (a) a feature may be a statistical characterization of the distribution of flight times generated in a given typing session (single feature category); or (b) another feature may be a distribution of flight times filtered by linguistic unit (multiple feature categories).

In some cases, the features that fed into the machine learning algorithm(s) are derived from, or included in, one or more of the following primitive feature families: Keystroke, Location, Pauses, Syntax/Semantics, Precision and Text Prediction.

Examples of primitive signals in the Keystroke family include hold time (time between pressing and releasing a key), flight time (time between press events for two consecutive keys), and delay (e.g., measurements of interdigit coordination computed as overlap between press-release events in sequential keys). Features that are derived from primitive signals in the Keystroke family may include, among other things: (a) IQR of hold time in a typing window unit; (b) heteroskedasticity of normalized flight time series; and (c) rate of overlap between consecutive keys within a typing unit. IQR is discussed below. It may be helpful to use IQR of hold time in a typing window unit as a feature, because fine motor decline may affect consistency of hold time values over time. This may generate wider distributions resulting in larger interquartile ranges. It may be helpful to use heteroskedasticity of normalized flight time series as a feature, because fine motor decline may affect finger rhythmicity and coordination during a typing session. This may result in unequal levels of variability and different ranges of the flight time domain when comparing consecutive typing intervals. It may be helpful to use rate of overlap between consecutive keys within a typing unit as a feature, because fine motor decline may cause episodic micro-freezing events while typing. This in turn may affect fingers' ability to release a key, resulting in a larger rate of overlapping keystroke within a typing session.

Examples of primitive signals in the Location family include location-based signals (e.g., measurements of interdigit/asymmetric finger performance computed as a statistical comparison of the timing metrics for different keyboard zones). Features that are derived from primitive signals in the Location family may include, among other things, difference in median hold time measured in right-sided versus left-sided keystrokes. It may be helpful to use this difference as a feature, because asymmetry in motor decline or in cognitive impairment may result in greater differences between timing performance of the right- and left-hand fingers as compared to normal variability introduced by natural hand dominance. Similarly, different executive processes governing bimanual versus single hand transitions may reflect different patterns in the location-based data in users with impaired motor or cognitive performance.

Examples of primitive signals in the Pauses family include a pause in a word, a pause between words, a pause between sentences, a pause involving a special key, and a pause involving multiple or single backspaces. Features that are derived from primitive signals in the Pauses family may include, among other things, an average/median of normalized delay between language unit events. It may be helpful to use this average or median as a feature, because cognitive decline may affect memory, which may result in larger values in time breaks within words (e.g., because a user has difficulty in remembering the position of a specific key) or between words (e.g., slowed word-finding).

Examples of primitive signals in the Syntax/Semantics family include semantic analysis (such as measurements of word length distribution and complexity) and syntactic analysis (such as measurements of sentence length distribution and complexity). Features that are derived from primitive signals in the Syntax/Semantics family may include, among other things: (a) rate of words with a length equal or above six characters; and (b) average and median number of words per sentence. It may be helpful to use rate of words with a length equal or above six characters as a feature, because cognitive decline may cause difficulties with lexical processing. These difficulties may cause a decreased rate of longer words. It may be helpful to use average/median number of words per sentence as a feature, because cognitive decline may affect the degree of syntactic complexity in natural language, which may manifest as reduced number of words per sentence in cognitively impaired users.

Examples of primitive signals in the Precision family include backspace (e.g., rate of backspace events and correlation with precision/keyboard zone metrics in preceding keys) and autocorrect (e.g., a time series of autocorrect events). Features that are derived from primitive signals in the Precision family may include, among other things: (a) rate of single backspace versus a series of multiple consecutive backspaces; and (b) standard deviation of rate of autocorrect events normalized by time of the day. It may be helpful to use rate of single backspace versus multiple backspace as a feature, because single backspace events may appear more often when finger movement precision is affected, while multiple consecutive backspace events may indicate impaired attention. A single backspace rate may tend to be higher for users with motor impairment than for cognitively impaired users, while multiple consecutive backspace rate may tend to be higher for cognitively impaired users than for users with motor impairment. It may be helpful to use standard deviation of rate of autocorrect events normalized by time of day as a feature, because a sustained high rate of autocorrect events at all times may indicate impaired fine motor precision and/or attention deficit. In some use scenarios in which touchscreen typing is employed, a primitive signal may measure or be derived from tap precision. For instance, the primitive signal may be distance between a touch event and the position of the center of the target key for that touch event (e.g. average touch-target distance, standard deviation of the touch-target distance, or average touch-target distance by key zone).

Examples of primitive signals in the Text Prediction family include word prediction (e.g., a time series of prediction tap events). Features that are derived from primitive signals in the Text Prediction family may include, among other things, the number of keys preceding selection of the predicted text. This number of keys may be normalized. It may be helpful to use this number of keys (or normalized number of keys) as a feature, because noticing the target word earlier in the prediction engine may indicate enhanced attention, which may be negatively correlated with cognitive impairment.

The features that are fed into machine learning algorithm(s) may include one or more: (a) primitive signals described in the preceding seven paragraphs; or (b) one or more features derived from those primitive signals. One or more of the features that are fed into the machine learning algorithm(s) may be normalized, standardized, shifted, rescaled, or clipped.

In some cases, the features that are fed into ML algorithm(s) include values of one or more functional states of a user.

Figure 9:
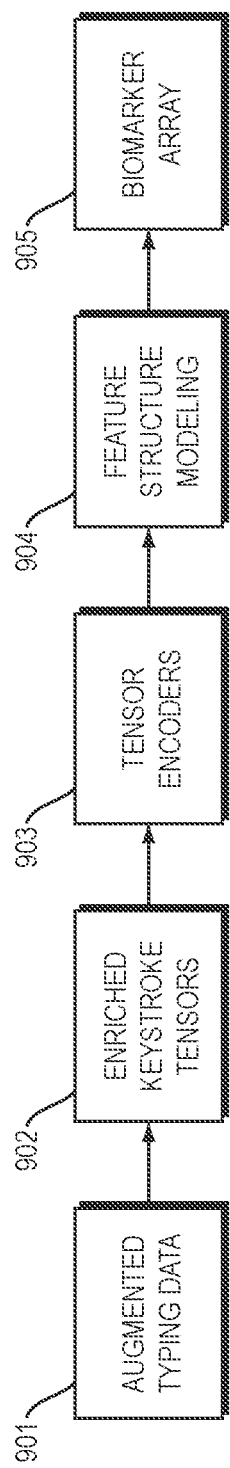
FIG. 9 is a flowchart of a method in which, among other things, a tensor encoder creates features.

FIG. 9 is a flowchart of a method in which, among other things, a tensor encoder creates features. In FIG. 9, the method includes at least the following steps: Calculate augmented typing data (Step 901). Calculate enriched keystroke tensors (Step 902). Perform tensor encoding (Step 903) and feature structure modeling (Step 904). Generate biomarker array (Step 905).

Machine Learning

The features may be fed as input into one or more machine learning algorithms, which in turn may calculate an assessment of one or more health conditions or functional states of a user.

In some implementations of this invention, one or more machine learning algorithms are employed to calculate, based on the inputted features, an assessment of one or more health conditions or functional states of a user. For instance, the one or more machine learning algorithms may comprise one or more: regression algorithms (e.g. linear regression); instance-based algorithms (e.g. k-nearest neighbors, kernel machines, or radial basis function algorithms); regularization algorithms (e.g. ridge regression); decision tree algorithms; Bayesian algorithms (e.g. naive Bayes, Gaussian naive Bayes, multinomial naive Bayes, or Bernoulli naive Bayes); clustering algorithms (e.g. k-means); random forests algorithms; ANNs (artificial neural networks); CNNs (convolutional neural networks); RNNs (recurrent neural networks); RNNs with LSTM (long short term memory) algorithms; RNNs with Gated Recurrent Unit; MLPs (multi-layered perceptrons); SVMs (support vector machines); deep learning algorithms; ensemble machine learning algorithms; reinforcement learning algorithms (such as a Monte Carlo, Q-learning, state-action-reward-state-action, or deep Q network algorithm); AEs (auto-encoders), SAEs (stacked auto-encoders) VAEs (variational auto-encoders), DBNs (deep belief networks), GANs (generative adversarial networks), conditional GANs, infoGANs; or restricted Boltzmann machines. The one or more machine learning algorithms may perform supervised or unsupervised learning.

If one or more supervised machine learning algorithms are employed, they may perform supervised training in which they train on labeled data. For instance, the labels for the labeled data may be based on clinical diagnosis results (e.g., diagnoses made by human medical professionals), results from medical tests, (e.g. PET scans), results of clinical scales for cognitive or functional performance, or results from other monitoring systems. The data used to train the models may be collected during controlled clinical trials (e.g., clinically characterized cohorts) or from self-reported clinical state (e.g., where a user reports his or her state). In some cases, the user self-reports may be crowd-sourced. In some use scenarios, the same dataset is used to train and evaluate the models using cross validation. In other use scenarios, a hold-out approach with fully independent training and testing sets is employed.

In some cases, an ensemble of machine learning models take, as an input, features that encode or are derived from one or more streams of augmented typing data. In some cases, an ensemble of machine learning models outputs an assessment of one or more health conditions or functional states. This assessment may consist of the output of one of the models included in the ensemble or may instead comprise a combination of outputs of multiple model outputs in the ensemble.

Biomarker Array

As noted above, the one or more machine learning algorithms: (a) may take features as inputs; and (b) may output an assessment of one or more health conditions or functional states of a user. Each health condition that is assessed may be a disease or a symptom of a disease.

For instance, the machine learning algorithm(s) may assess the presence, severity or probability of, or a change in, one or more symptoms such as: mild cognitive impairment; dementia; impairment of fine motor control; impairment of sensory-motor feedback; or behavioral impairment.

Or, for instance, the machine learning algorithm(s) may assess the presence, severity or probability of, or a change in, one or more diseases, such as: Alzheimer's disease; mild cognitive impairment; dementia with Lewy bodies, Parkinson's disease; multiple sclerosis; frontotemporal degeneration; Huntington's disease; Lewy body disease; prion disease; HIV/AIDS; carpal tunnel syndrome; osteoarthritis; psoriatic arthritis; rheumatoid arthritis; peripheral nerve disorders (e.g., Charcot-Marie-Tooth disease, chronic inflammatory demyelinating polyneuropathy, or amyloidosis), spine disease (such as spondylosis or myelopathies); and/or brain diseases (such as amyotrophic lateral sclerosis, frontotemporal dementia, other motor-neuron disease, stroke, and dystonia).

Or, for instance, the machine learning algorithm(s) may assess the etiology of a particular symptom (e.g., may distinguish between Parkinson's dementia and dementia with Lewy bodies).

Or, for instance, the machine learning algorithm(s) may assess one or more functional states of a user or changes in such functional state(s). For instance, the functional states may include states of one or more cognitive, motor, or behavioral functions and/or states of any one or more subfunctions thereof (e.g., attention, verbal memory, non-verbal memory, or coordination).

As noted above, the machine learning (ML) algorithm(s) may output an assessment of one or more health conditions or functional states of a user. In some cases, this assessment is at least temporarily stored, or outputted, in a data structure such as an array, matrix, vector or list. This data structure may include one or more elements. We sometimes call the information which is outputted by the ML algorithm(s) a "biomarker array".

In some cases, the ML algorithm(s) output a biomarker array that includes, for each condition (e.g., health condition or functional state) that is assessed, one or more of the following: (a) a binary indicator of the presence or absence of the condition; (b) a categorical indicator of the condition (or of a group of conditions to which it belongs); (c) a numeric representation of the probability of the presence of the condition; (d) a numeric representation of the degree of severity of the condition; (e) a numeric representation of the degree of similarity of an input typing pattern to a typing pattern that is positively correlated with the condition; (g) a numeric representation of a clinically significant change between two given time points in functional performance related to the condition; and (h) a numeric representation of the probability of the presence of a clinically significant change between two given time points in functional performance related to the condition. For instance, a condition in the preceding sentence may comprise cognitive impairment, mild cognitive impairment, dementia, impairment of fine motor control, impairment of sensory-motor feedback, behavioral impairment, Alzheimer's disease, Parkinson's disease, multiple sclerosis, any other disease or symptom that is mentioned in this section titled "Biomarker Array", or any functional state that is mentioned in the section below titled "Functional States".

In some cases, the ML algorithm(s) output a biomarker array that includes one or more biomarkers. Each of the biomarkers may characterize or identify a disease, characterize, identify or quantify a symptom of a disease, characterize, identify or quantify impairment due to a disease, or characterize, identify or quantify a functional state. Each of these biomarkers may describe or quantify a condition as of a specific time, specific day, or specific window of time. For instance, a biomarker (which is outputted by the ML algorithm(s)) may quantify cognitive impairment that exists on a particular date or at a particular time. Or, for instance, a biomarker may quantify a functional state on a particular date or at a particular time. Alternatively, a biomarker (which is outputted by the ML algorithm(s)) may describe or quantify a change or pattern of change of a condition over time. For instance, a biomarker may quantify a change, over time, in cognitive impairment or in a functional state.

In some cases, the ML algorithm(s) output a biomarker array that includes one or more biomarkers which are normalized, standardized, shifted, rescaled, or clipped. For instance, one or more biomarkers that are indicative of severity of impairment (or of severity of symptom) may be normalized to a range of [0,1], where zero represents healthy normal and one represents a maximum deviation from the healthy.

Functional States

In some implementations of this invention, machine learning algorithm(s) assess one or more functional states of a user, based on data that represents or is derived from measurements of typing by the user. Put differently, in some implementations, ML algorithm(s) assess one or more functional states of a user, based on data that represents or is derived from measurements of typing by the user (e.g., data regarding or derived from keystrokes or keystroke events). The functional states which are assessed may include state(s) of one or more of: (a) motor function, (b) cognitive function; (c) behavioral function; or (d) one or more sub-functions of any of the foregoing. For instance, these sub-functions may include: (a) aspects of motor function, such as balance, reaction time, physical strength, body awareness, coordination, tremor, speech, facial expression, agility, gait, motion fluidity, respiratory quality, dexterity, bilateral hand coordination, right hand coordination, left hand coordination, steadiness, precision, general velocity, and seasonality of motor stability; (b) aspects of cognitive function, such as central processing, executive function, complex attention, nonverbal memory, language/verbal skills, social cognition, visual motor ability, processing speed, attention and concentration, perception, sensation, visuospatial function, verbal memory, mental tracking, and mental monitoring; and (c) aspects of behavioral function, such as mood, social interactions and behavioral control. The ML algorithm(s) may assess one or functional states of a user who is healthy, impaired or ill.

In order to train the ML algorithm(s) to assess the one or more functional states, the ML algorithms may be trained on training data which: (a) measures or is derived from keystrokes; and (b) has been labeled with values of one or more functional states.

The training labels (which specify values of functional states) may be computed based on score(s) on scale items of one or more clinical scales. Put differently, these training labels may be derived from users' scores on scale items of one or more clinical scales. For example, the clinical scale(s) which are used to derive these training labels may include one or more of the following clinical tests: Activities of Daily Living (ADL); Amyotrophic Lateral Sclerosis Cognitive Behavioral Screen (ALS-CBS); Amyotrophic Lateral Sclerosis Functional Rating Scale (ALSFRS); Clinical Assessment of Behavior (CAB); Clinical Dementia Rating (CDR); Dementia Rating Scale 2 (DRS-2); Frontal Assessment Battery (FAB); Functional Gait Questionnaire (FGQ); Freezing of Gait Questionnaire (FOGQ); Judgement of Line Orientation (JLO); Unified Parkinson's Disease Rating Scale Part I (MDS-UPDRS-I); Unified Parkinson's Disease Rating Scale Part II (MDS-UPDRS-II); Unified Parkinson's Disease Rating Scale Part III (MDS-UPDRS-III); Unified Parkinson's Disease Rating Scale Part IV (MDS-UPDRS-IV); Mini-Mental Status Examination (MMSE); Montreal Cognitive Assessment (MoCA); Multiple Sclerosis Functional Composite (MSFC); Multiple Sclerosis Performance Test (MSPT); Non-Motor Symptoms Scale for Parkinson's Disease (NMSS); Neuropsychiatric Inventory (NPI); Neuropsychiatric Inventory Questionnaire (NPI-Q); Purdue Pegboard Test (PPBT); Trail Making Test (TMT); and any other clinical scale that is used to assess neurological or neurodegenerative disease or to assess symptoms of such a disease.

Each clinical scale that is used to derive these training labels (which specify values of functional states) may itself include multiple scale items. For instance: (a) the ADL includes 6 scale items; (b) the ALS-CBS includes 24 scale items; (c) the ALSFRS includes 11 scale items; (d) the CAB includes 7 scale items; (e) the CDR includes 6 scale items; (f) the DRS-2 includes 5 scale items; (g) the FAB includes 6 scale items; (h) the FGQ includes 16 scale items; (i) the FOGQ includes 6 scale items; (j) the JLO includes 1 scale item; (k) the MDS-UPDRS-I includes 13 scale items; (l) the MDS-UPDRS-II includes 13 scale items; (m) the MDS-UPDRS-III includes 35 scale items; (n) the MDS-UPDRS-IV includes 6 scale items; (o) the MMSE includes 10 scale items; (p) the MoCA includes 15 scale items; (q) the MSFC includes 3 scale items; (r) the MSFC includes 3 scale items; (s) the MSPT includes 12 scale items; (t) the NMSS includes 30 scale items; (u) the NPI includes 12 scale items; (v) the NPI-Q includes 12 scale items; (w) the PPBT includes 5 scale items; and (x) the TMT includes 12 scale items.

As a non-limiting example, one of the scale items in the UPDRS-III clinical scale is the retropulsion test. The retropulsion test examines the response to sudden body displacement produced by a quick, forceful pull on the shoulders while the patient is standing erect with eyes open and feet comfortably apart and parallel to each other. The user's score on the retropulsion test is an example of a scale item.

As another non-limiting example, the UPDRS-I clinical scale includes the following 13 scale items: (1) cognitive impairment; (2) hallucinations and psychosis; (3) depressed mood; (4) anxious mood; (5) apathy; (6) features of dopamine dysregulation syndrome; (7) sleep problems; (8) daytime sleepiness; (9) pain and other sensations; (10) urinary problems; (11) constipation problems; (12) light headedness on standing; and (13) fatigue.

As used herein, a "clinical scale item" means a scale item of a clinical scale.

In some implementations, values of functional states are calculated based on scores of one or more clinical scale items. As a non-limiting example, a user's score on the retropulsion test (which is a clinical scale item in the UPDRS-III clinical scale) sheds light on the user's functional states of balance, reaction time, physical strength and body awareness (which are each subfunctions or aspects of motor function).

A user's score on a clinical scale item may be used as an input when calculating values of one or more functional states of the user. As a non-limiting example: (a) a score on the retropulsion test (which is a scale item in the UPDRS-III clinical scale) may be used as input when calculating a value of the functional states of balance, reaction time, physical strength and body awareness, respectively; (b) a value of a user's functional state of balance may be computed based on the user's scores on multiple scale items, including the retropulsion test; (c) a value of a user's functional state of reaction time may be computed based on the user's scores on multiple scale items, including the retropulsion test; (d) a value of a user's functional state of physical strength may be computed based on the user's scores on multiple scale items, including the retropulsion test; and (e) a value of a user's functional state of body awareness may be computed based on the user's scores on multiple scale items, including the retropulsion test.

In order to calculate a training label that specifies a functional state of the user: (a) the user may be evaluated on one or more standard clinical scales; and (b) the user's scores on one or more scale items of the clinical scale(s) may be converted into a value of that functional state. A wide variety of conversion algorithms may be employed in order to convert scores on clinical scale items into values that specify functional states.

In some cases, the conversion (from clinical scale items to functional states) involves calculations that take into account what we call contributing scale items. As used herein, a "contributing scale item" means a clinical scale item for which the user's score on the item indicates impairment (i.e., impaired worse than normal) or less-than-normal performance. For instance, if, for a particular clinical scale item, scores greater than or equal to a threshold indicate impairment (i.e., impaired worse than normal), then that particular clinical scale item is a "contributing scale item" where the user's score for that item is greater than or equal to the threshold. Also, for instance, if, for a specific clinical scale item, scores less than or equal to a threshold indicate less-than-normal performance, then that specific clinical scale item is a "contributing scale item" where the user's score for that item is less than or equal to the threshold.

In the context of a conversion calculation (which converts from scores on clinical scale items to a value of a given functional state), to say that a clinical scale item is "connected" to the given functional state means that a score on the clinical scale item may be employed as an input to calculate a value of the given functional state, at least when the score on the clinical scale item indicates impairment or less-than-normal performance. A decision regarding which functional state(s) to associate with a given clinical scale item may be made in advance of the conversion calculation (e.g., based on prior research or heuristically). For instance, the user's score on a retropulsion test (which is a clinical scale item in the UPDRS-III clinical scale) may be associated with the functional states of balance, reaction time, physical strength and body awareness. Likewise, in the context of a conversion calculation (which converts from scores on clinical scale items to a value of a given functional state), to say that there is a "connection" between a scale item and a functional state means that the scale item and functional state are connected.

In some use scenarios: (a) each clinical scale item measures phenomena which influence (or are positively correlated with) one or more functional states; and (b) each functional state is influenced by (or is positively correlated with) phenomena measured by one or more clinical scale items. In some conversion calculations (which convert from scores on clinical scale items to a value of a given functional state): (a) each clinical scale item is connected with one or more functional states; and (b) each functional state is connected with one or more clinical scale items.

Different clinical scale items may have different answer formats, such as response scales, binary scores, ordinal scales and/or other metrics. When converting scores on different clinical scale items into a given functional state of a user, appropriate conversion formulas may be employed. Which conversion formula is employed may depend on the answer format of the clinical scale items that are employed.

Here are seven non-limiting examples of how a user's scores on clinical scale items may be converted into values of a functional state of the user. Example 1 (Binary): A functional state may take the value of the total number of contributing scale items connected to that functional state in the clinical scale(s) under analysis. Example 2 (Ordinal Absolute): A functional state may take the value of the total number of contributing scale items connected to that functional state, divided by the total number of connections between the scale items and the functional states for all of the clinical scale(s) under analysis. Example 3 (Ordinal Scaled): A functional state may takes the value of the total number of contributing scale items connected to that functional state, divided by the total number of connections between the scale items and the functional states for all of the clinical scale(s) under analysis, and scaled by the number of clinical items connected to that functional state. Example 4 (Interval Absolute): A functional state may take the value of the sum of the scores for all of the contributing scale items connected to that functional state in all of the clinical scale(s) under analysis. Example 5 (Interval Normalized): A functional state may take the value of the sum of the scores for all of the contributing scale items connected to that functional state in all of the clinical scale(s) under analysis, divided by the sum of the maximum possible scores for all of the clinical scale(s) under analysis. Example 6 (Interval Scaled) A functional state may take the value of the sum of the scores for the contributing scale items connected to that functional state, divided by the sum of the maximum possible scores for all of the clinical scale(s) under analysis, and scaled by the sum of the maximum possible scores for all of the scale items connected to that functional state. Example 7 (Scale-Tuned): A functional state may take a value that is computed using predefined conversion parameters (e.g., based on existing clinical scale data analysis). For instance, these conversion parameters may be defined based on: (a) intra-scale analysis; (b) inter-scale comparison for scale impairment range comparison; or (c) inter-scale item comparison for item impairment range comparison. In Example 7, absolute parameters may be normalized or scaled. In each of the seven examples in this paragraph, the functional state may be a state of a function (e.g., motor performance) or a state of a subfunction (e.g., balance).

In some cases: (a) a set of data regarding typing by a user is fed as input into one or more ML algorithms; (b) the inputted set of data includes augmented keystroke data, enriched keystroke data, augmented keystroke tensors, enriched keystroke data, and/or features (e.g., features described in the section above titled "Features"); and (c) the one or more ML algorithms output an assessment of one or more functional states of the user.

In some cases: (a) one or more ML algorithms are trained on a training dataset to assess one or more functional states; (b) the training dataset is labeled with labels that specify values of functional states, which values of functional states are derived from scores for clinical scale items; and (c) the training dataset (even before being labeled with values of functional states) comprises data which describes, or is derived from data which describes, typing by a user. For instance, the training dataset (even before being labeled with values of functional states) may comprise augmented keystroke data, enriched keystroke data, augmented keystroke tensors, enriched keystroke data, and/or features (e.g., features described in the section above titled "Features").

In some cases, it is advantageous to train the ML algorithms with data that is labeled with functional states of a user, rather than training with data that is labeled with clinical scores from standard clinical scales (such as the MoCA or MMSE). In some cases, this is because standard clinical scales for detecting an overall impaired domain (e.g. cognition), are too broad to detect specific subdomain impairment for certain conditions or too focused on disease specific aspects that simplify the true picture of functional impairment. Each clinical scale measures a number of different subdomains which consist of one or more scale items from the clinical scale.

To illustrate the problems that may arise from using scores on standard scales as training labels, consider the Montreal Cognitive Assessment (MoCA) and the Mini Mental Status Exam (MMSE), which are considered two of the industry's "gold standard" assessments for detecting impaired cognition. These two scales measure subfunctions such as visuospatial function, executive function, short-term memory, attention and concentration, language, temporal-spatial orientation. These two scales exhibit high sensitivity and specificity for detecting impaired cognition due to Alzheimer's disease, but not necessarily other diseases (e.g., patients with impaired cognition due to stroke). Previous work suggests that neither the MMSE nor the MoCA assess some common post-stroke impairments including aphasia, apraxia, and visual loss. Often, clinicians require patients to undergo a battery of neuropsychological examinations to detect cognitive impairment in different specific subfunctions (e.g., non-verbal memory and verbal memory). These two clinical scales are often not optimized to detect cognitive impairment in the context of other diseases, for example Multiple Sclerosis (MS) and Parkinson's disease. Clinical scales for specific diseases have been developed for this purpose, such as the Minimal Assessment of Cognitive Function in MS (MACFIMS) and the Parkinson's Disease Cognitive Functional Rating Scale (PD-CFRS). When patients take a battery of neuropsychological assessments, in some cases, different clinical scales can measure the same subfunction (e.g., nonverbal memory), and some clinical scales may be more robust than others. Understanding the specific subfunctions of impairment may be helpful for clinicians in order to assess a patient's overall health. If an overall score on a clinical scale is used as a training label, the training label may omit information about which specific subfunction (e.g., nonverbal memory or verbal memory) the user has impairments in, which may very likely affect the user's typing style.

As another example of problems that may arise from training with labels that are scores on standard clinical scales, consider the UPDRS-III. The overall score on the UPDRS-III does not give visibility into which specific subfunctions participants are impaired in. For example, person A and person B could have the same UPDRS-III score of 20, but person A could be impaired in the subfunctions of gait and bradykinesia, while person B could be impaired in the subfunctions of rigidity and postural instability. Training an ML model against the overall standardized score of 20 may force the model to learn that these two significantly different patterns of impairment should output the same biomarker.

In contrast, training the ML algorithm(s) with labels that are values of functional states may be helpful because these functional states may indicate precisely which functions (e.g., motor) or subfunctions (e.g., balance, reaction time) the user is impaired in. Furthermore, the values of functional states may comprise a standardized representation of the user's status. This standardized representation may be employed for assessing a wide range of health conditions, rather than being limited to a particular disease or symptom.

As noted above, in some cases, scores on standard clinical scales (which are conventionally used to assess neurological or neurodegenerative diseases) are translated into values of a standardized set of states that describe specific aspects of motor, cognitive and behavioral functions. The values of the states may provide a standardized representation of clinical status. This standardized representation may facilitate: (a) biomarker development (e.g., by training machine learning models directly against the subfunctions of interest); (b) biomarker validation (e.g., by validating newly developed algorithms against a variety of dimensions of impairment); (c) biomarker interpretation (e.g., by providing a quantitative representation of the weight of different functional dimensions in an outcome score); and (d) study design (e.g., by providing a tool to assist in the clinical design of studies regarding using typing data to assess health conditions).

In some cases, a functional state is binary (e.g., impaired or normal). In some cases, a functional state has more than two possible values, in such a way that the value of the state is indicative of degree or severity of impairment (including normal or no impairment).

In some cases, functional states are used as training labels in a multitask learning approach. For instance, eight regressors may be simultaneously trained to assess impairment in eight subfunctions, namely perception, attention, executive function, visual motor ability, language/verbal skills, non-verbal memory, verbal memory, and sensation. This eight-regressor subfunction learning approach is a variation of the $nQi_{COG}$ algorithm described in what we call Example B (see below). Rather than generate a single score based on a binary label (cognitively normal vs cognitively impaired), the eight-regressor subfunction learning approach simultaneously trains eight different regression models to learn the level of severity measured on each of the subfunctions of interest.

In some cases, functions are employed to validate and enhance clinical interpretability of the typing-based biomarkers. For instance, suppose one wants to better understand the $nQi_{COG}$ algorithm described in what we call Example B (see below). By correlating individuals' $nQi_{COG}$ scores to their functional states, one may gain get a better understanding on the aspects of the function that are more directly connected to the $nQi_{COG}$ scores. This process can be applied at any level of the model pipeline, final biomarker, sub-scores and/or feature level.

Unless the context clearly indicates otherwise, each functional state mentioned herein may be, but is not necessarily, either: (a) a state of a function mentioned in the first paragraph of this "Functional States" section; or (b) a state of an aspect of a function, which aspect is mentioned above in the first paragraph of this "Functional States" section.

Hardware

Figure 10:
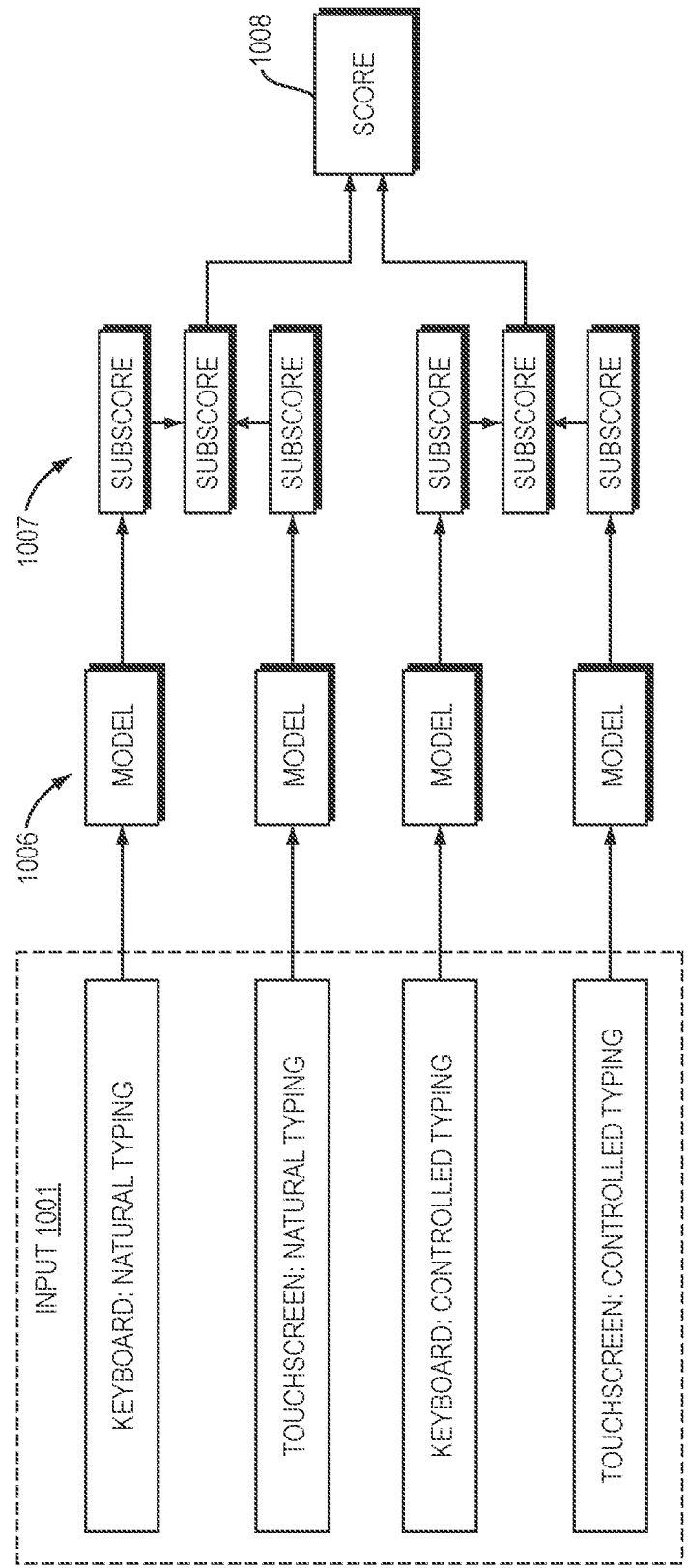
FIG. 10 is a flowchart of a method in which multiple machine learning models contribute to an assessment of a health condition.

FIG. 10 is a flowchart of a method in which multiple machine learning models contribute to an assessment of a health condition, in an illustrative implementation of this invention. In FIG. 10, four machine learning (ML) models 1006 are employed. Each ML model receives a different type of input 1001. In FIG. 10: (a) a first ML model receives, as input, data that represents or is derived from measurements of keystrokes typed on a keyboard by a user during a natural typing session; (b) a second ML model receives, as input, data that represents or is derived from measurements of keystrokes typed on a touchscreen by a user during a natural typing session; (c) a third ML model receives, as input, data that represents or is derived from measurements of keystrokes typed on a keyboard by a user during a controlled typing session; and (d) a fourth ML model receives, as input, data that represents or is derived from measurements of keystrokes typed on a touchscreen by a user during a controlled typing session. In some cases, the assessment that is outputted by the method is a combined score 1008 which is calculated based on the individual outputs of all four ML models. Alternatively, the assessment that is outputted by the method may be one of the subscores 1007. For instance, the assessment may either be: (a) a subscore that is a separate output of one the ML models; or (b) a combined subscore that is calculated based on two separate sub scores that are each a separate output of a different ML model.

Figure 11:
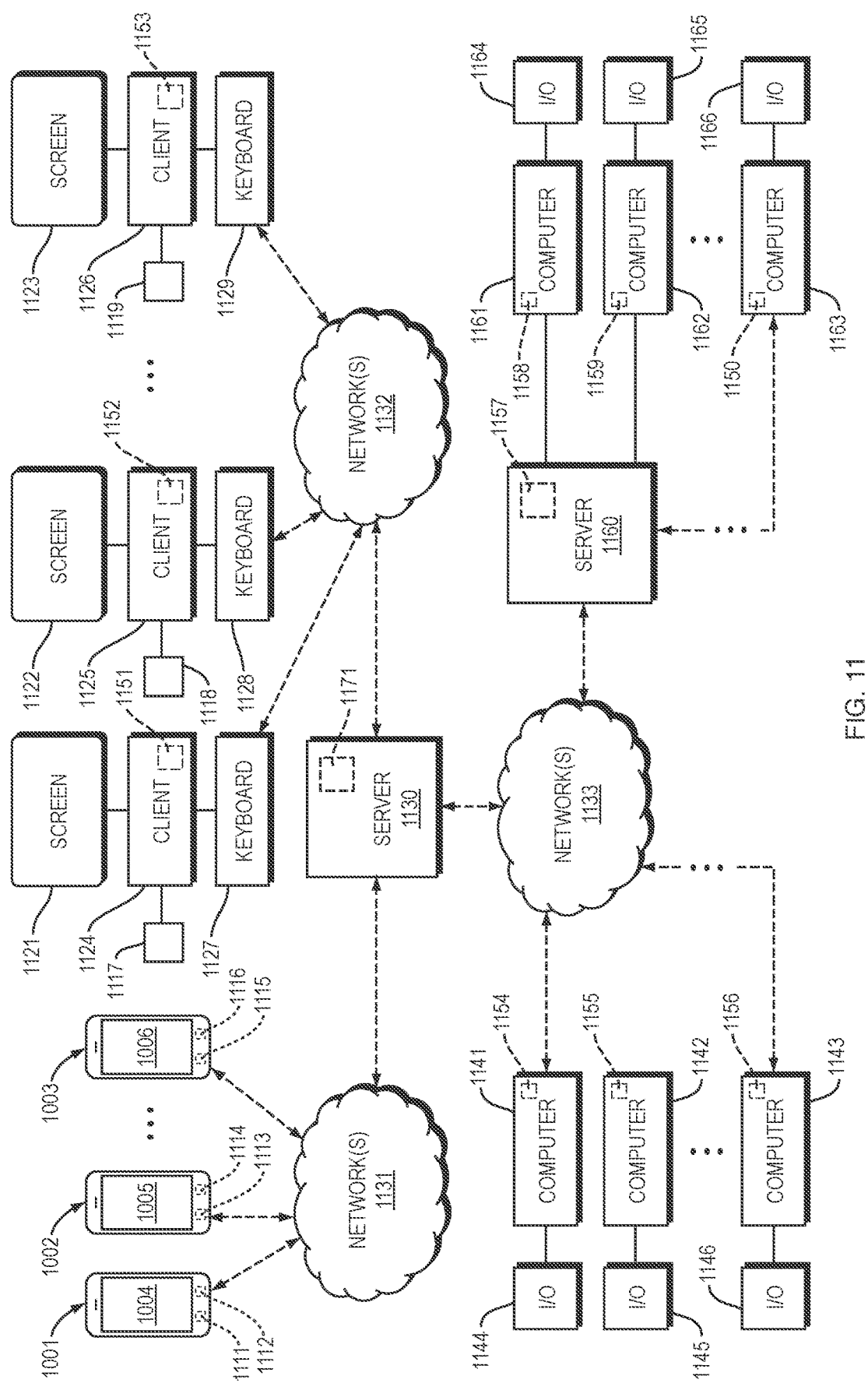
FIG. 11 is a block diagram of hardware for a system that assesses a health condition based on keystroke data.

FIG. 11 is a block diagram of hardware for a system that assesses a health condition based on keystroke data, in an illustrative implementation of this invention.

In FIG. 11, multiple users may type on touchscreens (e.g., 1004, 1005, 1006) of mobile computing devices (MCDs) (e.g., 1001, 1002, 1003). Data representing measurements of keystrokes that occur during this typing may be processed by computers (e.g., 1111, 1113, 1115) onboard the respective MCDs. For instance, these onboard computers may comprise microprocessors or microcontrollers. These onboard computers (e.g., 1111, 1113, 1115) may output data that is derived from (and/or represents) the measurements of keystrokes. This data (which is outputted by computers onboard the MCDs) may comprise: (a) enriched keystroke data; (b) augmented keystroke data; (c) data that encodes one or more enriched keystroke tensors; and/or (d) data that encodes one or more augmented keystroke tensors. This data (which is outputted by computers onboard the MCDs) may be sent, via one or more communication networks 1131, to a server 1130. In some cases, this data (which is outputted by computers onboard the MCDs) is wirelessly transmitted by wireless modules (e.g., 1112, 1114, 1116) that are onboard the respective MCDs.

Also, in FIG. 11, the multiple users may type on keyboards (e.g., 1127, 1128, 1129). Data representing measurements of keystrokes that occur during this typing may be processed by client computers (e.g., 1124, 1125, 1126) that are connected to the respective keyboards. For instance, these client computers may comprise microprocessors, microcontrollers, personal computers, or laptop computers. These client computers (e.g., 1124, 1125, 1126) may output data that is derived from (and/or represents) the measurements of keystrokes. This data (which is outputted by client computers) may comprise: (a) enriched keystroke data; (b) augmented keystroke data; (c) data that encodes one or more enriched keystroke tensors; and/or (d) data that encodes one or more augmented keystroke tensors. This data (which is outputted by client computers) may be sent, via one or more communication networks 1132, to server 1130. In some cases, this data (which is outputted by the client computers) is wirelessly transmitted by wireless modules (e.g., 1151, 1152, 1153) that are housed in or connected to the respective client computers. Screens (e.g., 1121, 1122, 1123) and other I/O devices (e.g., 1117, 1118, 1119) may be connected to the client computers. In FIG. 11, these screens and other I/O devices may enable a user to interact with a graphical user interface (GUI) that, among other things: (a) displays a suggested word or phrase which has been predicted by a computer; and (b) enables a user to select the suggested word or phrase. Likewise, in FIG. 11, touchscreens (e.g., 1004, 1005, 1006) may each present a GUI with that functionality.

In FIG. 11, server 1130 may output an assessment of one or more health conditions. This assessment may be communicated, via one or more communication networks 1133, to a first set of additional computers (e.g. 1141, 1142, 1143). This first set of additional computers may, in turn, be programmed to cause one or more I/O devices (e.g., 1144, 1145, 1146) to display or otherwise present the assessment. In some cases, the assessment may be sent to another server computer (e.g., 1160), which in turn sends the assessment to a second set of additional computers (e.g., 1161, 1162, 1163). This second set of additional computers may, in turn, be programmed to cause one or more I/O devices (e.g., 1164, 1165, 1166) to display or otherwise present the assessment. Persons such as medical professionals, hospital or medical workers, or employees of insurance companies may view the assessment via these I/O devices (e.g., 1144, 1145, 1146, 1164, 1165, 1166).

In FIG. 11, the assessment of a patient's health condition may also be sent, via communication networks (e.g., 1131, 1132) to MCDs or computers of the patient or of the patient's family, friend or caregiver. For instance, the assessment may be sent to: (a) an MCD on which the patient's typing was measured; or (b) a client computer connected to a keyboard on which the patient's typing was measured.

Example A

In this section, we provide a non-limiting example of using keystroke data to assess cognitive function (e.g., to detect a decline in cognitive function). We sometimes call this example "Example A".

In Example A, cognitive function is assessed by measuring its effect on a complex bimanual act of typing. One reason that this approach works may be that typing is a complex task that requires not only fine motor performance but also fine motor feedback and cognitive control. Analysis of keystroke dynamics of single keystrokes in individual zones, in combination with analysis of keystroke dynamics of bigrams, may detect differences between control subjects and cognitively impaired subjects.

In Example A, one or more location-based features are computed based on keystroke data (such as press time and release time) and/or key location data (such as keyboard zone).

In Example A, a computer calculates a first set of features that describe timing of events related to a keystroke, regardless of where (on the keyboard) the keystroke occurred. For instance, hold time may be calculated based on the press time and release time of a keystroke. For example, hold time may be calculated as $HT_n = R_{k_n} - P_{k_n}$, where $HT_n$ is hold time of the $n^{th}$ keystroke, $P_{k_n}$ is press time of the $n^{th}$ keystroke, and $R_{k_n}$ is release time of the $n^{th}$ keystroke In Example A, a threshold is applied to the hold times, discarding any hold times above or below a certain value.

IF (Hold Time)>(Upper Threshold), THEN Discard (Hold Time).

IF (Hold Time)<(Lower Threshold), THEN Discard (Hold Time).

In this Example A, for a typing stream by a user, the m-bin distribution may be calculated for each of the n keyboard zones, as well as for the entire keyboard regardless of zone, using a relative frequency histogram.

In Example A, this data may be represented with a table, where each row represents a single user, and each column represents that user's m-bin relative frequency histogram for the overall keyboard and for keyboard zones 1 through n.

In Example A, a computer calculates a second set of features that each relate to a bigram, where the bigram consists of a pair of two consecutive keystrokes. As a non-limiting example, two consecutive bigrams $B_{k1,k2}$ and $B_{k2,k3}$ by a single user (User 1) may be represented by Table 1.

TABLE 1

| | User 1 | | | | | | |
|---|---|---|---|---|---|---|---|
| | $B_{k_1,k_2}$ | $P_{k_1}$ | $P_{k_2}$ | $R_{k_1}$ | $R_{k_2}$ | $Z_{k_1}$ | $Z_{k_2}$ |
| User 1 | $B_{k_1,k_3}$ | $P_{k_2}$ | $P_{k_3}$ | $R_{k_2}$ | $R_{k_3}$ | $Z_{k_2}$ | $Z_{k_3}$ |

In Table 1: (a) $B_{k1,k2}$ is a first bigram consisting of a first keystroke $k_1$ and a second keystroke $k_2$; (b) $B_{k2,k3}$ is a second bigram consisting of the second keystroke $k_2$ and a third keystroke $k_3$; (c) $P_{k_1}$, $P_{k_2}$, and $P_{k_3}$ are the press times of the first, second and third keystrokes, respectively; (d) $R_{k_1}$, $R_{k_2}$, and $R_{k_3}$ are the release times of the first, second and third keystrokes, respectively; and (e) $Z_{k_1}$, $Z_{k_2}$, and $Z_{k_3}$ are the keyboard zones for the first, second and third keystrokes, respectively.

In Example A, a computer may also employ a bigram data structure to calculate metrics based on a bigram as a unit rather than the individual keystroke as a unit. For instance, a computer may employ a bigram structure to calculate flight time and delay time. For example, a computer may calculate $FT_n = P_{k_{n+1}} - P_{k_n}$ and may calculate $DL_n = P_{k_{n+1}} - R_{k_n}$, where $FT_n$ is flight time for the pair of keystrokes that starts with the $n^{th}$ keystroke, $DL_n$ is delay for the pair of keystrokes that starts with the $n^{th}$ keystroke, $P_{k_n}$ is press time of the $n^{th}$ keystroke, $P_{k_{n+1}}$ is press time of the $(n+1)^{th}$ keystroke, and $R_{k_n}$ is release time of the $n^{th}$ keystroke.

In Example A, both the flight time and the delay time may be standardized for each user. This may be desirable because: (a) these two metrics may be affected by typing speed; and (b) different users may have different typing speeds. This standardization (of flight time and delay time) may be performed by subtracting the mean value from each sample, thus centering the distribution at 0. This may facilitate comparisons of flight time and delay time of different users.

In Example A, a standardized flight time (SFT) and a standardized delay time (SDL) may be calculated for the overall keyboard, regardless of zones. These two metrics (SFT and SDL) may be calculated in different ways, such as by keyzone combination, by keyzone distance, or by hand dynamic.

A "keyzone combination" may describe the permutation of zones in a bigram. Each bigram zone distance may be represented as $[Z_{k_1}, Z_{k_2}]$, where $Z_{k_1}$ is the keyboard zone of the first keystroke in the bigram and $Z_{k_2}$ is the keyboard zone of the second keystroke in the bigram. As a non-limiting example, assume that n=6 (i.e., the alphanumeric keyboard is divided into 6 zones, left to right). In this example, the keyzone combination of the bigram "al" (i.e., the letter "a" followed by the letter "l") is [1,6] while the keyzone combination of its reverse "la" is [6,1]. For any given number n of keyboard zones, there are $n^2$ possible keyzone combinations. (For instance, if there are n=6 keyboard zones, then there are 36 possible keyzone combinations). For each keyzone combination, the flight time and delay time m-bin distributions may be calculated, using a relative frequency histogram.

In Example A, after these distributions are calculated, they may then be added on as additional columns to the data structure where each row is a user and each column is a feature.

The "keyzone distance" of a bigram may be computed by subtracting the second keystroke's key zone from the first keystroke's key zone: $Z_{k_1} - Z_{k_2}$. For instance, in a keyboard with 6 alphanumeric keyboard zones: (a) the "a" key may be in zone 1 and the "l" key may be in zone 6; and (b) thus, the bigram "al" may have a keyzone distance of 5. Keyzone distances may be signed, meaning they may be positive or negative. For instance, the bigram "al" may have a keyzone distance of 5, and the opposite bigram "la" may have a keyzone distance of −5. In some cases, there are 2n−1 possible keyzone distances, where n is the number of alphanumeric keyboard zones. For instance, if n=6, then we have the following possible keyzone distances: −5, −4, −3, −2, −1, 0, 1, 2, 3, 4, and 5. For each keyzone distance, the standardized flight time and delay time m-bin distributions may be calculated, using a relative frequency histogram.

Table 2 shows an example of keyzone distances and keyzone combinations for a keyboard that has six keyboard zones. In each keyzone combination in Table 2, the first number indicates the keyboard zone of the first keystroke in a bigram and the second number indicates the keyboard zone of the second keystroke in the bigram. For instance, [5,1] represents a keyzone combination in which the first keystroke of a bigram occurs in keyboard zone 5 and the second keystroke of the bigram occurs in keyboard zone 1.

TABLE 2

| Keyzone Distance | Keyzone Combinations Included |
|---|---|
| −5 | [6, 1] |
| −4 | [6, 2], [5, 1] |
| −3 | [6, 3], [5, 2], [4, 1] |
| −2 | [6, 4], [5, 3], [4, 2], [3, 1] |
| −1 | [6, 5], [5, 4], [4, 3], [3, 2], [2,1] |
| 0 | [1, 1], [2, 2], [3, 3], [4, 4], [5, 5], [6, 6] |
| 1 | [1, 2], [2, 3], [3, 4], [4, 5], [5, 6] |
| 2 | [1, 3], [2, 4], [3, 5], [4, 6] |
| 3 | [1, 4], [2, 5], [3, 6] |

TABLE 2-continued

| Keyzone Distance | Keyzone Combinations Included |
|---|---|
| 4 | [1, 5], [2, 6] |
| 5 | [1, 6] |

In Example A, after these distributions are calculated, they may be added as additional columns to a data structure where each row is a user and each column is a feature.

The "hand dynamic" of a bigram may be computed by categorizing each of the n keyboard zones as either on the left side of the keyboard or the right side. This leads to four possible hand dynamics: left-left, right-right, left-right, and right-left. Using the bigram from our previous example, "al" would be included in the left-right dynamic, while "la" would be included in the "right-left" dynamic. In some cases, in a keyboard with six alphanumeric keyboard zones, zones 1, 2, and 3 are "left" and zones 4, 5, and 6 are "right". Alternatively, keyboard zones in the middle of the keyboard are disregarded for the hand dynamics analysis, leaving only the zones on the extreme right or left sides of the keyboard for the hand dynamics analysis. For instance, if a keyboard has six alphanumeric keyboard zones, then zones 3 and 4 may be disregarded in the hand dynamics analysis, since they are in the middle of the keyboard. For each hand dynamic, the standardized flight time and delay time m-bin distributions may be calculated, using a relative frequency histogram.

In Example A, after these distributions are calculated, they may then be added on as additional columns to the data structure where each row is a user and each column is a feature.

In Example A, after all of these features are calculated, there are $2n^2+5n+9$ number of SFT and SDL features per user. For instance, if n=6 (i.e., the keyboard is treated as having six alphanumeric keyboard zones), there may be a total of 111 SFT and SDL features per user:

SFT feature count=$(n^2)+(2n-1)+(4)+(1)=n^2+2n+4$

SDL feature count=$(n^2)+(2n-1)+(4)+(1)=n^2+2n+4$

Number of features=$2(n^2+2n+4))+(n+1)=2n^2+5n+9$

In Example A, a convolutional neural network (CNN) may be employed to analyze these calculated features. Each distribution may have x bins. For each user, the data may be arranged in a matrix with $2n^2+5n+9$ rows and m columns, in such a way that each row represents one of the previously defined features and each column i represents the $i^{th}$ bin in that distribution.

In Example A, the CNN may be trained in multiple ways. One such way is binary classification, where all subjects that have been identified with any kind of cognitive impairment (ranging from mild cognitive impairment all the way through severe dementia) in one group, regardless of severity, with the other group being healthy, age-and-gender matched control subjects. Another way to train the CNN is with each level of severity being its own group (in addition to controls), therefore allowing the model to predict not just any cognitive impairment but actually a specific severity level of cognitive impairment.

Because of the CNN's architecture, the order in which variables are fed into the model may influence the kernels that the model learns and thus its ability to distinguish between different groups.

In Example A, variables may be fed into the CNN in different orders and the results may be compared. For instance, the results—for each particular order in which the variables are fed into the CNN—may comprise an AUC (area under the curve) of an ROC (receiver operating characteristic) curve.

In Example A, the order in which variables are fed into the CNN (or other machine learning algorithm) may be selected by employing a seeded random number generator and shuffle the variables randomly.

Alternatively, in Example A, the order in which variables are fed into the CNN (or other machine learning algorithm) is selected based on (a) the keyboard section the variable relates to and/or (b) the type of variable (e.g. hold time variables, flight time variables, delay variables). As a non-limiting example, any variables that describe key presses in zones 1, 2, or 3 may be treated as relating to the left section of the keyboard. Likewise, any variables that describe bigrams where both keys are in zones 1, 2, and 3 may be treated as relating to the left side of the keyboard.

As non-limiting examples, the order in which variables are fed as input into the CNN (or other machine learning algorithm) may be selected in any of the following ways:
  Order 1: variables arranged by keyboard section (left, right, etc.) alternating by variable type (hold time, flight time, delay time, then repeat).
  Order 2: variables arranged by keyboard section (left, right, etc.) and grouped variable type (all hold times, all flight times, all delay times).
  Order 3: combination of order 1 and order 2.
  Order 4. Variables arranged solely by variable type, ignoring keyboard section.

Example B

In this section, we provide another non-limiting example of using keystroke data to assess cognitive function (e.g., to detect a decline in cognitive function). We sometimes call this example "Example B".

In Example B, a computer calculates what we sometimes call a "$nQi_{COG}$" score, which is indicative of cognitive function.

In Example B, a computer may calculate a $nQi_{COG}$ score based on features that are calculated directly or indirectly from typing data. In Example B, the features were all heuristically selected by a human. Loosely speaking, one might say that the features in Example B were "manually engineered".

In Example B, augmented typing data is transformed into enriched keystroke tensors that include signals from the following feature families: keystroke, pauses, backspace and precision. In Example B, these enriched keystroke tensors may be reduced to a predefined size feature vector, by selecting only some of the features described by the enriched keystroke tensors.

In Example B, the following features are employed to calculate a $nQi_{COG}$ score: (a) median hold time, first quartile (Q1) hold time, third quartile (Q3) hold time, outlier rate of hold time, interquartile range (IQR) of hold time, outlier spread of hold time, and position of Q2 of hold time; (b) median normalized flight time, Q1 normalized flight time, Q3 normalized flight time, outlier rate of normalized flight time, IQR of normalized flight time, outlier spread of normalized flight time, and position of Q2 of normalized flight time; (c) count, mean, standard deviation, median and IQR of pauses in words; (d) count, mean, standard deviation, median and IQR of pauses between words in a sentence; (e) count, mean, standard deviation, median and IQR of pauses in sentences; (f) count, mean, standard deviation, median and IQR of pauses between sentences; (g) count, mean, standard deviation, median and IQR of special pauses; (h) count, mean, standard deviation, median and IQR of error pauses; (i) count, mean, standard deviation and median of number of letters in a word; (j) count, mean, standard deviation and median of number of words in a sentence; (k) complexity of a sentence; (l) rate, count, mean, standard deviation, median and IQR of single backspaces; and (m) rate, count, mean, standard deviation, median and IQR of multiple backspaces. For purposes of this paragraph: (a) an "outlier" means a value that exceeds the third quartile by more than 1.5 times IQR or that is less than the first quartile by more than 1.5 times IQR; (b) "outlier spread" means the standard deviation of the values that exceed the third quartile by more than 1.5 times IQR (i.e. standard deviation of the upper outliers); (c) "error pause" means a pause preceding an "unknown" key (e.g., a key that is not alphanumeric for which data regarding its identity or type is not available); (d) "special pause" means a pause preceding a key that is not alphanumeric (e) "single backspace" means a backspace that is not part of a pair of consecutive backspaces; (f) "multiple backspaces" means a sequence of two or more consecutive backspaces; (g) "position of Q2 of hold time" means (Q2−Q1)/(Q3−Q1) of hold time, where Q1, Q2, Q3 and Q4 are the first, second, third and fourth quartiles, respectively; and (h) "position of Q2 of normalized flight time" means (Q2−Q1)/(Q3−Q1) of normalized flight time, where Q1, Q2, Q3 and Q4 are the first, second, third and fourth quartiles, respectively. Note that "pauses in a sentence" includes: (a) pauses in words; and (b) pauses between words in a sentence.

In Example B, the tensor encoding phase also includes a feature selection filter based on session parameters. Depending on the source (touchscreen or mechanical) and context of typing (controlled or free), data is encoded into different feature vectors and directed to a specific model trained for that specific session type.

In Example B, four different types of input are employed and are fed into four different support vector machines (SVMs), respectively. Specifically, in Example B: (a) a first SVM receives, as input, data that represents or is derived from measurements of keystrokes typed on a keyboard by a user during a natural typing session; (b) a second SVM receives, as input, data that represents or is derived from measurements of keystrokes typed on a touchscreen by a user during a natural typing session; (c) a third SVM receives, as input, data that represents or is derived from measurements of keystrokes typed on a keyboard by a user during a controlled typing session; and (d) a fourth SVM receives, as input, data that represents or is derived from measurements of keystrokes typed on a touchscreen by a user during a controlled typing session.

In Example B, a sub-score is generated by each SVM. In Example B, these sub-scores are numbers between 0 and 1 that represent the probability of the input sample being classified as belonging to a cognitively impaired individual. Sub-scores may be taken as final outputs. Alternatively, the sub-scores may be aggregated into a single score that is based on all four of these types of inputs (e.g., in the manner shown in FIG. 10).

In a test of a prototype of this invention, typing data was analyzed in the manner described in Example B. In this test, the $nQi_{COG}$ algorithm correctly distinguished between patients diagnosed as cognitively normal and patients diagnosed as cognitively impaired, with an AUC of 0.77 ($p<0.001$). For performance comparison, the AUC of the $nQi_{COG}$ algorithm (0.77) is comparable to the AUC of conventional cognitive assessment scales such as the Mini Mental State Exam (0.72) and Montreal Cognitive Assessment (0.82). In this test, the $nQi_{COG}$ algorithm correctly distinguished between participants with positive amyloid PET scans and those with negative PET scans with an AUC of 0.79. Additional preliminary analysis comparing the $nQi_{COG}$ to other well-known functional and cognitive staging scales (Activities of Daily Living Questionnaire, Functional Activities Questionnaire, Clinical Dementia Rating scale) revealed significant correlations that did not appear to be influenced by demographic confounders (including age or level of education).

Normalization, Scaling, Shifting, Standardization, Clipping

In illustrative implementations of this invention, any value that measures or is derived from keystrokes may be normalized, rescaled, scaled, shifted, standardized, or clipped. For instance, in illustrative implementations of this invention, any one or more of the following may be normalized, rescaled, scaled, shifted, standardized, or clipped: augmented keystroke data, enriched keystroke data, elements of keystroke tensors, elements of an interim dataset, features, and biomarkers. Any method of normalization, rescaling, scaling, shifting, standardization or clipping may be employed. The remainder of this paragraph lists non-limiting examples: For instance, normalization or standardization may be performed as described in the section above titled "Functional States". Or, for instance, the normalization may comprise (a) Z-score normalization; (b) adjusting values measured on different scales to a notionally common scale; (c) normalizing a vector by dividing each element of a vector by a norm of a vector, in order to make all of the normalized elements of a vector have a value between 0 and 1; or (d) bringing probability distributions into alignment (e.g., into a normal distribution). In some use scenarios, normalization may result in normalized values that each comprise a standard score, student's t-statistic, studentized residual, standardized moment, or coefficient of variation. In some use scenarios, scaling may be employed and may comprise adding or subtracting a constant to each element of a vector, and then multiplying or dividing each element of the vector by a constant. In some use scenarios, scaling is employed and comprises logarithmic scaling, linear scaling or a combination of both logarithmic and linear scaling. In some use scenarios, shifting or rescaling is employed and facilitates comparing shifted or rescaled values from different datasets in a way that eliminates the effects of one or more variables. In some use scenarios, standardization is employed and comprises subtracting, from each element of a vector, a measure of location and dividing each element of a vector by a measure of scale (e.g., by subtracting the mean of a vector of random numbers from each element of the vector and then dividing each element of the vector by the standard deviation of the vector).

Location-based nQi Scores

In some implementations of this invention, nQi scores are calculated from keystrokes. As used herein, an "nQi score" means a metric that quantifies fine motor impairment manifested in keystrokes. In some cases, the higher an nQi score is, the greater the motor impairment. The manner in which nQi scores are calculated is described below in this document.

In some cases, location-based nQi scores are calculated separately for different regions of a keyboard. As used herein, a "location-based nQi score" means an nQi score that is calculated from keystrokes that occur in a particular region of a keyboard, which particular region includes some, but not all, of the keys of the keyboard (e.g., some but not all of the alphanumeric keys of the keyboard). Thus, a location-based nQi score may quantify fine motor impairment manifested in keystrokes that occur in a particular region of a keyboard.

For instance, in some cases, a keyboard is divided into two regions: a right-hand region and a left-hand region. For example, in some cases, for a QWERTY keyboard: (a) the right-hand region consists of the keys 6, Y, H and N and all alphanumeric keys to the right of them; and (b) the left-hand region consists of the keys 5, T, G, B and all alphanumeric keys to the left of them.

Alternatively, the keyboard may be divided into more than two regions (e.g., three, four, five, six or more regions). For instance, the keyboard may be divided into six regions.

Differences between the nQi scores for different regions of a keyboard may be calculated as of a single date, to generate what we sometimes call a "static" measure of differences among the nQi scores for the various regions of the keyboard.

Alternatively, in what we sometimes call a "longitudinal method", nQi scores for different regions of a keyboard are calculated for each of multiple dates, and changes in these nQi scores are analyzed.

For instance, in some cases: (a) an asymmetry metric quantifies a difference between nQi scores for the left-hand region of the keyboard and nQi scores for the right-hand region of a keyboard; (b) this asymmetry metric is calculated for each of multiple dates; and (c) changes in this asymmetry metric over time are analyzed.

Now we describe a prototype of this invention. In this prototype, changes over time in asymmetry between nQi scores for right-hand and left-hand regions over time are analyzed.

In this prototype, the keyboard is divided into two regions: a dominant side and a non-dominant side. For a right-handed person, the dominant side is the right side of the keyboard and the non-dominant side is the left side of the keyboard. For a left-handed person, the dominant side is the left side of the keyboard and the non-dominant side is the right side of the keyboard. Likewise, for a right-handed person, the dominant hand is the right hand and the non-dominant hand is the left hand. For a left-handed person, the dominant hand is the left hand and the non-dominant hand is the right hand. In this prototype, nQi scores may be separately calculated for these two regions. Alternatively, in this prototype, three different categories of nQi scores may be computed: (1) nQi scores derived solely from keystrokes in the dominant side of the keyboard; (2) nQi scores derived solely from keystrokes in the non-dominant side of the keyboard; and (3) nQi scores derived from keystrokes on the entire keyboard.

In this prototype, whether a patient is right-handed or left-handed may be determined either: (a) based on input from the patient or a health care worker (e.g., by the patient or a doctor inputting an answer to a question); or (b) by analyzing keystroke patterns of the patient in the right-hand region and left-hand region of the keyboard. For instance, users tend to present slightly slower hold times in their non-dominant hand. By comparing the main peak of the hold time distributions for right-left side keystrokes, hand dominance may be inferred.

As is well known, many patients with Parkinson's disease (PD) have either dominant-side-onset (DSO) of PD or non-dominant-side-onset (NDSO) of PD.

In this prototype, whether a PD patient is DSO or NDSO may be determined either: (a) based on input from the patient or from a health care worker (e.g., by the patient or a doctor inputting an answer to a question); or (b) by analyzing keystroke patterns of the patient in the right-hand region and left-hand region of the keyboard.

In this prototype, a method comprising six steps may be employed, to calculate asymmetry in nQi scores between the right hand and left hand of a PD patient. We sometimes call this method the "PD asymmetry method".

In this prototype, the first four steps the PD asymmetry method are:

For patient i in {Patient 1, Patient 2, . . . , Patient N−1, Patient N}, perform steps 1-4 below.

1. Compute the median left hand $L_{i,b}$ and median right hand $R_{i,b}$ scores at baseline assessment

| Baseline assessment data | | |
|---|---|---|
| Patient | Left hand median | Right hand median |
| Patient 1 | $L_{1,b}$ | $R_{1,b}$ |
| Patient 2 | $L_{2,b}$ | $R_{2,b}$ |
| ... | ... | ... |
| Patient N − 1 | $L_{N-1,b}$ | $R_{N-1,b}$ |
| Patient N | $L_{N,b}$ | $R_{N,b}$ |

2. Compute the median left hand $L_{i,f}$ and median right hand $R_{i,f}$ scores at final assessment

| Final assessment data | | |
|---|---|---|
| Patient | Left hand median | Right hand median |
| Patient 1 | $L_{1,f}$ | $R_{1,f}$ |
| Patient 2 | $L_{2,f}$ | $R_{2,f}$ |
| ... | ... | ... |
| Patient N − 1 | $L_{N-1,f}$ | $R_{N-1,f}$ |
| Patient N | $L_{N,f}$ | $R_{N,f}$ |

3. Compute difference in right and left for baseline and final visit

| Difference in Left and Right Medians | | |
|---|---|---|
| Patient | Baseline assessment | Final assessment |
| Patient 1 | $L_{1,b} - R_{1,b}$ | $L_{1,f} - R_{1,f}$ |
| Patient 2 | $L_{2,b} - R_{2,b}$ | $L_{2,f} - R_{2,f}$ |
| ... | ... | ... |
| Patient N − 1 | $L_{N-1,b} - R_{N-1,b}$ | $L_{N-1,f} - R_{N-1,f}$ |
| Patient N | $L_{N,b} - R_{N,b}$ | $L_{N,f} - R_{N,f}$ |

4. Compute final assessment difference minus baseline difference

| Patient | Final difference minus baseline difference |
|---|---|
| Patient 1 | $(L_{1,f} - R_{1,f}) - (L_{1,b} - R_{1,b})$ |
| Patient 2 | $(L_{2,f} - R_{2,f}) - (L_{2,b} - R_{2,b})$ |
| ... | ... |
| Patient N − 1 | $(L_{N-1,f} - R_{N-1,f}) - (L_{N-1,b} - R_{N-1,b})$ |
| Patient N | $(L_{N,f} - R_{N,f}) - (L_{N,b} - R_{N,b})$ |

In this prototype, the fifth step of the PD asymmetry method is to group patients by side onset, and to calculate a change in asymmetry over time, which may be quantified for patient i as $(L_{i,f} - R_{i,f}) - (L_{i,b} - R_{i,b})$:

| Sideness | Patient | Final difference minus baseline difference |
|---|---|---|
| Dominant | Patient 1 | $(L_{1,f} - R_{1,f}) - (L_{1,b} - R_{1,b})$ |
| Dominant | Patient 2 | $(L_{2,f} - R_{2,f}) - (L_{2,b} - R_{2,b})$ |
| ... | ... | ... |
| Dominant | Patient M | $(L_{M,f} - R_{M,f}) - (L_{M,b} - R_{M,b})$ |
| Non-Dominant | Patient M + 1 | $(L_{M+1,f} - R_{M+1,f}) - (L_{M+1,b} - R_{M+1,b})$ |
| Non-Dominant | Patient M + 2 | $(L_{M+2,f} - R_{M+2,f}) - (L_{M+2,b} - R_{M+2,b})$ |
| ... | ... | ... |
| Control | Patient N − 1 | $(L_{N-1,f} - R_{N-1,f}) - (L_{N-1,b} - R_{N-1,b})$ |
| Control | Patient N | $(L_{N,f} - R_{N,f}) - (L_{N,b} - R_{N,b})$ |

In this prototype, for purposes of the PD asymmetry method, "control" users are age-matched, healthy persons who do not have Parkinson's disease.

In this prototype, the sixth step of the PD asymmetry method is to compare the distributions of asymmetry (e.g., distributions of $(L_{i,f} - R_{i,f}) - (L_{i,b} - R_{i,b})$) for DSO PD patients, NDSO PD patients and healthy control patients.

In this prototype, one or more thresholds may be calculated for distributions of asymmetry between nQi scores for the right-hand and left-hand sides of a keyboard. These thresholds may indicate when asymmetry in nQi scores (or changes in asymmetry in nQi scores) are clinically significant factors for assessing impairment due to Parkinson's disease in DSO patients, NDSO patients or both.

In this prototype, these thresholds may be calculated in various ways. For instance: (a) a multiclass ROC (receiver operating characteristic) curve may be computed, and a one-versus-all optimization may be performed to calculate a region of the ROC curve that maximizes sensitivity to (and specificity for) impairment of fine motor control due to Parkinson's disease for DSO or NDSO patients. This optimal region of the ROC curve may be closest to the (0,1) point in a graph in which the ROC curve is plotted. Alternatively, a decision tree may be trained to estimate these one or more optimal thresholds. Inputs to this decision tree may include an asymmetry metric (indicative of asymmetry between nQi scores for the right-hand region of a keyboard and nQi scores for the left-hand region of the keyboard) for each of multiple dates. For instance, the multiple dates may consist of an initial "baseline" date, one or more intermediate dates, and a final date.

In this prototype, under certain circumstances for some right-handed PD patients with DSO (dominant-side-onset), asymmetry of nQi scores tends to decrease over time during the early stages of PD. This is because, under some circumstances for some DSO patients: (a) the dominant-hand performance tends to decline over time and the non-dominant-hand performance tends to improve to compensate, during the early stages of PD; and (b) as the dominant-hand performance goes down, and the non-dominant-hand performance goes up, the result is that the difference in performance of the hands decreases over time. Thus, in this prototype, in some circumstances for some DSO patients, right/left asymmetry in nQi scores (i.e., the difference between the nQi score for the right-hand keyboard region and the nQi score for the left-hand keyboard region) tends to decrease over time during the early stages of PD.

In this prototype, under certain circumstances for some PD patients with NDSO (non-dominant-side-onset), asymmetry of nQi scores tends to increase over time during the early stages of PD. This is because, under some circumstances for some NDSO patients: (a) the dominant hand is already performing better; (b) the non-dominant hand's performance gets worse during the early stages of PD; (c) this, in turn, tends to cause a slight increase in the dominant hand performance (to compensate for the non-dominant hand's decreasing performance); and (d) the result is that the differences in hand performance increases over time. Thus, in this prototype, under some circumstances for some NDSO patients, right/left asymmetry in nQi scores tends to increase over time during the early stages of PD.

The prototype that is described above is a non-limiting example of this invention. This invention may be implemented in many other ways.

In some implementations, each location-based nQi score is an nQi score for a set of keystrokes that occur in a particular region of a keyboard.

In some implementations, a nQi score for a set of keystrokes is calculated by what we call the NQi algorithm. The NQi algorithm is discussed in Giancardo, L, et al., *Computer keyboard interaction as an indicator of early Parkinson's disease*, Scientific Reports, 6:34468, Oct. 5, 2016.

The following seven paragraphs describe the NQi algorithm, as that term is used herein.

In the NQi algorithm, nQi scores are calculated from the hold time (HT) of a set of keystrokes. The HT time events are split into non-overlapping time windows (e.g., 90 second windows) to create the $B_i$ sets. From each independent $B_i$ set, a 7-element feature vector, $x_i$ is computed: 3 features that represent HT variance, and 4 features that represent a histogram of HT values. Any $B_i$ sets with fewer than a threshold number (e.g., 30) of HT values are ignored. For each feature vector, $x_i$ a single numerical score(nQi score), is generated using an ensemble regression approach. Each unit in the ensemble regression includes a linear Support Vector Regression step trained on the Unified Parkinson's Disease Rating Scale Part III (UPDRS-III), the clinical score for evaluating PD motor symptoms.

In the NQi algorithm, keystroke events are represented as follows: Let the vector a(t) represent continuous-time stochastic process of key hold times where t is the time at which each key has been pressed. Only keystrokes for which a short hold time is expected (i.e. alphanumeric characters, symbols and space bar) are considered. Let square window $\omega$ be defined such that:

$$\omega[n] = \begin{cases} 1, & \text{if } 0 \le n < N^w \\ 0, & \text{otherwise} \end{cases}$$

where $N^w$ is the size of the window expressed in seconds. In the NQi algorithm, $N^w=90$ in some use scenarios.

In the NQi algorithm, the hold time signal a(t) is partitioned with non-overlapping square windows as follows: $B_i(t) = a[t]\omega[t - iN^w]$ where t is time, $B_i$ is a vector containing the ordered list of HT samples and i is a positive integral number which serves as index to the list of vectors. In order to account for the sparsity of the hold times signal (where the user does not type continuously but instead in unpredictable bursts), all $B_i$ that have less than $N^w/3$ key presses are removed from the set. Let us define a feature vector for each $B_i$:

$$x_i = [v^{out}, v^{iqr}, v^{de}, v^{hst0}, v^{hst1}, v^{hst2}, v^{hst3}]^T$$

where: $v^{out}$ is the number of outliers in $B_i$ divided by the number of elements in $B_i$; an outlier is defined as a HT more than 1.5 interquartile ranges below the first quartile or above the third quartile; $v^{iqr}$ is a measure of the $B_i$ distribution skewness described as $(q_2-q_1)/(q_3-q_1)$ and $q_n$ is the $n^{th}$ quartile; $v^{hst_n}$ represents the $n^{th}$ bin of the $B_i$ equally-spaced normalized histogram, i.e. an approximation of the probability density function, with 4 bins from 0 to 0.5·seconds; and $v^{de}$ is a metric of finger coordination during two consecutive keystrokes.

In the NQi algorithm, $v^{de}$ is measured as $d_1-p_2$, where $d_1$ is the depress event of the first key and $p_2$ is the press event of the second key. If $d_1-p_2<0$, then $v^{de}=0$.

In the NQi algorithm, an ensemble learning approach is employed. The ensemble learning is performed by a set of base models $F':\{f_m|m\geq 0 \hat{\ } m<N^m\}$ where $N^m$ is the total number of models. (For instance, in some use scenarios, $N^m$ is 200). Each model $f_m$ receives as input an independent feature vector $x_i$ and performs a feature transformation step and a regression step as follow:

$$y_m = f_m(x_{i'}) = b_m + w_m^T x_{i'}$$

In the nQi algorithm, $f_m(x_{i'})$ is a linear ε-Support Vector Regression model implemented in LibSVM. The result is a partial estimation of the nQi score. The nQi for each $x_i$, is calculated by applying all the regression models in F on the $x_i$ vector and then calculating the median score. Using a Bagging strategy, a different set of $w_m$ and $b_m$ coefficients are generated for each $f_m$ during the training phase. Bagging allows the creation of $N^m$ views of the training dataset by generating multiple sets (or bootstrap samples) via random sampling with replacement. This approach reduces the variance in the nQi score and limits chances of overfitting.

In some cases, only a single nQi score is calculated for a particular patient for a particular day for a particular region of a keyboard. This may be achieved by averaging together all of the independent nQi scores for a particular patient for a particular date for a particular region of the keyboard.

In some implementations of this invention, a modified nQi algorithm is employed. In a modified nQi algorithm, one or more aspects of the NQi algorithm are modified. Here are three non-limiting examples. First: (a) hold times are inputs to the nQi algorithm; whereas (b) flight times may be employed (instead of, or in addition to, hold times) as inputs to a modified nQi algorithm. Second: (a) in the nQi algorithm, each feature vector includes seven statistical features $v^{out}$, $v^{iqr}$, $v^{de}$, $v^{hst_0}$, $v^{hst_1}$, $v^{hst_2}$, $v^{hst_3}$, whereas (b) in a modified nQi algorithm, the number and type of features in the feature vector may be different. For instance, in a modified nQi algorithm, each feature vector may include (instead of, or in addition to) these seven statistical features, one or more other statistical features, such as kurtosis, heteroscedasticity, and one or more statistical distance metrics (e.g., Minkowski-form, weighted-mean-variance, chi square, Kolmogorov-Smirnov, Kullback-Liebler, histogram intersection, or earth movers distance). Third, in the nQi algorithm, each ensemble unit in the ensemble regression includes a linear Support Vector Regression step trained on the UPDRS-III. In contrast, in a modified nQi algorithm, the training may be on any other clinical scale. For instance, in a modified nQi algorithm, the training may be on a different clinical scale for Parkinson's disease, or may be on a clinical scale for any other disease.

We sometimes call the output of a modified nQi algorithm a "modified nQi score". We sometimes call a modified nQi score that is derived from keystrokes in a particular region of a keyboard a "location-based modified nQi score". In some implementations of this invention, location-based modified nQi scores are employed instead of location-based nQi scores. For instance, in the PD asymmetry method described above, location-based modified nQi scores may be employed instead of location-based nQi scores.

As noted above, in some cases, nQi scores for different regions of a keyboard are calculated for each of multiple dates, and changes in these nQi scores are analyzed. The number of dates for which location-based nQi scores are calculated, and the time elapsed between these dates, may vary. For instance, in the PD asymmetry method described above, the time period between the initial (baseline) date and final date may vary. This is because, among other things, the appropriate time period may depend on the individual patient and how advanced her or his disease is. For some patients, decline may be noticeable in three months. For some other patients, decline may not be noticeable until two years. It depends on the patient's baseline and how fast the disease is progressing. In some cases, the time elapsed between initial and final dates of assessment is optimized for one or more of: a particular patient population, a particular disease, or for detecting a specific biomarker.

In some implementations, location-based nQi scores are calculated for a large number of dates (e.g., calculated for 10, 20, 100, or more dates). Increasing the number of dates for which location-based nQi scores are calculated may be advantageous, because the greater number of data points may enable patterns of change in location-based nQi scores to be detected or to be more accurately measured. For instance, in some cases, location-based nQi scores show more variation in the left-right median differences for NDSO PD patients than for DSO PD patients.

In some use scenarios, a monotonic change in right/left asymmetry of nQi scores occurs over time (e.g., a monotonic increase or monotonic decrease). For instance, a monotonic change in right/left asymmetry of nQi scores may be an indication of the success or failure of a drug regimen.

However, many PD patients exhibit fluctuations in right/left asymmetry of nQi scores over time. For instance, in a non-limiting example, right/left asymmetry of nQi scores may be tracked over time, for two patients: (a) a first patient, who has dominant-side-onset (DSO) of Parkinson's disease; and (b) a second patient, who has non-dominant-side-onset (NDSO) of Parkinson's disease. In this example, for the first patient nq1068 (who has DSO), asymmetry is computed at visit 1 (baseline), visit 3 (halfway), and visit 5 (6 months). In contrast, for the second patient (who has NDSO), asymmetry is computed for five different appointments.

In some cases, one or more statistical measures of the distribution of asymmetry of location-based nQi scores over time are employed to detect or quantify a biomarker.

In some implementations of this invention, to determine asymmetry on a given date, a computer calculates the difference between the median nQi score for the right hand on that date and the median nQi score for the left hand on that date. Alternatively or in addition, a computer may calculate a difference between mean nQi score for the right hand and mean nQi score for the left hand.

In some cases, a computer compares the number of outliers (e.g., nQi scores that deviate by more than a threshold amount from the mean) for keystrokes in the right-hand region of a keyboard to the number of outliers for keystrokes in the left-hand region of the keyboard. The relative or absolute numbers of these outliers (for the right-hand and left-hand keystroke regions) may be taken into account, when detecting or quantifying a biomarker. For patients with Parkinson's disease in which one hand is impaired more than the other, the affected hand may show more outliers in nQi scores.

In some implementations, a computer calculates distribution distance metrics that compare the right vs left distributions of nQi scores. These distance metrics may be taken into account, when detecting or quantifying a biomarker.

In some implementations of this invention, analysis of location-based nQi scores facilitates a differential diagnosis. For instance, in the nQi algorithm, an ensemble learning model has been trained to provide an assessment of severity of fine motor impairment in Parkinson's disease (PD). By comparing the distance between severity of motor impairment between the hands, a computer may derive a measurement of the level of asymmetrical degradation between the two sides of the body. This is advantageous, because fine motor decline is not unique to PD. For example, a patient with essential tremor may present a high nQi score (indicative of high level of impairment) but low asymmetrical performance, while in a PD patient may exhibit a greater distance between the motor impairment for the two hands.

In some implementations, nQi scores are computed for three categories of keystrokes: (a) keystrokes in the right-hand side of a keyboard; (b) keystrokes in the left-hand side of the keyboard; and (c) keystrokes on both sides of the keyboard (e.g., for the entire keyboard). The left-only keystrokes may be fed as inputs to create left-hand nQi scores, the right-only keystrokes may be fed as inputs to create right-hand nQi scores, and all keystrokes may be fed in as inputs to create full-keyboard nQi scores (which measure both hands rather than a single side.

Location-Based Keystroke Tensors

In some implementations, a computer calculates what we sometimes call "location-based keystroke tensors". These location-based keystroke tensors may be multidimensional arrays that represent the distribution of keystroke dynamics (such as hold time, flight time, and delay) and the position of the involved keys, both absolute in the keyboard area and relative to the preceding key.

In some cases, each location-based keystroke tensors is a bigram and is calculated as follows: A typing stream may generate a sequence of keystrokes. Based on this sequence of keystrokes, a computer may calculate consecutive bigrams that define key pair tensors. Each key pair tensor may convey information regarding a pair of two consecutive keystrokes, including: (a) the hold time of each keystroke in the pair; (b) the flight time between the keystrokes in the pair; (c) the delay between the keystrokes in the pair; (d) the key pair location (i.e., the key zone of the final keystroke of the pair); (e) key pair trajectory (i.e., the direction of the transition between the two key zones of the pair); and (f) key pair distance (i.e., a distance between the two key zones of the pair). Alternatively, the key pair location may be (a) the key zone of the initial keystroke in the pair or (b) the key zones of each keystroke in the pair. In some cases, key pair trajectory is expressed as −1 (right to left movement that changes zones), 0 (movement within same zone, or no movement within same zone), and +1 (left to right movement that changes zones).

In some cases, one or more of the location-based keystroke tensors is an n-gram (with n>2). These location-based n-grams may be employed instead or, or in addition to, bigrams. For instance, a typing stream may generate a sequence of keystrokes. Based on this sequence of keystrokes, a computer may calculate consecutive n-grams that define n-key tensors, where n>2. An n-key tensor may convey information from a set of three or more consecutive keystrokes, including: (a) hold time of each keystroke in the set; (b) flight time between keystrokes for each pair of consecutive keystrokes in the set; (c) delay between keystrokes for each pair of consecutive keystrokes in the set; (d) key set location (i.e., the key zone of the final keystroke in the set); (e) key set trajectory (i.e., the direction of the transition between key zones for each pair of consecutive keystrokes in the set); and (f) key set distance (i.e., the distance between key zones for each pair of consecutive keystrokes in the set). Alternatively, for a n-key tensor that conveys information about a set of three or more consecutive keystrokes, the key set location is (a) the key zone of the initial keystroke in the set or (b) the key zones of each keystroke in the set.

In some implementations, one or more keystroke tensors include information about key location, key trajectory, key distance, and keystroke dynamics (e.g., hold time, flight time, and delay). These data-rich keystroke tensors may enable an automated method of evaluating psychomotor impairment through keystroke dynamics, which method takes into account multi-hand and multi-digit patterns of behavior. In some implementations, this enables the analysis of asymmetrical motor degradation, as well as digit-level analysis of finger coordination and interdigit feed-forward control mechanisms (e.g., related to maximal finger force and slaving). Furthermore, in some implementations, the keystroke tensors enable automated evaluation of multiple features relevant to fine motor degradation (including among other things asymmetry, such as between fingers in the right hand and fingers in the left hand). The multiple features that are evaluated may be useful in the characterization of a wide variety of diseases, including Parkinson's disease, osteoarthritis, psoriatic arthritis, rheumatoid arthritis, amyotrophic lateral sclerosis, and multiple sclerosis.

In some implementations, a computer calculates a sequence of tensors (e.g., key pair tensors or n-key tensors, as described above), based on a stream (e.g., temporal sequence) of keystrokes. The computer may then process this sequence of tensors to calculate what we call "location-dependent keystroke distributions" of hold times, flight times and delays. The location-dependent keystroke distributions may be dependent on keystroke location (absolute, relative or both) and may also be dependent on one or both of key trajectory and key distance. In some cases, location-dependent keystroke distributions may be estimated for hold time, flight time and delay metrics using Kernel Density Estimation (KDE). Alternatively, any other method may be employed for calculating or estimating these distributions, including any clustering algorithm (e.g., k-means clustering) or histograms.

In some implementations, location-based keystroke tensors (or location-based keystroke distributions) are used as the input to a machine learning model that has been trained to evaluate whether one or more patterns of keystrokes deviate from normal. For instance, the machine learning model may be trained to evaluate patterns of bimanual motor degradation, abnormal asymmetrical performance and irregular patterns in multi-finger synergies. Training of the machine learning model may be based on a definition of what is expected as a healthy pattern versus diseased pattern. (This definition may be derived from a cross-sectional approach, since there may not be previously-known, objective metrics available to quantify the phenomena that are being measured. Control data may be used as a reference to define a healthy reference).

In some cases, the inputs to the trained machine learning model (e.g., location-based keystroke tensors or location-based keystroke distributions) are derived from keystroke data gathered on a single day. As a result, the output(s) of the trained machine learning model may provide a static description of a patient's condition as of that single day. Likewise, the inputs may be calculated from keystroke data gathered during a relatively short time window that ends, begins, includes, or is included in, a single day, and the outputs may provide a static description of a patient's condition as of that day.

Alternatively, keystroke data may be gathered during each of multiple time windows (e.g., on each of multiple days) and the inputs (e.g., location-based keystroke tensors or location-based keystroke distributions) to the trained machine learning model may be calculated for each of the multiple time windows (e.g., for each of multiple days). Thus, the inputs to the model may provide information about changes in the patient's keystroke patterns over time. As a result, the trained machine learning model may detect or quantify features that are characterized by changes over time in aspects of fine motor impairment.

In some cases, the output of the model is a vector of biomarkers that are normalized (0-1), where zero represents normal and one represents the maximum deviation from the estimated healthy patterns. For instance, the biomarkers may comprise: (a) bimanual fine motor performance; (b) asymmetry of fine motor performance, between right hand and left hand; and (c) a third metric we sometimes call "dysmetria". In some cases, the dysmetria metric may quantify a specific pattern of keystroke behavior that is characteristic of, or presented during, a particular disease (such as inter-digit synergies that characteristically occur in multiple sclerosis). In some cases, a computer outputs instructions to display the vector of biomarkers in a graphical user interface (GUI). As a non-limiting example: (a) a GUI may display, in graphical format, a vector of three biomarkers that has been outputted by a trained machine learning model; and (b), the three biomarkers may be bimanual fine motor performance, asymmetry of fine motor performance, and dysmetria (as described above in this paragraph).

In some cases, MTL (multi-task learning) is employed to analyze location-based keystroke inputs. For instance, in the MTL: (a) a first task may analyze location-based keystroke data derived from keystrokes for an entire keyboard to calculate an estimate of overall motor impairment; (b) a second task may analyze asymmetry of location-based keystroke data from different regions of a keyboard; and (c) the outputs of the first and second tasks may be fed as inputs into a third task that predicts a biomarker or that classifies between different classes (e.g., by performing a decision tree to classify among healthy fine motor performance, non-asymmetric fine motor decline, and asymmetric fine motor decline).

Keystroke Data Collection

In some use cases of this invention, keystroke data is unobtrusively gathered while a user types in a natural and free manner during the user's ordinary daily activities. Data collection software may unobtrusively collect the typing information while the user types. For instance, the user may type on a mechanical keyboard of a laptop or on separate mechanical keyboard that functions as an input device to a computer (e.g., a laptop or personal computer). The software may enable user registration/login, distribution of the data collection software and storage and management of the typing data. Once installed, the data collection software may run in the background capturing the timing information of any keyboard input. More specifically, for each keystroke the program may store the timestamps corresponding to the press and release events. In some implementations, to ensure privacy, the collected information does not include the content of each specific key. However, each keystroke may be labeled with its corresponding key category (e.g., special key), to allow filtering of key-types that engage non-standard digit kinematics (e.g. SHIFT). Alternatively or in addition, keystrokes may be labeled with key's location in a set of two or more regions of the keyboard (e.g., right side and left side). In some cases, the temporal resolution of the data collection software is 3/0.28 (mean/std) milliseconds.

Typing information, linked to each user account, may be automatically sent to a remote server for analysis. Privacy and data security may be assured at multiple levels: e.g., at the client level, the data transmission level, and the data storage level. Any typing data stored on the local machine may be encrypted and deleted from the device after sending to the remote server. Data transmission may be protected through secure hypertext transfer protocol (https). At the server level, data may be stored in a database in encrypted format. In some cases, at the server level, data regarding a particular user is accessible only by an authorized database administrator or by the user.

The data collection software may be downloaded and installed in a user's personal laptop to enable remote data collection. Running in the background, the remote monitoring software may capture timing information of keystroke press/release events, regardless of the application context and content of the typed text. This information, linked to each user account, may be encrypted and automatically sent to a remote server through the user's home internet connection.

Integrated Assessment and Treatment of Disease

In order to assess and treat disease, keystroke assessment may be employed together with one or more drugs or non-pharmacologic treatments. For instance, the drugs that treat a disease may: (a) comprise disease-modifying drugs (e.g., which cure or slow or halt the progression of the disease); (b) may provide symptomatic relief from symptoms of the disease; or (c) may mitigate adverse effects of other drugs for the disease.

In illustrative implementations, the keystroke assessment may comprise: (a) analyzing data that encodes or is derived from keystroke tensors, augmented keystroke data or enriched keystroke data, or other statistical measures of keystrokes; and (b) outputting one or more biomarkers.

As noted above, each of the biomarkers (which are outputted by the keystroke assessment) may: (a) characterize or identify a disease; (b) characterize, identify or quantify a symptom of a disease; (c) characterize, identify or quantify impairment due to a disease; or (d) characterize, identify, or quantify a functional state of a user. Each of these biomarkers: (a) may describe or quantify a condition (e.g., a health condition or functional state) as of a specific time, specific day, or specific window of time; or (b) may describe or quantify a change or pattern of change of a condition (e.g., a health condition or functional state) over time. One or more of the biomarkers may be normalized, standardized, shifted, rescaled, or clipped.

Alzheimer's Disease

In order to diagnose, monitor and treat Alzheimer's disease, keystroke assessment may be employed together with one or more drugs or other therapies. The keystroke assessment may be performed in order to diagnose and monitor Alzheimer's disease. The drug(s) may treat one or more symptoms of Alzheimer's disease, or provide a neuroprotective or other disease-modifying therapy for Alzheimer's disease, or mitigate adverse effects of one or more other drugs for Alzheimer's disease. For instance, in order to diagnose, monitor and treat Alzheimer's disease, keystroke assessment may be employed together with one or more of the following drugs (including any equivalent generic drugs or equivalent biosimilar drugs): aducanumab, donepezil, galantamine, rivastigmine, cholinesterase inhibitors, acetylcholinesterase inhibitors, memantine, citalopram, sertraline, fluoxetine, fluvoxamine, paroxetine, venlafaxine, bupropion, amitriptyline, nortriptyline, selective serotonin reuptake inhibitors, selegiline, methylphenidate, antipsychotic medication, haloperidol, risperidone, perphenazine, olanzapine, quetiapine, thioridazine, thiothixene, chlorpromazine, trifluoperazine, acetophenazine, chlorpromazine, fluphenazine, aripiprazole, trazodone, carbamazepine, valproate, gabapentin, lamotrigine, dextromethorphan, quinidine, gabapentin, pindolol, cimetidine, medroxyprogesterone acetate, diethylstilbestrol, estrogen, and leuprolide. As used herein, "AD drug" means any drug that is listed in this paragraph.

Likewise, in illustrative implementations, keystroke assessment may be employed together with any other therapy (including any preventive therapy) for Alzheimer's disease (or mild cognitive impairment). For instance, this therapy (for Alzheimer's disease or mild cognitive impairment) may comprise any nutritional therapy, (e.g., with vitamin E or spicy foods such as black pepper, paprika, hot pepper, ginger, mustard, radish, or horseradish), cognitive rehabilitation, exercise program, occupational therapy, reduction or elimination of alcohol intake, or any other non-pharmacologic therapy.

Mild Cognitive Impairment

In order to diagnose, monitor and treat mild cognitive impairment, keystroke assessment may be employed together with one or more drugs or other therapies. The keystroke assessment may be performed in order to diagnose and monitor mild cognitive impairment. The drug(s) or other therapies may treat one or more symptoms of mild cognitive impairment, or provide a neuroprotective or other disease-modifying therapy for mild cognitive impairment, or mitigate adverse effects of one or more other drugs for mild cognitive impairment.

Dementia with Lewy Bodies

In order to diagnose, monitor and treat Dementia with Lewy Bodies (DLB), keystroke assessment may be employed together with one or more drugs or other therapies. The keystroke assessment may be performed in order to diagnose and monitor DLB. The drug(s) or other therapies may treat one or more symptoms of DLB, or provide a neuroprotective or other disease-modifying therapy for DLB, or mitigate adverse effects of one or more other drugs for DLB disease. For instance, in order to diagnose, monitor and treat DLB, keystroke assessment may be employed together with one or more of the following drugs (including any equivalent generic drugs or equivalent biosimilar drugs): donepezil, rivastigmine, cholinesterase inhibitors, acetylcholinesterase inhibitors, memantine, selective serotonin reuptake inhibitors, levodopa, carbidopa-levodopa, antipsychotic medication, olanzapine, quetiapine, pimavanserin, ziprasidone, aripiprazole, paliperidone, or clozapine. As used herein, "DLB drug" means any drug that is listed in this paragraph.

Parkinson's Disease

Parkinson's disease often causes tremors, impairment of fine motor control, and/or cognitive impairment (e.g., dementia). In order to diagnose, monitor and treat Parkinson's disease, keystroke assessment may be employed together with one or more drugs or other therapies. The keystroke assessment may be performed in order to diagnose and monitor Parkinson's disease. The drug(s) may treat one or more symptoms of Parkinson's disease, or provide a neuroprotective or other disease-modifying therapy for Parkinson's disease, or mitigate adverse effects of one or more other drugs for Parkinson's disease. For instance, in order to diagnose, monitor and treat Parkinson's disease, keystroke assessment may be employed together with one or more of the following drugs (including any equivalent generic drugs or equivalent biosimilar drugs): levodopa, inhaled levodopa, delayed-release levodopa, immediate-release levodopa, levodopa in a controlled-release tablet, levodopa in an extended-release capsule, carbidopa-levodopa, benserazide-levodopa, monoamine oxidase type B (MAO B) inhibitor (e.g., selegiline, rasagiline, safinamide), anticholinergic medication (e.g., trihexyphenidyl or benztropine), amantadine, dopamine agonist, nonergot dopamine agonist (e.g., pramipexole, ropinirole, rotigotine), ergot dopamine agonist (e.g., bromocriptine, pergolide, or cabergoline), apomorphine (e.g., subcutaneously administered apomorphine, or apomorphine with a premedication such as trimethobenzamide or domperidone), catechol-O-methyl transferase (COMT) inhibitor (e.g., entacapone or tolcapone), dopaminergic medication, aromatic L-amino acid decarboxylase or DOPA decarboxylase inhibitor (e.g., benserazide, carbidopa, or methyldopa), exenatide, isradipine, nilotinib, pimavanserin (e.g., Nuplazid®), and any drug for treating Parkinson's disease dementia (e.g., rivastigimin, donepezil, memantine, cholinesterase inhibitors, or acetylcholinesterase inhibitors). As used herein, "PD drug" means any drug that is listed in this paragraph.

Likewise, in illustrative implementations, keystroke assessment may be employed together with any gene therapy for Parkinson's disease, such as any of following gene therapies: (a) infusion of GDNF (glial cell derived neurotropic factor) into brain; (b) gene therapy that induces production of GABA (gamma-aminobutyric acid); or (c) gene therapy that employs an AAV (adeno-associated viral vector) to deliver GAD (glutamic acid decarboxylase).

Multiple Sclerosis

Multiple sclerosis (MS) often causes cognitive impairment (e.g., dementia) and/or impairment of fine motor control. MS often presents with characteristic patterns of keystrokes (e.g., interdigit synergies or feed-forward control of keystrokes) that may be detected by keystroke assessment. In order to diagnose, monitor and treat multiple sclerosis, keystroke assessment may be employed together with one or more drugs or other therapies. The keystroke assessment may be performed in order to diagnose and monitor multiple sclerosis. The drug(s) may treat one or more symptoms of multiple sclerosis, or provide a disease-modifying therapy (DMT) for multiple sclerosis, or mitigate adverse effects of one or more other drugs for multiple sclerosis. For instance, in order to diagnose, monitor and treat multiple sclerosis, keystroke assessment may be employed together with one or more of the following drugs (including any equivalent generic drugs or equivalent biosimilar drugs): ocrelizumab, siponimod, interferon beta-1a, interferon beta-1b, glatiramer acetate, natalizumab, dimethyl fumarate, teriflunomide, fingolimod, cladribine, glucocorticoid (e.g., intravenous), alemtuzumab, methylprednisolone, prednisone, cyclophosphamide, methotrexate, mitoxantrone, diphenhydramine, azathioprine, cyclosporine, glatiramer acetate, natalizumab, rituximab, biotin, simvastatin, corticotropin injection gel, proton pump inhibitor, clonazepam, cyclophosphamide, dalfampridine, laquinimod, mitoxantrone, ozanimod, oral sphingosine 1-phosphate receptor modulator, anticholinergic drugs, oxybutynin, tolterodine, propantheline, propiverine, fesoterodine, solifenacin, antimuscarinic drugs, tropium chloride, cholinergic agonists, alpha-adrenergic blocking agents, tricyclic antidepressants, sympathomimetic agents, botulinum toxin injection, onabotulinumtoxinA injection, alpha antagonist medications, prazosin, terazosin, doxazosin, tamsulosin, desmopressin (oral or nasal), loperamide, natalizumab, duloxetine, selective serotonin reuptake inhibitor (S SRI), escitalopram, fluoxetine, sertraline, fluoxetine, bupropion, imipramine, desipramine, venlafaxine, modafinil, armodafinil, dextroamphetamine-amphetamine, lisdexamfetamine, methylphenidate, fluoxetine, amantadine, dalfampridine (4-aminopyridine; fampridine), potassium channel blocker, amitriptyline, gabapentin, pregabalin, baclofen, tizanidine, gabapentin, phosphodiesterase-5 inhibitors, sildenafil, gabapentin, baclofen, tizanidine, and dantrolene, benzodiazepines, and clonazepam. Likewise, in illustrative implementations, keystroke assessment may be employed together with plasma exchange to treat multiple sclerosis (e.g., acute exacerbation of multiple sclerosis). As used herein, "MS drug" means any drug that is listed in this paragraph or that is an equivalent generic (or biosimilar) drug.

Osteoarthritis

Osteoarthritis may affect, among other things, fine motor control. In order to diagnose, monitor and treat osteoarthritis, keystroke assessment may be employed together with one or more drugs or other therapies. The keystroke assessment may be performed in order to diagnose and monitor osteoarthritis. The drug(s) may treat one or more symptoms of osteoarthritis, or provide a neuroprotective or other disease-modifying therapy for osteoarthritis, or mitigate adverse effects of one or more other drugs for osteoarthritis. For instance, in order to diagnose, monitor and treat osteoarthritis, keystroke assessment may be employed together with one or more of the following drugs (including any equivalent generic drugs or equivalent biosimilar drugs): duloxetine, glucocorticoid (e.g., injected into joint), opioid (e.g., tramadol, hydromorphone, oxycodone, codeine, fentanyl, hydrocodone, hydromorphone, morphine, or meperidine), analgesic, NSAID (non-steroidal anti-inflammatory drug, such as celecoxib, piroxicam, indomethacin, meloxicam, ketoprofen, sulindac, diflunisal, nabumetone, oxaprozin, tolmetin, salsalate, etodolac, fenoprofen, flurbiprofen, ketorolac, meclofenamate, or mefenamic acid), cyclooxygenase (COX)-2 selective NSAID, nonselective NSAID, topical NSAID (e.g., topical ketoprofen), diclofenac (topical or oral), and corticosteroid (e.g., prednisone, betamethasone, cortisone, dexamethasone, hydrocortisone, methylprednisolone, prednisolone, or triamcinolone acetonide). Furthermore, in order to diagnose, monitor and treat osteoarthritis, keystroke assessment may be employed together with: (a) transcutaneous electrical nerve stimulation; or (b) platelet-rich-plasma (injected into joint). As used herein, "OA drug" means any drug that is listed in this paragraph.

Psoriatic Arthritis

Psoriatic arthritis may affect, among other things, fine motor control. In order to diagnose, monitor and treat psoriatic arthritis, keystroke assessment may be employed together with one or more drugs or other therapies. The keystroke assessment may be performed in order to diagnose and monitor psoriatic arthritis. The drug(s) may treat one or more symptoms of psoriatic arthritis, or provide a neuroprotective or other disease-modifying therapy for psoriatic arthritis, or mitigate adverse effects of one or more other drugs for psoriatic arthritis. For instance, in order to diagnose, monitor and treat psoriatic arthritis, keystroke assessment may be employed together with one or more of the following drugs (including any equivalent generic drugs or equivalent biosimilar drugs): any DMARD (disease-modifying antirheumatic drug), nonbiologic DMARD, biologic DMARD, methotrexate, leflunomide, sulfasalazine, azathioprine, apremilast, tumor necrosis factor inhibitor (TNF inhibitor), etanercept, adalimumab, infliximab, certolizumab pegol, golimumab, secukinumab, ustekinumab, ixekizumab, brodalumab, abatacept, tofacitinib, cyclosporine, acitretin, guselkumab, rituximab, NSAID, celecoxib, and piroxicam. As used herein, "PsA drug" means any drug that is listed in this paragraph.

Rheumatoid Arthritis

Rheumatoid arthritis may affect fine motor control. In order to diagnose, monitor and treat rheumatoid arthritis, keystroke assessment may be employed together with one or more drugs or other therapies. The keystroke assessment may be performed in order to diagnose and monitor rheumatoid arthritis. The drug(s) may treat one or more symptoms of rheumatoid arthritis, or provide a disease-modifying therapy for rheumatoid arthritis (e.g., by suppressing synovitis and by preventing articular bone erosions and joint space narrowing), or mitigate adverse effects of one or more other drugs for rheumatoid arthritis. For instance, in order to diagnose, monitor and treat rheumatoid arthritis, keystroke assessment may be employed together with one or more of the following drugs (including any equivalent generic drugs or equivalent biosimilar drugs): any DMARD (disease-modifying antirheumatic drug), nonbiologic DMARD, biologic DMARD, methotrexate, leflunomide, sulfasalazine, hydroxycholoroquine, Janus kinase (JAK) inhibitor, tofacitinib, baricitinib, abatacept, upadacitinib, "pan-JAK" inhibitor, peficitinib, T-cell costimulation blocker, glucocorticoids (e.g., orally ingested, injected into muscle, or injected into joint), interleukin (IL)-6 receptor antagonist, tocilizumab, sarilumab, prednisone, methylprednisolone, triamcinolone, anakinra, interleukin (IL)-1 receptor antagonist, azathioprine, tumor necrosis factor inhibitor (TNF inhibitor), etanercept, adalimumab, infliximab, certolizumab pegol, golimumab, anti-CD20 B-cell depleting monoclonal antibody, rituximab, cyclophosphamide, calcineurin inhibitor, cyclosporine, tacrolimus, NSAID, celecoxib and piroxicam. As used herein, "RA drug" means any drug that is listed in this paragraph.

Other Drugs, Uses, Treatments and Diseases

This invention is not limited to the diseases (e.g., Alzheimer's disease, dementia with Lewy bodies, Parkinson's disease, multiple sclerosis, osteoarthritis, psoriatic arthritis and rheumatoid arthritis) listed above. In illustrative implementations, keystroke assessment may be employed together with one or more drugs or therapies (e.g., non-pharmacologic therapy) in order to treat any disease (including any symptom of any disease). As a non-limiting example, keystroke assessment may be employed together with one or more drugs or therapies (e.g., non-pharmacologic therapy) in order to treat any one or more of: peripheral nerve disorders (such as carpal tunnel syndrome, Charcot-Marie-Tooth disease, chronic inflammatory demyelinating polyneuropathy, or amyloidosis), spine disease (such as spondylosis or myelopathies), and brain diseases (such as amyotrophic lateral sclerosis, frontotemporal dementia, other motor-neuron disease, stroke, and dystonia) This invention is not limited to pathological conditions. For instance, in some use scenarios, this invention is employed to monitor performance in healthy users (e.g., to measure the effect of fatigue on a healthy person).

Furthermore, this invention is not limited to the AD drugs, DLB drugs, PD drugs, MS drugs, OA drugs, PsA drugs and RA drugs listed above. As a non-limiting example, keystroke assessment may be employed together with any one or more drugs or therapies (e.g., non-pharmacologic therapy), in order to treat Alzheimer's disease, mild cognitive impairment, dementia with Lewy bodies, Parkinson's disease, multiple sclerosis, osteoarthritis, psoriatic arthritis or rheumatoid arthritis.

More Details: Integrated Assessment and Treatment

As noted above, in illustrative implementations, the keystroke assessment may comprise: (a) analyzing data that encodes or is derived from keystroke tensors, augmented keystroke data or enriched keystroke data, or other statistical measures of keystrokes; and (b) outputting one or more biomarkers. As noted above, each of the biomarkers (which are outputted by the keystroke assessment) may: (a) characterize or identify a disease; (b) characterize, identify or quantify a symptom of a disease; or (c) characterize, identify or quantify impairment due to a disease.

In some implementations, the keystroke assessment also performs one or more of the following tasks: diagnosing disease; performing differential diagnosis; identifying likely diagnoses; ranking potential diagnoses (e.g., by likelihood); quantifying impairment due to disease; quantifying severity or progression of disease; identifying types of impairment (e.g., asymmetric impairment) caused by disease; and identifying a stage of disease.

The keystroke assessment may include one or more methods described herein.

The keystroke assessment may include outputting results of the assessment. For instance, the outputted results of the assessment may comprise one or more of the following: (a) one or more biomarkers; (b) a diagnosis of one or more diseases; (c) a differential diagnosis (e.g., including a determination that a patient does not have, or is likely not to have, or has a quantified likelihood of not having, a specified disease); (d) a list of one or more possible diagnoses (e.g., ranked by likelihood) that a physician or health care worker may consider (when deciding on which further tests, if any, to perform); (e) a value that quantifies impairment due to disease; (f) a value that quantifies severity or progression of disease; (g) identification of a type of impairment (e.g., asymmetric impairment) caused by disease; and (g) identification of a stage of disease.

In some cases, the keystroke assessment includes outputting instructions for a GUI (graphical user interface) to present the results of the assessment to a user (e.g., physician, other medical worker, patient, or a friend or family member of the patient) in a graphical form. Alternatively or in addition, the keystroke assessment may include outputting the results in digital form as an input to an electronic medical records system (including any conventional electronic records system or any blockchain-implemented electronics record system) or as input to an electronic database (e.g., of a public health system). Alternatively or in addition, the keystroke assessment may include outputting the results in digital form as an input to a machine-learning algorithm. In some cases, the keystroke assessment includes anonymizing the results before outputting them.

The results of the keystroke assessment may inform the treatment of the disease. For instance, based on the keystroke assessment, the type or dosing of one or more drugs that will be or are being administered to a user may be selected or changed. For example, changing or selecting the dosing for a drug may comprise changing or selecting: (a) the amount of drug to be administered; or (b) the timing of administration of the drug. Furthermore, based on the keystroke assessment, the manner of administration (e.g., oral ingestion, intravenous, intramuscular injection, intraarticular injection, inhalation, or infusion) of one or more drugs may be selected or changed. Also, based on the keystroke assessment, a particular combination of multiple drugs (and/ or the dosing and manner of administration therefor) may be selected or changed. Also, based on the keystroke assessment, one or more non-pharmacologic treatments may be selected or changed.

As a non-limiting example, each drug that is mentioned in this section titled "More Details: Integrated Assessment and Treatment" may be: (a) an AD drug, DLB drugs, PD drug, MS drug, OA drug, PsA drug, or RA drug; or (b) a drug that is a generic version of, or biosimilar to, or otherwise equivalent to, an AD drug, DLB drugs, PD drug, MS drug, OA drug, PsA drug, or RA drug.

In some implementations of this invention, a decision to select or alter a treatment is based on both (a) the results of the keystroke assessment; and (b) one or more other factors (e.g., medical imaging, medical test results or clinical observations).

In some cases, one or more computers perform a computation that: (a) takes as inputs the results of the keystroke assessment; (b) also takes an inputs other data (e.g., data derived from medical imaging, medical test results or clinical observations); and (c) outputs a recommended selection of treatment or recommended change in treatment. For instance, the computation may comprise employing a trained machine learning algorithm to recommend a treatment or an alteration to a treatment. The recommendation may recommend the administration of one or more drugs (including selection of the drug, dosing, and manner of administration). In some cases, the one or more computers output instructions for a GUI (graphical user interface) to present the recommended treatment (or change in treatment) to a user (e.g., physician, other medical worker, patient, or a friend or family member of the patient) in a graphical form. Alternatively or in addition, the one or more computers may output, in digital format, data that encodes the recommendation (for a treatment or change in treatment) and may send the data as an input to an electronic medical records system (including any conventional electronic records system or any blockchain-implemented electronics record system), or to an electronic database (e.g., for a public health system). Alternatively or in addition, the one or more computers may output, in digital format, data that encodes the recommendation (for a treatment or change in treatment) and may send the data as an input to a machine-learning algorithm. In some cases (e.g., where the data is being sent to a machine learning algorithm or to a database for a public health system), the one or more computers may anonymize the recommendation before outputting it.

The keystrokes that are analyzed in the keystroke assessment may be performed while a user is typing naturally (e.g., bimanually with fingers on each hand) during the course of normal daily activities, without any constraints regarding content or timing of the typing. Alternatively, the keystrokes that are analyzed in the keystroke assessment may be performed by one hand at a time, or may occur while a user is typing (or attempting to type) specific content that is required for the assessment, or may occur during one or more specific time windows that is (or are) required for the assessment.

The keystrokes that are analyzed in the keystroke assessment: (a) may occur over a period of time; (b) may be measured continuously or at different intervals during the period of time; (c) may be sampled periodically or otherwise during different time windows that consist of a subset of the period of time. Thus, in many implementations of this invention, keystrokes are recorded or monitored over an extended period of time (e.g., hours, days, weeks, months, years) and changes in keystroke patterns over time are analyzed. The keystrokes may occur during the user's ordinary bimanual typing, without any constraints on the content being typed or on the timing of the typing.

The keystrokes that are analyzed in the keystroke assessment may comprise physical movements by one or more fingers. These keystrokes may comprise any interaction between a finger of a human user and a keyboard, including: (a) any mechanical keyboard with keys that physically move (e.g., depress) during keystrokes; (b) any touchscreen keyboard; (c) any QWERTY keyboard; (d) any surface that, due to AR (augmented reality) or VR (virtual reality), appears to the user to be a keyboard; and (e) any surface that, due to projected light, appears to the user to be a keyboard.

Sensors in a keyboard or touchscreen may detect the keystrokes (including timing of keystrokes). For instance, conductive sensors (e.g., in a membrane keyboard or keyboard with metal contact switches or with metal leaf contact switches) may switch electrical circuits on and off as keys are pressed and released. Or, for instance, capacitive sensors may detect when keys are pressed and released. Alternatively, a hall effect keyboard, magnetic valve keyboard, inductive keyboard, or optoelectronic keyboard may be employed to detect the keystrokes. Or, in cases where a surface appears to a user to be a keyboard (e.g., due to projected light, AR or VR), a camera or one or more other sensors may detect the keystrokes.

Data that represents or that is derived from the sensor measurements of the keystrokes may be sent to one or more computers for analysis. For instance, this data may be sent (e.g., via one or more wireless or wired communication links) over the Internet or over a wireless cellular network to a remote server for analysis. In some cases, the data is locally stored, filtered, processed, and/or buffered, before being sent to a remote computer. This local storage, filtering, processing and/or buffering may occur in one or more computers that are associated with the user. The sensor data may be provided to a remote computer and analyzed by the remote computer in real time or almost real time.

Illustrative Methods for Integrated Assessment and Treatment

Here are some non-limiting examples of methods of integrated assessment and treatment, that may be employed in this invention:

In some implementations: (a) keystroke assessment is performed, and (b) based on the keystroke assessment, a treatment for a disease is selected or modified.

In some implementations: (a) keystroke assessment is performed, and (b) a disease is treated (e.g., with one or more drugs, with one or more non-pharmacologic treatments, or with any combination thereof).

In some implementations: (a) keystroke assessment is performed; (b) based on the keystroke assessment, a treatment plan for a disease is selected or modified; and (c) a disease is treated (e.g., with one or more drugs, with one or more non-pharmacologic treatments, or with any combination thereof), in accordance with the selected or modified treatment plan.

In some implementations: (a) keystroke assessment is performed; and (b) based on the keystroke assessment and on other data (such as data derived from medical images, medical test results or clinical observations), a treatment for a disease is selected or modified.

In some implementations: (a) keystroke assessment is performed; (b) based on the keystroke assessment and on other data (such as data derived from medical images, medical test results or clinical observations), a treatment plan for a disease is selected or modified; and (c) a disease is treated (e.g., with one or more drugs, with one or more non-pharmacologic treatments, or with any combination thereof), in accordance with the selected or modified treatment plan.

In each method mentioned in this section titled "Illustrative Methods for Integrated Assessment and Treatment", the method may further comprise calculating a recommendation and outputting the recommendation (e.g., in any manner described herein).

In some implementations, software is downloaded. This software may comprise instructions for enabling one or more computers to perform keystroke assessment.

In some implementations, software is downloaded. This software may comprise instructions for enabling one or more computers (a) to perform keystroke assessment, and (b) based at least in part on the keystroke assessment, to calculate a new or modified treatment plan. For instance, the new or modified treatment plan may specify the identity, dosage, or manner of administration of one or more drugs, or may specify a non-pharmacological treatment.

In some implementations, software is downloaded. This software may comprise instructions for enabling one or more computers (a) to perform keystroke assessment, (b) based at least in part on the keystroke assessment, to calculate a new or modified treatment plan; and (c) to output a recommendation regarding the new or modified treatment plan. For instance, the new or modified treatment plan may specify the identity, dosage, or manner of administration of one or more drugs, or may specify a non-pharmacological treatment.

In each implementation mentioned in this section titled "Illustrative Methods for Integrated Assessment and Treatment": (a) the selection of treatment for a disease may include selecting one or more drugs, selecting dosage for one or more drugs, or selecting manner of administration (e.g., oral ingestion, intravenous, intramuscular injection, intraarticular injection, inhalation, or infusion) of one or more drugs; and (b) modifying treatment for a disease may include changing which drug or drugs to administer, changing the dosage for one or more drugs, or changing the manner of administration of a drug or drugs. For instance, the one or more drugs may comprise one or more AD drugs, DLB drugs, PD drugs, MS drugs, OA drugs, PsA drugs or RA drugs, or any combination thereof. Alternatively or in addition, the treatment may include non-pharmacologic treatment.

In each implementation mentioned in this section (titled "Illustrative Methods for Integrated Assessment and Treatment") or in the following section (titled "Illustrative Systems for Integrated Assessment and Treatment"), administration of a drug (or treating with a drug) may comprise prescribing the drug, physically bringing the drug to the patient, causing the drug to be physically brought to a patient, instructing a patient to take the drug, causing a patient to be instructed to take the drug (e.g., by ingesting, inhaling, or injecting), injecting or infusing the drug into a patient, causing the drug to injected or infused into a patient, aerosolizing the drug to facilitate inhalation of the drug, or causing the drug to be aerosolized to facilitate inhalation of the drug.

In each implementation mentioned in this section (titled "Illustrative Methods for Integrated Assessment and Treatment") or in the following section (titled "Illustrative Systems for Integrated Assessment and Treatment"), the one or more drugs may be in any physical form, such as a pill, tablet, capsule, liquid, or aerosol. In some cases, the one or more drugs include one or more AD drugs, DLB drugs, PD drugs, MS drugs, OA drugs, PsA drugs or RA drugs, or any combination thereof.

In each implementation mentioned in this section (titled "Illustrative Methods for Integrated Assessment and Treatment") or in the following section (titled "Illustrative Systems for Integrated Assessment and Treatment"): (a) the selection of treatment for a disease may include selecting one or more drugs, selecting dosage for one or more drugs, or selecting manner of administration of one or more drugs; and (b) modifying treatment for a disease may include changing which drug or drugs to administer, changing the dosage for one or more drugs, or changing the manner of administration (e.g., oral ingestion, intravenous, intramuscular injection, intraarticular injection, inhalation, or infusion) of a drug or drugs. Alternatively or in addition, the treatment may include non-pharmacologic treatment.

In some implementations, this invention comprises: (a) any method described herein; (b) any combination of one or more methods described herein; or (c) any combination of one or more steps of one or more methods described herein.
Illustrative Systems for Integrated Assessment and Treatment Here are some non-limiting examples of systems that are configured to the perform integrated assessment and treatment, in illustrative implementations of this invention.

In some implementations, this invention is a system that comprises: (a) one or more drugs; and (b) one or more computers that are programmed to perform keystroke assessment to determine whether or how to treat a patient with the one or more drugs.

In some implementations, this invention is a system that comprises: (a) one or more drugs; and (b) one or more computers that are programmed (i) to perform keystroke assessment, (ii) based on the keystroke assessment, to select or to modify a treatment plan for a disease, which treatment plan includes administration of the one or more drugs, and (iii) to output a recommendation for the selected or modified treatment plan.

In some implementations, this invention is a system that comprises: (a) equipment (e.g., infusion devices) for administering one or more drugs; and (b) one or more computers that are programmed (i) to perform keystroke assessment, (ii) based on the keystroke assessment, to select or to modify a treatment plan for a disease, which treatment plan includes administration of the one or more drugs, and (iii) to output a recommendation for the selected or modified treatment plan.

In some implementations, this invention is a system that comprises: (a) one or more drugs; (b) equipment (e.g., infusion devices) for administering the one or more drugs; and (c) one or more computers that are programmed (i) to perform keystroke assessment, (ii) based on the keystroke assessment, to select or to modify a treatment plan for a disease, which treatment plan includes administration of the one or more drugs, and (iii) to output a recommendation for the selected or modified treatment plan.

In some implementations, this invention is a system that comprises: (a) one or more drugs; and (b) one or more computer readable media with instructions encoded thereon for enabling one or more computers to perform keystroke assessment.

In some implementations, this invention is a system that comprises: (a) one or more drugs; and (b) one or more computer readable media with instructions encoded thereon for enabling one or more computers (i) to perform keystroke assessment, (ii) based on the keystroke assessment, to select or to modify a treatment plan for a disease, and (iii) to output a recommendation for the selected or modified treatment plan.

The computer readable media mentioned in the preceding two paragraphs are not transitory signals.
Computers In illustrative implementations of this invention, one or more computers (e.g., servers, network hosts, client computers, integrated circuits, microcontrollers, controllers, microprocessors, processors, field-programmable-gate arrays, personal computers, digital computers, driver circuits, or analog computers) are programmed or specially adapted to perform one or more of the following tasks: (1) to receive, process and analyze signals that encode data regarding keystrokes, including data regarding absolute or relative position of keystrokes in a keyboard and regarding keystroke dynamics (such as press time, release time, hold time, flight time, and delay); (2) to calculate keystroke tensors, augmented keystroke data, and enriched keystroke data or other statistical measures of keystrokes; (3) to calculate data derived from keystroke tensors, augmented keystroke data, and enriched keystroke data and/or other statistical measures of keystrokes; (4) to train a machine learning model or machine learning algorithm; (5) to employ a trained machine learning model (or trained machine learning algorithm) to predict or classify; (6) to perform supervised or unsupervised machine learning; (7) to receive data from, control, or interface with one or more sensors; (8) to perform any other calculation, computation, program, algorithm, or computer function described or implied herein; (9) to receive signals indicative of human input; (10) to output signals for controlling transducers for outputting information in human perceivable format; (11) to process data, to perform computations, and to execute any algorithm or software; and (12) to control the read or write of data to and from memory devices (tasks 1-12 of this sentence being referred to herein as the "Computer Tasks"). The one or more computers (e.g., 1111, 1113, 1115, 1124, 1125, 1126, 1130, 1141, 1142, 1143, 1160, 1161, 1162, 1163) may each comprise: (a) a central processing unit, (b) an ALU (arithmetic logic unit), (c) a memory unit, and (d) a control unit that controls actions of other components of the computer in such a way that encoded steps of a program are executed in a sequence. In some cases, the one or more computers communicate with each other or with other devices: (a) wirelessly; (b) by a wired connection, such as an electrical wire, an electrical cable or a fiber-optic link; or (c) by a combination of wireless and wired links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory computer-readable media. For example, in some cases, these instructions comprise instructions for a computer to perform any calculation, computation, program, algorithm, or computer function described or implied herein. For instance, in some cases, instructions encoded in a tangible, non-transitory, computer-accessible medium comprise instructions for a computer to perform the Computer Tasks.

Computer Readable Media

In some implementations, this invention comprises one or more computers that are programmed to perform one or more of the Computer Tasks.

In some implementations, this invention comprises one or more tangible, machine readable media, with instructions encoded thereon for one or more computers to perform one or more of the Computer Tasks. In some implementations, these one or more media are not transitory waves and are not transitory signals.

In some implementations, this invention comprises participating in a download of software, where the software comprises instructions for one or more computers to perform one or more of the Computer Tasks. For instance, the participating may comprise (a) a computer providing the software during the download, or (b) a computer receiving the software during the download.

Network Communication

In illustrative implementations of this invention, one or more devices (e.g., computers, display screens, touch screens, keyboards, and I/O devices) are configured for wireless or wired communication with other devices in a network.

For example, in some cases, one or more of these devices include a wireless module for wireless communication with other devices in a network. Each wireless module (e.g., 1112, 1114, 1116, 1150, 1151, 1152, 1153, 1154, 1155, 1156, 1157, 1158, 1159, 1171) may include (a) one or more antennas, (b) one or more wireless transceivers, transmitters or receivers, and (c) signal processing circuitry. Each wireless module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables and wiring.

In some cases, one or more computers are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), or wireless communication standard, including IEEE 802.11 (Wi-Fi®), IEEE 802.15 (Bluetooth®/Zigbee®), IEEE 802.16, IEEE 802.20, GSM (global system for mobile communications), UMTS (universal mobile telecommunication system), CDMA (code division multiple access, including IS-95, IS-2000, and WCDMA), LTE (long term evolution), or 5G (e.g., ITU IMT-2020).

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

"AD drug" is defined above.

"Alphabetic keystroke event" means a keystroke event that comprises pressing, holding or releasing an alphabetic key.

"Alphanumeric keystroke event" means a keystroke event that comprises pressing, holding or releasing an alphanumeric key.

A non-limiting example of "assessing" a health condition is to detect or to quantify a change in the health condition.

To compute "based on" specified data means to perform a computation that takes the specified data as an input.

The term "comprise" (and grammatical variations thereof) shall be construed as if followed by "without limitation". If A comprises B, then A includes B and may include other things.

The term "computer" means a computational device that is configured to perform logical and arithmetic operations. Each of the following is a non-limiting example of a "computer", as that term is used herein: (a) digital computer; (b) analog computer; (c) computer that performs both analog and digital computations; (d) microcontroller; (e) controller; (f) microprocessor; (g) processor; (h) field-programmable gate array; (i) tablet computer; (j) notebook computer; (k) laptop computer, (l) personal computer; (m) mainframe computer; (n) integrated circuit; (o) server computer; (p) client computer; and (q) quantum computer. However, a human is not a "computer", as that term is used herein.

"Computer Tasks" is defined above.

"Defined Term" means a term or phrase that is set forth in quotation marks in this Definitions section.

"DLB drug" is defined above.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

The phrase "fine motor control" is used herein in the physiological sense of the phrase, and is an attribute of a human user.

Unless the context clearly indicates otherwise: (1) a phrase that includes "a first" thing and "a second" thing does not imply an order of the two things (or that there are only two of the things); and (2) such a phrase is simply a way of identifying the two things, so that they each may be referred to later with specificity (e.g., by referring to "the first" thing and "the second" thing later). For example, if a device has a first socket and a second socket, then, unless the context clearly indicates otherwise, the device may have two or more sockets, and the first socket may occur in any spatial order relative to the second socket. A phrase that includes a "third" thing, a "fourth" thing and so on shall be construed in like manner.

"For instance" means for example.

To say a "given" X is simply a way of identifying the X, such that the X may be referred to later with specificity. To say a "given" X does not create any implication regarding X. For example, to say a "given" X does not create any implication that X is a gift, assumption, or known fact.

As used herein, a "health condition" means a disease or a symptom of a disease.

"Herein" means in this document, including text, specification, claims, abstract, and drawings.

"HIV/AIDS" means human immunodeficiency virus infection and acquired immune deficiency syndrome.

Unless the context clearly indicates otherwise, to "hold" a key means to continue to press against the key.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"I/O device" means an input/output device. Non-limiting examples of an I/O device include a touch screen, other electronic display screen, keyboard, mouse, microphone, or speaker.

Non-limiting examples of a "key", as that term is used herein, include: (a) a region of a touchscreen that is associated with a character that may be inputted by a user; (b) a key of a mechanical keyboard; and (c) a key that moves, relative to the keyboard of which it is part, when the key is pressed.

Non-limiting examples of a "keyboard", as that term is used herein, include: (a) a graphical user interface on a touchscreen, which graphical user interface enables a user to input characters; (b) a mechanical keyboard; and (c) a keyboard in which individual keys move relative to the keyboard when pressed.

"Keystroke assisted-selection event" means a selection, by a human user, of text that is displayed to the user, which text comprises one or more characters and is predicted or otherwise calculated by a computer. A non-limiting example of a keystroke assisted-selection event is a user selecting text, which text is displayed on a graphical user interface and is predicted by a computer. For instance, the selecting may comprise the user clicking on the text.

"Keystroke backspace event" means a keystroke event that comprises pressing, holding or releasing a backspace key.

"Keystroke delay time" means time that elapses between release of a key and press of the next key.

As used herein, a "keystroke event" is an event that comprises pressing, holding or releasing a key on a keyboard. As used herein, a keystroke event "for" a character means a keystroke that involves pressing, holding or releasing a key for that character.

"Keystroke hold time" means time that elapses between press of a key and release of the key.

"Keystroke flight time" means time that elapses between press of a key and press of the next key.

"Keystroke pause" means a pause between keystrokes.

To "calculate keystroke pauses between words" means to calculate, as one or more separate metrics, data regarding number, duration or sequence of pauses between words, where each pause between words is time elapsed between a keystroke event for the last letter of a word and a keystroke event for the first letter of the next word.

To "calculate keystroke pauses between sentences" means to calculate, as one or more separate metrics, data regarding number, duration or sequence of pauses between sentences, where each pause between sentences is time elapsed between a keystroke event for an end of a sentence and a keystroke event for a first character of the next sentence. For purposes of the preceding sentence, an "end" of a sentence means the last letter of the sentence or the last character of the sentence.

"Keystroke tap precision" means a measure of distance between (a) a point or region on a touchscreen, which point or region is associated with a character that may be inputted by a user; and (b) a point or region that is pressed by a user on the touchscreen.

"Keystroke trajectory" means a sequence of keystroke zones in which a sequence of keystrokes occur.

"Keystroke zonal distance" means a measure of distance between a keystroke zone for a keystroke and a keystroke zone for the next keystroke. A keystroke zonal distance may be signed or unsigned.

"Keystroke zone" means a region of a keyboard, which region includes some but not all of the keys of the keyboard.

As used herein, a single scalar is not a "matrix".

A non-limiting example of a "measurement" is a measured value. As a non-limiting example, a measurement of a keystroke event may comprise data acquired by measuring the keystroke event.

"ML" means machine learning.

"MS drug" is defined above.

Unless the context clearly indicates otherwise, "next" means next in temporal order. As a non-limiting example, if a user types a temporal sequence of the five letters A B O U T, the letter B is the "next" letter after the letter A in the sequence.

"nQi score" is defined above.

"OA drug" is defined above.

Unless the context clearly indicates otherwise, "or" means and/or. For example, A or B is true if A is true, or B is true, or both A and B are true. Also, for example, a calculation of A or B means a calculation of A, or a calculation of B, or a calculation of A and B.

"PET" means positron emission tomography.

"PsA drug" is defined above.

"PD drug" is defined above.

"RA drug" is defined above.

A group with no elements is not a "set", as that term is used herein.

"Shift keystroke event" means a keystroke event that comprises pressing, holding or releasing a shift key.

Unless the context clearly indicates otherwise, "some" means one or more.

As used herein, a "subset" of a set consists of less than all of the elements of the set.

The term "such as" means for example.

To say that a machine-readable medium is "transitory" means that the medium is a transitory signal, such as an electromagnetic wave.

Except to the extent that the context clearly requires otherwise, if steps in a method are described herein, then the method includes variations in which: (1) steps in the method occur in any order or sequence, including any order or sequence different than that described herein; (2) any step or steps in the method occur more than once; (3) any two steps occur the same number of times or a different number of times during the method; (4) one or more steps in the method are done in parallel or serially; (5) any step in the method is performed iteratively; (6) a given step in the method is applied to the same thing each time that the given step occurs or is applied to a different thing each time that the given step occurs; (7) one or more steps occur simultaneously; or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage and any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. Unless the context clearly indicates otherwise, any definition or clarification herein of a term or phrase applies to any grammatical variation of the term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising: (a) accepting, as an input, a first set of data regarding keystroke events, which keystroke events occur during typing by a user; (b) calculating, based on the first set of data, a second set of data which includes data regarding (i) keystroke hold times, keystroke flight times, or keystroke delay times, and (ii) keystroke pauses between words and keystroke pauses between sentences; (c) calculating, based on the second set of data, a set of features which is different from the first and second sets of data; (d) inputting the set of features into a machine-learning algorithm; and (e) outputting, from the machine learning algorithm, an assessment of cognitive impairment of the user. In some cases, the calculating the set of features includes computations that involve one or more autoencoder neural networks. In some cases, the machine-learning algorithm comprises an ensemble of support vector machines. In some cases, the method further comprises at least temporarily storing the second set of data in one or more variable-sized data structures. In some cases, the keystroke events occur during a typing session for which the user has not received instructions that instruct the user to type specific content. In some cases, the first set of data includes data that specifies a type, model or unique identity of a hardware device which processes the keystroke events. In some cases, the first set of data includes data that identifies a software program, which software program runs locally on a device employed by the user and processes the keystroke events. In some cases, for each particular keystroke event in at least a subset of the keystroke events, the first set of data includes data that categorizes the particular keystroke event as being in one of a set of categories, which set of categories includes: (a) a first category that consists of all alphanumeric keystroke events or of all alphabetic keystroke events; and (b) a second category that consists of at least shift keystrokes. In some cases: (a) the keystroke events include alphanumeric keystroke events; and (b) for each particular alphanumeric keystroke event in at least a subset of the alphanumeric keystroke events, the first set of data does not identify which specific key is pressed during the particular alphanumeric keystroke event. In some cases, the first set of data includes, for at least a subset of the keystroke events, data regarding keystroke tap precision. In some cases, the first set of data includes data regarding keystroke backspace events. In some cases, the first set of data includes data regarding keystroke assisted-selection events. In some cases, the second set of data includes data regarding keystroke hold times. In some cases, the second set of data includes data regarding keystroke flight times. In some cases, the second set of data includes data regarding keystroke delay times. In some cases, the assessment of cognitive impairment comprises at least one value or classification, which at least one value or classification specifies a severity of cognitive impairment. In some cases, the assessment of cognitive impairment classifies the cognitive impairment as being one of a set of conditions, which set of conditions includes dementia. In some cases, the assessment of cognitive impairment classifies the cognitive impairment as being one of a set of conditions, which set of conditions includes a clinical condition known as mild cognitive impairment. In some cases, the assessment of cognitive impairment classifies the cognitive impairment as being one of a set of conditions, which set of conditions includes a condition that consists of a type of cognitive impairment less severe than dementia. In some cases, the assessment of cognitive impairment includes a value that specifies a probability of: (a) a level of severity of cognitive impairment or (b) the presence of a particular disease that causes cognitive impairment. In some cases, the assessment of cognitive impairment comprises a diagnosis of Alzheimer's disease or of Alzheimer's disease dementia. In some cases, the assessment of cognitive impairment comprises a diagnosis of Parkinson's disease or of Parkinson's disease dementia. In some cases, the assessment of cognitive impairment comprises a diagnosis of dementia with Lewy bodies. In some cases, the assessment of cognitive impairment comprises a diagnosis of a vascular dementia. In some cases, the assessment of cognitive impairment comprises a diagnosis of frontotemporal dementia. In some cases, the method further comprises recommending treatment of the user with, or treating the user with, an acetylcholinesterase inhibitor. In some cases, the method further comprises recommending treatment of the user with, or treating the user with, memantine. In some cases, the method further comprises recommending treatment of the user with, or treating the user with, aducanumab. In some cases, the method further comprises recommending treatment of the user with, or treating the user with, an AD drug. In some cases, the method further comprises recommending treatment of the user with, or treating the user with, a PD drug. In some cases, the method further comprises recommending treatment of the user with, or treating the user with, a DLB drug. In some cases: (a) the set of features that is inputted into the machine-learning algorithm includes values of one or more functional states of the user; and (b) at least one functional state, in the one or more functional states, comprises a state of a psychological, cognitive, psychomotor, or motor function of the user. In some cases, the psychological, cognitive, psychomotor, or motor function mentioned in the preceding sentence is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring. In some cases: (a) the set of features that is inputted into the machine-learning algorithm includes values of one or more functional states of the user; and (b) at least one functional state, in the one or more functional states, comprises a state of a behavioral function of the user. In some cases, the behavioral function mentioned in the preceding sentence is one of a set of functions of the user, which set of functions consists of (i) mood, (ii) social interaction, and (iii) behavioral control. Each of the cases described above in this paragraph is an example of the method described in the first sentence of this paragraph, and is also an example of an embodiment of this invention that may be combined with other embodiments of this invention. Also, the method described in the first sentence of this paragraph may be combined with other embodiments of this invention.

In some implementations, this invention is a method comprising: (a) accepting, as an input, a first set of data regarding keystroke events, which keystroke events occur during typing by a user; (b) calculating, based on the first set of data, a second set of data which includes data regarding (i) keystroke hold times, keystroke flight times, or keystroke delay times, and (ii) keystroke zones, keystroke zonal distances or at least one keystroke trajectory; (c) calculating, based on the second set of data, a set of features which is different from the first and second sets of data; (d) inputting the set of features into a machine-learning algorithm; and (e) outputting, from the machine learning algorithm, an assessment of cognitive impairment of the user. In some cases, the calculating the set of features includes computations that involve one or more autoencoder neural networks. In some cases, the machine-learning algorithm comprises an ensemble of support vector machines. In some cases, the method further comprises at least temporarily storing the second set of data in one or more variable-sized data structures. In some cases, the keystroke events occur during a typing session for which the user has not received instructions that instruct the user to type specific content. In some cases, the first set of data includes data that specifies a type, model or unique identity of a hardware device which processes the keystroke events. In some cases, the first set of data includes data that identifies a software program, which software program runs locally on a device employed by the user and processes the keystroke events. In some cases, for each particular keystroke event in at least a subset of the keystroke events, the first set of data includes data that categorizes the particular keystroke event as being in one of a set of categories, which set of categories includes: (a) a first category that consists of all alphanumeric keystroke events or of all alphabetic keystroke events; and (b) a second category that consists of at least shift keystrokes. In some cases: (a) the keystroke events include alphanumeric keystroke events; and (b) for each particular alphanumeric keystroke event in at least a subset of the alphanumeric keystroke events, the first set of data does not identify which specific key is pressed during the particular alphanumeric keystroke event. In some cases, the first set of data includes, for at least a subset of the keystroke events, data regarding keystroke tap precision. In some cases, the first set of data includes data regarding keystroke backspace events. In some cases, the first set of data includes data regarding keystroke assisted-selection events. In some cases, the second set of data includes data regarding keystroke hold times. In some cases, the second set of data includes data regarding keystroke flight times. In some cases, the second set of data includes data regarding keystroke delay times. In some cases, the assessment of cognitive impairment comprises at least one value or classification, which at least one value or classification specifies a severity of cognitive impairment. In some cases, the assessment of cognitive impairment classifies the cognitive impairment as being one of a set of conditions, which set of conditions includes dementia. In some cases, the assessment of cognitive impairment classifies the cognitive impairment as being one of a set of conditions, which set of conditions includes a clinical condition known as mild cognitive impairment. In some cases, the assessment of cognitive impairment classifies the cognitive impairment as being one of a set of conditions, which set of conditions includes a condition that consists of a type of cognitive impairment less severe than dementia. In some cases, the assessment of cognitive impairment includes a value that specifies a probability of: (a) a level of severity of cognitive impairment or (b) the presence of a particular disease that causes cognitive impairment. In some cases, the assessment of cognitive impairment comprises a diagnosis of Alzheimer's disease or of Alzheimer's disease dementia. In some cases, the assessment of cognitive impairment comprises a diagnosis of Parkinson's disease or of Parkinson's disease dementia. In some cases, the assessment of cognitive impairment comprises a diagnosis of dementia with Lewy bodies. In some cases, the assessment of cognitive impairment comprises a diagnosis of a vascular dementia. In some cases, the assessment of cognitive impairment comprises a diagnosis of frontotemporal dementia. In some cases, the method further comprises recommending treatment of the user with, or treating the user with, an acetylcholinesterase inhibitor. In some cases, the method further comprises recommending treatment of the user with, or treating the user with, memantine. In some cases, the method further comprises recommending treatment of the user with, or treating the user with, aducanumab. In some cases, the method further comprises recommending treatment of the user with, or treating the user with, an AD drug. In some cases, the method further comprises recommending treatment of the user with, or treating the user with, a PD drug. In some cases, the method further comprises recommending treatment of the user with, or treating the user with, a DLB drug. In some cases: (a) the set of features that is inputted into the machine-learning algorithm includes values of one or more functional states of the user; and (b) at least one functional state, in the one or more functional states, comprises a state of a psychological, cognitive, psychomotor, or motor function of the user. In some cases, the psychological, cognitive, psychomotor, or motor function mentioned in the preceding sentence is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring. In some cases: (a) the set of features that is inputted into the machine-learning algorithm includes values of one or more functional states of the user; and (b) at least one functional state, in the one or more functional states, comprises a state of a behavioral function of the user.

In some cases, the behavioral function mentioned in the preceding sentence is one of a set of functions of the user, which set of functions consists of (i) mood, (ii) social interaction, and (iii) behavioral control. Each of the cases described above in this paragraph is an example of the method described in the first sentence of this paragraph, and is also an example of an embodiment of this invention that may be combined with other embodiments of this invention. Also, the method described in the first sentence of this paragraph may be combined with other embodiments of this invention.

In some implementations, this invention is a method comprising: (a) accepting, as an input, a first set of data regarding keystroke events, which keystroke events occur during typing by a user; (b) calculating, based on the first set of data, a second set of data which includes data regarding (i) keystroke hold times, keystroke flight times, or keystroke delay times, and (ii) additional metrics, which additional metrics comprise (A) keystroke pauses between words, (B) keystroke pauses between sentences, (C) keystroke zones, (D) keystroke zonal distances, or (E) at least one keystroke trajectory; (c) calculating, based on the second set of data, a set of features which is different from the first and second sets of data; (d) inputting the set of features into a machine-learning algorithm; and (e) outputting, from the machine learning algorithm, an assessment of a health condition of the user. In some cases, the calculating the set of features includes computations that involve one or more autoencoder neural networks. In some cases, the machine-learning algorithm performs ensemble machine learning. In some cases, the method further comprises at least temporarily storing the second set of data in one or more variable-sized data structures. In some cases, the keystroke events occur during a typing session for which the user has not received instructions that instruct the user to type specific content. In some cases, the first set of data includes data that specifies a type, model or unique identity of a hardware device which processes the keystroke events. In some cases, the first set of data includes data that identifies a software program, which software program runs locally on a device employed by the user and processes the keystroke events. In some cases, for each particular keystroke event in at least a subset of the keystroke events, the first set of data includes data that categorizes the particular keystroke event as being in one of a set of categories, which set of categories includes: (a) a first category that consists of all alphanumeric keystroke events or of all alphabetic keystroke events; and (b) a second category that consists of at least shift keystrokes. In some cases: (a) the keystroke events include alphanumeric keystroke events; and (b) for each particular alphanumeric keystroke event in at least a subset of the alphanumeric keystroke events, the first set of data does not identify which specific key is pressed during the particular alphanumeric keystroke event. In some cases, the first set of data includes, for at least a subset of the keystroke events, data regarding keystroke tap precision. In some cases, the first set of data includes data regarding keystroke backspace events. In some cases, the first set of data includes data regarding keystroke assisted-selection events. In some cases the second set of data includes data regarding keystroke hold times. In some cases, the second set of data includes data regarding keystroke flight times. In some cases, the second set of data includes data regarding keystroke delay times. In some cases, the assessment of health condition comprises data that specifies: (a) a level of severity of impairment; (b) a level of severity of a symptom; or (c) the presence or absence of a particular disease. In some cases, the assessment of health condition classifies the health condition as being one of a set of conditions, which set of conditions includes dementia. In some cases, the assessment of health condition classifies the health condition as being one of a set of conditions, which set of conditions includes a clinical condition known as mild cognitive impairment. In some cases, the assessment of health condition classifies the health condition as being one of a set of conditions, which set of conditions includes a condition that consists of a type of cognitive impairment less severe than dementia. In some cases, the assessment of health condition includes data that specifies a probability of: (a) a level of severity of impairment; (b) a level of severity of a symptom; or (c) the presence or absence of a particular disease. In some cases, the health condition comprises Alzheimer's disease or Alzheimer's disease dementia. In some cases, the health condition comprises Parkinson's disease or Parkinson's disease dementia. In some cases, the health condition comprises dementia with Lewy bodies. In some cases, the health condition comprises vascular dementia. In some cases, the health condition comprises fronto-temporal dementia. In some cases, the health condition comprises cognitive impairment. In some cases, wherein the health condition comprises cognitive function. In some cases, the health condition comprises impairment of sensory-motor feedback. In some cases, the health condition comprises sensory-motor feedback. In some cases, the health condition comprises an impairment of one or more behaviors. In some cases, the health condition comprises an impairment of one or more functions in a set of functions, which set of functions comprises bathing, showering, continence, putting on clothes, feeding, and getting on and off a toilet. In some cases, the health condition comprises multiple sclerosis. In some cases, the health condition comprises osteoarthritis. In some cases, the health condition comprises rheumatoid arthritis. In some cases, the health condition comprises psoriatic arthritis. In some cases, the assessment is a diagnosis of a disease or of a symptom. In some cases, the method further comprises recommending treatment of the user with, or treating the user with, an acetylcholinesterase inhibitor. In some cases, the method further comprises recommending treatment of the user with, or treating the user with, memantine. In some cases, the method further comprises recommending treatment of the user with, or treating the user with, aducanumab. In some cases, the method further comprises recommending treatment of the user with, or treating the user with, levodopa. In some cases, the method further comprises recommending treatment of the user with, or treating the user with, an AD drug. In some cases, the method further comprises recommending treatment of the user with, or treating the user with, a PD drug. In some cases, the method further comprises recommending treatment of the user with, or treating the user with, a DLB drug. In some cases, the method further comprises recommending treatment of the user with, or treating the user with, an MS drug. In some cases, the method further comprises recommending treatment of the user with, or treating the user with, an OA drug. In some cases, the method further comprises recommending treatment of the user with, or treating the user with, a PsA drug. In some cases, the method further comprises recommending treatment of the user with, or treating the user with, an RA drug. In some cases, the set of features includes one or more descriptive statistics. In some cases, the set of features includes one or more descriptive statistics regarding the keystroke events or regarding one or more subsets of the keystroke events, which descriptive statistics include one or more of mean, mode, median, measure of central tendency, measure of dispersion, variance, standard deviation, quartile, quantile, measure of asymmetry, measure of outliers, skewness, kurtosis, measure of statistical distance, measure of statistical difference or statistical similarity, Bhattacharyya distance, f-distance, probability distribution for one or more discrete variables, probability function, probability mass function, frequency distribution, relative frequency distribution, discrete probability distribution function, categorical distribution, probability distribution for one or more continuous variables, probability density function, continuous probability distribution function, cumulative distribution function, cumulative distribution function, quantile distribution function, measure of range, heteroskedasticity, measure of statistical dependence, correlation and average of medians. In some cases, the set of features includes one or more inferential statistics. In some cases, the set of features includes one or more inferential statistics regarding the keystroke events or regarding one or more subsets of the keystroke events, which inferential statistics include one or more of an interval estimate, a confidence interval, a set estimate, a point estimate, a credible interval, a clustering of data points, or a classification of data points into groups. In some cases, the method further comprises outputting instructions for one or more transducers to output, in humanly perceptible form, the assessment of health condition. In some cases, the method further comprises outputting instructions for one or more transducers to output, via a graphical user interface, the assessment of health condition. In some cases, the method further comprises outputting instructions for one or more transducers to send, by email, by phone, or by social media, a signal regarding the assessment of health condition. In some cases: (a) the set of features that is inputted into the machine-learning algorithm includes values of one or more functional states of the user; and (b) at least one functional state, in the one or more functional states, comprises a state of a psychological, cognitive, psychomotor, or motor function of the user. In some cases, the psychological, cognitive, psychomotor, or motor function mentioned in the preceding sentence is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring. In some cases: (a) the set of features that is inputted into the machine-learning algorithm includes values of one or more functional states of the user; and (b) at least one functional state, in the one or more functional states, comprises a state of a behavioral function of the user. In some cases, the behavioral function mentioned in the preceding sentence is one of a set of functions of the user, which set of functions consists of (i) mood, (ii) social interaction, and (iii) behavioral control. Each of the cases described above in this paragraph is an example of the method described in the first sentence of this paragraph, and is also an example of an embodiment of this invention that may be combined with other embodiments of this invention. Also, the method described in the first sentence of this paragraph may be combined with other embodiments of this invention.

In some implementations, this invention comprises one or more non-transitory computer readable media with instructions encoded thereon for enabling one or more processors to perform the operations of: (a) accepting, as an input, a first set of data regarding keystroke events, which keystroke events occur during typing by a user; (b) calculating, based on the first set of data, a second set of data which includes data regarding (i) keystroke hold times, keystroke flight times, or keystroke delay times, and (ii) additional metrics, which additional metrics comprise (A) keystroke pauses between words, (B) keystroke pauses between sentences, (C) keystroke zones, (D) keystroke zonal distances, or (E) at least one keystroke trajectory; (c) calculating, based on the second set of data, a set of features which is different from the first and second sets of data(d) inputting the set of features into a machine-learning algorithm; and (e) outputting, from the machine learning algorithm, an assessment of a health condition of the user; wherein none of the one or more computer-readable media is a transitory signal. The one or more non-transitory computer readable media described above in this paragraph may be combined with other embodiments of this invention.

In some implementations, this invention is a method comprising: (a) accepting, as an input, a first set of data regarding keystroke events, which keystroke events occur during typing by a user; (b) calculating, based on the first set of data, a second set of data which includes data regarding (i) keystroke hold times, keystroke flight times, or keystroke delay times, and (ii) additional metrics, which additional metrics comprise (A) keystroke pauses between words, (B) keystroke pauses between sentences, (C) keystroke zones, (D) keystroke zonal distances, or (E) at least one keystroke trajectory; and (c) calculating, based on the second set of data, one or more functional states of the user, wherein at least one of the one or more functional states is a state of a psychological, cognitive, psychomotor, or motor function of the user. In some cases, the psychological, cognitive, psychomotor, or motor function mentioned in the preceding sentence is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring. Each of the cases described above in this paragraph is an example of the method described in the first sentence of this paragraph, and is also an example of an embodiment of this invention that may be combined with other embodiments of this invention. Also, the method described in the first sentence of this paragraph may be combined with other embodiments of this invention.

In some implementations, this invention comprises one or more non-transitory computer readable media with instructions encoded thereon for enabling one or more processors to perform the operations of: (a) accepting, as an input, a first set of data regarding keystroke events, which keystroke events occur during typing by a user; (b) calculating, based on the first set of data, a second set of data which includes data regarding (i) keystroke hold times, keystroke flight times, or keystroke delay times, and (ii) additional metrics, which additional metrics comprise (A) keystroke pauses between words, (B) keystroke pauses between sentences, (C) keystroke zones, (D) keystroke zonal distances, or (E) at least one keystroke trajectory; and (c) calculating, based on the second set of data, one or more functional states of the user, wherein at least one of the one or more functional states is a state of a psychological, cognitive, psychomotor, or motor function of the user; wherein none of the one or more computer-readable media is a transitory signal. In some cases, the psychological, cognitive, psychomotor, or motor function mentioned in the preceding sentence is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring. Each of the cases described above in this paragraph is an example of the one or more non-transitory computer readable media described in the first sentence of this paragraph, and is also an example of an embodiment of this invention that may be combined with other embodiments of this invention. Also, the one or more non-transitory computer readable media described in the first sentence of this paragraph may be combined with other embodiments of this invention.

Each description herein (or in any of the Provisionals) of any method, apparatus or system of this invention describes a non-limiting example of this invention. This invention is not limited to those examples, and may be implemented in other ways.

Each description herein (or in any of the Provisionals) of any prototype of this invention describes a non-limiting example of this invention. This invention is not limited to those examples, and may be implemented in other ways.

Each description herein (or in any of the Provisionals) of any implementation, embodiment or case of this invention (or any use scenario for this invention) describes a non-limiting example of this invention. This invention is not limited to those examples, and may be implemented in other ways.

Each Figure, diagram, schematic or drawing herein (or in any of the Provisionals) that illustrates any feature of this invention shows a non-limiting example of this invention. This invention is not limited to those examples, and may be implemented in other ways.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are also within the scope of the present invention. Numerous modifications may be made by those skilled in the art without departing from the scope of the invention. Also, this invention includes without limitation each combination and permutation of one or more of the items (including any hardware, hardware components, methods, processes, steps, software, algorithms, features, and technology) that are described herein.

What is claimed is:

1. A method comprising:
   receiving electrical signals associated with an I/O device to generate a first set of data the first set of data comprising keystroke events, wherein the keystroke events occur during typing by a user;
   generating a plurality of keystroke tensors from the first set of data, each keystroke tensor associated with a different typing session for the user, each keystroke tensor comprising at least one first keystroke metric and at least one second keystroke metric, the at least one first keystroke metric comprising at least one of keystroke hold times, keystroke flight times, and keystroke delay times, the at least one second keystroke metric comprising at least one of keystroke pauses between words, keystroke pauses between sentences, keystroke zones, keystroke zonal distances, and keystroke trajectories;
   generating a set of features by executing at least one of feature selection and feature extraction on the plurality of keystroke tensors wherein the at least one of feature selection and feature extraction comprises at least one of autoencoding techniques, dimensionality reduction techniques, and statistical modeling techniques;
   inputting the set of features into a machine-learning algorithm; and
   outputting, from the machine learning algorithm, an assessment of a health condition of the user.

2. The method of claim 1, wherein generating a plurality of keystroke tensors from the first set of data is done in real-time or near real-time.

3. The method of claim 1, wherein the machine-learning algorithm performs ensemble machine learning.

4. The method of claim 1, wherein the keystroke events occur during a typing session for which the user has not received instructions that instruct the user to type specific content.

5. The method of claim 1, wherein the first set of data includes data that specifies a type, model or unique identity of a hardware device which processes the keystroke events.

6. The method of claim 1, wherein, for each particular keystroke event in at least a subset of the keystroke events, the first set of data includes data that categorizes the particular keystroke event as being in one of a set of categories, which set of categories includes:
   (a) a first category that consists of all alphanumeric keystroke events or of all alphabetic keystroke events; and
   (b) a second category that consists of at least shift keystrokes.

7. The method of claim 1, wherein:
   (a) the keystroke events include alphanumeric keystroke events; and
   (b) for each particular alphanumeric keystroke event in at least a subset of the alphanumeric keystroke events, the first set of data does not identify which specific key is pressed during the particular alphanumeric keystroke event.

8. The method of claim 1, wherein the first set of data includes, for at least a subset of the keystroke events, data regarding keystroke tap precision.

9. The method of claim 1, wherein the first set of data includes data regarding keystroke assisted-selection events.

10. The method of claim 1, wherein the assessment of health condition comprises data that specifies: (a) a level of severity of impairment; (b) a level of severity of a symptom; or (c) a presence or absence of a particular disease.

11. The method of claim 1, wherein the assessment of health condition classifies the health condition as being one of a set of conditions, which set of conditions includes dementia.

12. The method of claim 1, wherein the health condition comprises cognitive impairment.

13. The method of claim 1, wherein the health condition comprises Alzheimer's disease, Alzheimer's disease dementia, Parkinson's disease or Parkinson's disease dementia.

14. The method of claim 1, wherein:
(a) the set of features that is inputted into the machine-learning algorithm includes values of one or more functional states of the user; and
(b) at least one functional state, in the one or more functional states, comprises a state of a psychological, cognitive, psychomotor, or motor function of the user.

15. The method of claim 14, wherein the psychological, cognitive, psychomotor, or motor function is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring.

16. The method of claim 1, wherein the machine learning algorithm has been trained using a multi-regressor technique operable to at least one of identify, quantify and predict a performance condition wherein the performance condition is associated with at least one of an impairment and fatigue.

17. The method of claim 1, wherein the assessment of a health condition comprises an indication of a presence of an impairment, wherein the indication of the presence of an impairment comprises a degree of severity of the impairment as determined by the machine-learning algorithm.

18. A computing system for assessing a health status of an individual based on keystroke events, the computing system comprising:
at least one computing processor; and
memory comprising instructions that, when executed by the at least one computing processor, enable the computing system to:
receive electrical signals associated with an I/O device to generate a first set of data, the first set of data comprising keystroke events, wherein the keystroke events occur during typing by a user;
generate a plurality of keystroke tensors from the first set of data, each keystroke tensor associated with a different typing session for the user, each keystroke tensor comprising at least one first keystroke metric and at least one second keystroke metric, the at least one first keystroke metric comprising at least one of keystroke hold times, keystroke flight times, and keystroke delay times, the at least one second keystroke metric comprising at least one of keystroke pauses between words, keystroke pauses between sentences, keystroke zones, keystroke zonal distances, and keystroke trajectories;
generate a set of features by executing at least one of feature selection and feature extraction on the plurality of keystroke tensors wherein the at least one of feature selection and feature extraction comprises at least one of autoencoding techniques, dimensionality reduction techniques, and statistical modeling techniques;
inputting the set of features into a machine-learning algorithm; and
output, from the machine learning algorithm, an assessment of a health condition of the user.

19. One or more non-transitory computer readable media with instructions encoded thereon for enabling one or more processors to perform the operations of:
receiving electrical signals associated with an I/O device to generate a first set of data the first set of data comprising keystroke events, wherein the keystroke events occur during typing by a user;
generating a plurality of keystroke tensors from the first set of data, each keystroke tensor associated with a different typing session for the user, each keystroke tensor comprising at least one first keystroke metric and at least one second keystroke metric, the at least one first keystroke metric comprising at least one of keystroke hold times, keystroke flight times, and keystroke delay times, the at least one second keystroke metric comprising at least one of keystroke pauses between words, keystroke pauses between sentences, keystroke zones, keystroke zonal distances, and keystroke trajectories;
generating a set of features by executing at least one of feature selection and feature extraction on the plurality of keystroke tensors wherein the at least one of feature selection and feature extraction comprises at least one of autoencoding techniques, dimensionality reduction techniques, and statistical modeling techniques;
inputting the set of features into a machine-learning algorithm; and
outputting, from the machine learning algorithm, an assessment of a health condition of the user;
wherein none of the one or more computer-readable media is a transitory signal.

20. The one or more computer-readable media of claim 19, wherein the assessment includes a psychological, cognitive, psychomotor, or motor function is one of a set of functions of the user, which set of functions consists of (i) balance, (ii) reaction time, (iii) physical strength, (iv) body awareness, (v) coordination, (vi) tremor, (vii) speech, (viii) facial expression, (ix) agility, (x) gait, (xi) motion fluidity, (xii) respiratory quality, (xiii) dexterity, (xiv) bilateral hand coordination, (xv) right hand coordination, (xvi) left hand coordination, (xvii) steadiness, (xviii) precision, (xix) general velocity, (xx) seasonality of motor stability, (xxi) central processing, (xxii) executive function, (xxiii) complex attention, (xxiv) nonverbal memory, (xxv) language skills and verbal skills, (xxvi) social cognition, (xxvii) visual motor ability, (xxviii) processing speed, (xxix) attention and concentration, (xxx) perception, (xxxi) sensation, (xxxii) visuospatial function, (xxxiii) verbal memory, and (xxxiv) mental tracking and mental monitoring.

* * * * *